(12) United States Patent  
Peng et al.

(10) Patent No.: US 8,664,406 B2
(45) Date of Patent: Mar. 4, 2014

(54) FLUORESCENT PROBE COMPOUNDS, PREPARATION METHOD AND USE THEREOF

(75) Inventors: Xiaojun Peng, Dalian (CN); Jiangli Fan, Dalian (CN); Jianjun Du, Dalian (CN); Jingyun Wang, Dalian (CN); Jianzhou Zhang, Dalian (CN); Shiguo Sun, Dalian (CN)

(73) Assignees: Dalian University of Technology, Dalian, Liaoning (CN); Dalian Chromas Bioscience Co., Ltd., Dalian, Liaoning (CN)

( * ) Notice: Subject to any disclaimer, the term of this patent is extended or adjusted under 35 U.S.C. 154(b) by 0 days.

(21) Appl. No.: 13/513,862

(22) PCT Filed: Dec. 3, 2010

(86) PCT No.: PCT/CN2010/079416
§ 371 (c)(1),
(2), (4) Date: Jul. 7, 2012

(87) PCT Pub. No.: WO2011/066804
PCT Pub. Date: Jun. 9, 2011

(65) Prior Publication Data
US 2013/0137879 A1 May 30, 2013

(30) Foreign Application Priority Data
Dec. 3, 2009 (CN) .......................... 2009 1 0199845

(51) Int. Cl.
*C07D 209/44* (2006.01)
(52) U.S. Cl.
USPC ........................................ 548/418

(58) Field of Classification Search
USPC ........................................ 548/418
See application file for complete search history.

(56) References Cited

PUBLICATIONS

Du, et al. Organic Letters, 2010, vol. 12, No. 3, 476-479.*

* cited by examiner

*Primary Examiner* — Shawquia Young
(74) *Attorney, Agent, or Firm* — Novick, Kim & Lee, PLLC; Allen Xue

(57) ABSTRACT

The disclosure provides fluorescence probe compounds of formula I, their preparation methods and applications.

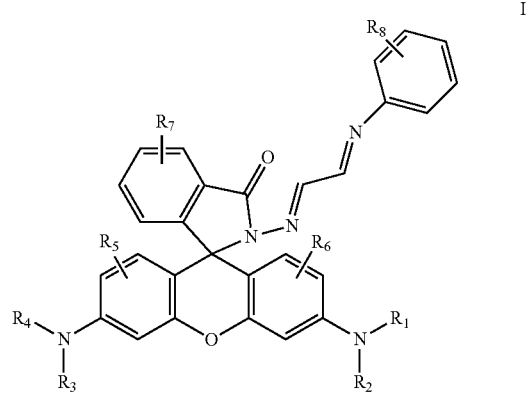

These compounds are useful in detecting mercury ions.

10 Claims, 17 Drawing Sheets

FLUORESCENT PROBE COMPOUNDS, PREPARATION METHOD AND USE THEREOF

TECHNICAL FIELD

The present invention relates to a fluorescent probe for $Hg^{2+}$ detection in fine chemical field.

BACKGROUND ART

Mercury ion is one of the most toxic and dangerous heavy metal elements. And it would induce permanent harm to brain, bone, kidney, central nervous system, immune system and endocrine system. Mercury and mercury-contaminating material are widespread through various routes, e.g. volcanic eruption, mining and solid waste incineration, resulting in vast amounts of water, air and soil are contaminated. Subsequent bioaccumulation through the food chain can lead to severe damages to people's health. Thus sensitive detection of $Hg^{2+}$ in environmental samples and corresponding study on biology become one of the hottest topics recently.

Although there are many detection methods for metal ions, such as atomic absorption and electron paramagnetic resonance, these methods are not suitable for direct and on-site detection of metal ions in biological body, and pretreatment of sample is complex as well, thus their applications are limited. On the other hand, the method based on fluorescent probe attracts much attention due to its high sensitivity, good selectivity, quick respond and suitability for on-site detection. However, among most of fluorescent probes for $Hg^{2+}$ detection on the basis of coordination mechanism like PET and ICT, the one having good properties and suitable for detecting $Hg^{2+}$ in low level is little. Since $Hg^{2+}$ could quench fluorescence because of its heavy atom effect, and $Pb^{2+}$, $Zn^{2+}$ and $Ag^+$ usually disturb the detection of $Hg^{2+}$, a new kind of probe based on ion-selective reaction is developed to avoid low sensitivity and low selectivity of the fluorescent probe based on coordination mechanism mentioned above.

Up to now, thioether fluorescence probe and desulfurization fluorescence probe are main examples of probes selective for $Hg^{2+}$, but there are also some deficiencies in their performance. For the fluorescence probe based on thioether-$Hg^{2+}$ coordination, the binding ability of thioether to $Hg^{2+}$ is not very strong which impedes the application for detecting low-concentration $Hg^{2+}$ in physiological environment (Knut Rurack, Ute Resch-Genger, Monika Spieles and Julia L. Bricks, *Chem. Commun.*, 2000, 2103-2104). Desulfurization fluorescence probe is developed in the recent years, which exhibits many advantages such as pH insensitivity and large fluorescence enhancement. However, sometimes high temperature is needed to promote the desulfurization with a vast of $Hg^{2+}$, and in addition this detection may be disturbed by $Ag^+$ and $Pb^{2+}$ (Mi Young Chae and Anthony W. Czarnik, *J. Am. Chem. Soc.* 1992, 114, 9704-9705; Song, K. C., Kim, J. S., Park, S. M., Chung, K.-C., Ahn, S, and Chang, S.-K. *Org. Lett.* 2006, 8, 3413-3416).

SUMMARY OF THE INVENTION

Therefore it is still in great demand of a novel fluorescent probe for $Hg^{2+}$ detection to avoid disadvantages mentioned above currently.

In this invention, a new rhodamine-based fluorescent probe suitable for the detection of $Hg^{2+}$ in a low level and fluorescence imaging in living cells with good sensitivity, was designed and synthesized, to improve the disadvantages of the reported coordination-based probes.

The applicant of the present invention found that, $Hg^{2+}$ can promote the hydrolysis of rhodamine-based probe synthesized in the present invention to corresponding rhodamine dye, which can evidently enhance UV-Vis absorption and fluorescence emission. Therefore, the rhodamine-based probe of the present invention can be used for $Hg^{2+}$ detection in environment within ppb level as well as fluorescence imaging of $Hg^{2+}$ in living cells to conquer the disadvantages in normal methods.

In the present invention, the rhodamine-based probe was used, through $Hg^{2+}$ induced coordination and subsequent hydrolysis, obvious enhanced UV-Vis absorption and fluorescence emission can be seen by naked eyes.

For the rhodamine-based probe designed on the basis of hydrosis mechanism can be hydrosized to rhodamine B after detecting $Hg^{2+}$, which results in an evident enhancement in fluorescence and UV-Vis absorption. The recognition reaction is very mild and can complete at room temperature. Moreover, the probe is little disturbed by external factors in detecting $Hg^{2+}$ and exhibits good selectivity and anti-disturbing ability especially towards the interference from sulfide. And the probe shows good sensitivity, displays an evident fluorescence enhancement even when $Hg^{2+}$ is in ppb level, and exhibits a good linear relation between the fluorescence enhancement and the concentration of $Hg^{2+}$. Applications for detecting $Hg^{2+}$ in sea water and fluorescence imaging of $Hg^{2+}$ in living cells can be performed by using the probe.

The rhodamine-based fluorescent probe for $Hg^{2+}$ detection described in this invention includes the following general formula I.

wherein,

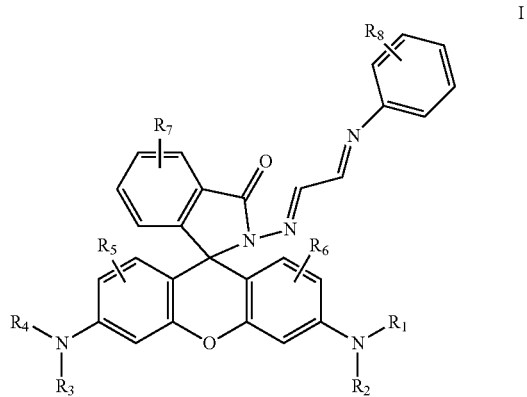

$R_1$, $R_2$, $R_3$ and $R_4$ are each independently selected from the group consisting of H, $C_{1-18}$ alkyl, $C_{1-18}$ alkyl substituted phenyl, $C_{1-18}$ alkyl substituted naphthyl, halogen, $OR_9$, $N(R_9)_2$, CN, $(CH_2CH_2O)_nH$, $(CH_2)_mCOOM$ and $(CH_2)_m SO_3M$;

$R_5$, $R_6$, $R_7$ and $R_8$ are each independently selected from the group consisting of H, $C_{1-18}$ alkyl, $C_{1-18}$ alkyl substituted phenyl, $C_{1-18}$ alkyl substituted naphthyl, halogen, hydroxyl, mercapto group, cyano group, nitro group, heterocyclic group, halogenated alkyl group, alkyl amino group, acylamino group, $OR_9$, $N(R_9)_2$, $(CH_2CH_2O)_nH$, $(CH_2)_mCOOM$ and $(CH_2)_m SO_3M$;

$R_9$ is selected from the group consisting of H, $C_{1-18}$ alkyl, $C_{1-18}$ alkyl substituted phenyl, $C_{1-18}$ alkyl substituted naphthyl, halogen, CN, $(CH_2CH_2O)_nH$, $(CH_2)_mCOOM$ and $(CH_2)_m SO_3M$;

n and m are integer from 0-18;

M is selected from the group consisting of H, K, Na, Li, $NH_4$, $NH_3R_{10}$, $NH_2(R_{10})_2$, $NH(R_{10})_3$ and $N(R_{10})_4$;

$R_{10}$ is selected from the group consisting of H, $C_{1-6}$ alkyl and $CH_2CH_2OH$.

In addition, the present invention further provided a method for synthesizing the above-mentioned compound of Formula I, which includes the following steps:

(1) synthesis of intermediate II by reacting rhodamine fluorescence dye of formula I' with lactone-ring and hydrazine hydrate II: the rhodamine fluorescence dye of formula I' is added into an alcohol solvent and stirred at room temperature so that the rhodamine fluorescence dye is evenly dispersed in the alcohol solvent; hydrazine hydrate in an excessive amount stoichiometrically is added dropwise; after finishing the addition of hydrazine hydrate, the mixture is heated to reflux the solvent and reacted until the reaction solution becomes clear; after the solution is cooled down to room temperature, the solvent is removed by evaporation; acid is added to adjust pH to 2 to 5 and then base solution is added under stirring to adjust pH to 9 to 10 to obtain precipitation; the obtained precipitation is filtered and washed, dried under vacuum and purified by recrystallization or column chromatography.

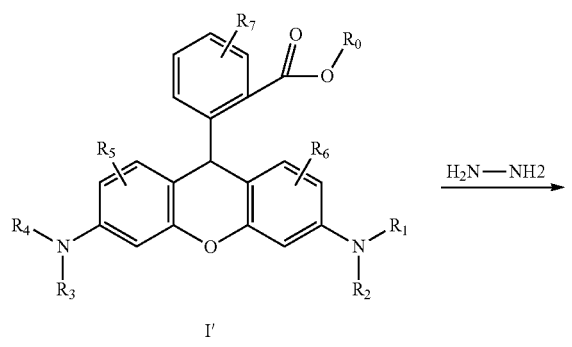

I'

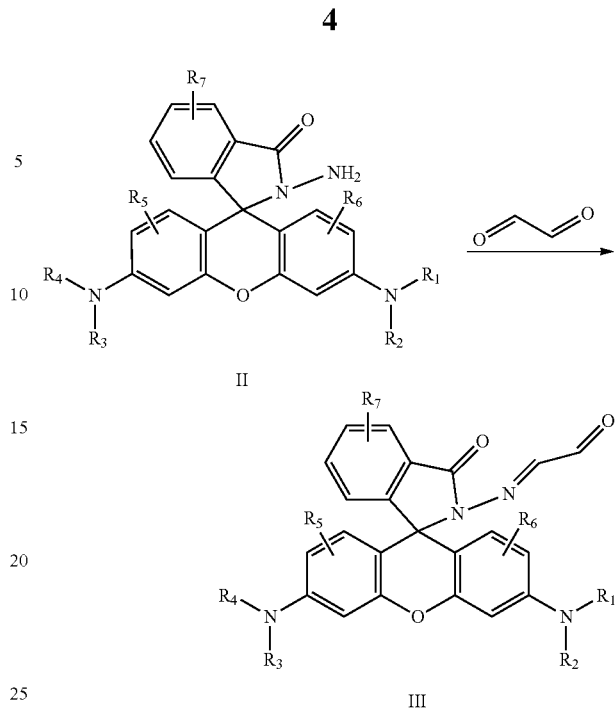

(2) synthesis of compound of formula III by reacting the intermediate II obtained in (1) and glyoxal: the intermediate II is added into reactor, and then alcohol solvent, and glyoxal in an excessive amount stoichiometrically are added; the mixture is stirred and reacted for 1 to 3 h at room temperature; the solvent is removed by evaporation, and purification is carried out through recrystallization or column chromatography to obtain the compound of formula III.

$R_0$ is selected from the group consisting of H and $C_{1-6}$ alkyl.

(3) synthesis of compound of formula I by reacting the intermediate III obtained in (2) and $R_8$ substituted aniline compound: the compound of formula III is added into reactor, and then alcohol solvent and an excessive amount of aniline compound are added; the mixture is stirred and reacted for 1 to 3 h at room temperature; the solvent is removed by evaporation, and purification is carried out through recrystallization or column chromatography to obtain the compound of formula I.

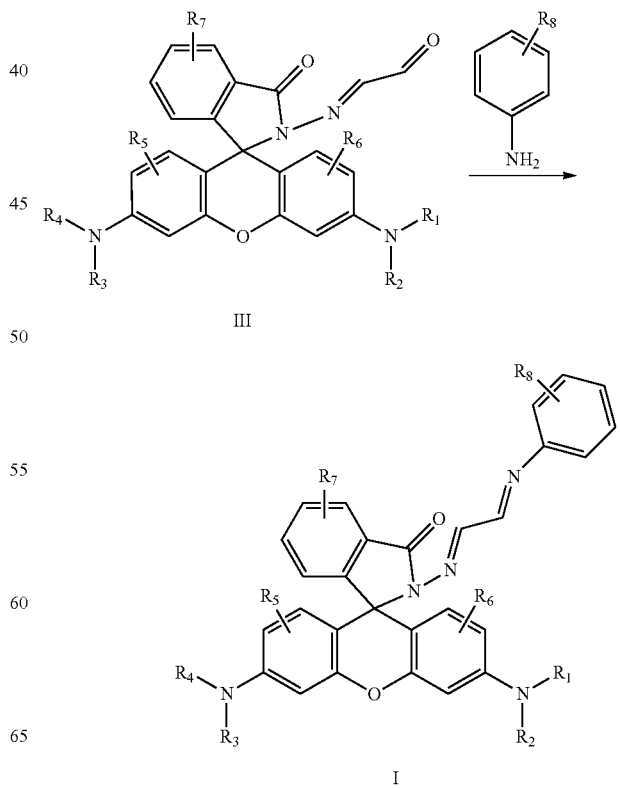

$R_0$ in formula I' is selected from H or $C_{1-6}$ alkyl, and $R_1$, $R_2$, $R_3$, $R_4$, $R_5$, $R_6$, $R_7$, $R_8$, $R_9$, $R_{10}$, n, m and M in formulas I' and formulas I to III are defined as above.

In another aspect, the present invention also provides a conjugate of the compound of formula I.

In another aspect, the present invention also provides a detection method of $Hg^{2+}$ using the compound of formula I and its conjugate.

In another aspect, the present invention also provides a composition consisting of the compound of formula I or its conjugate. The composition is also be used for $Hg^{2+}$ detection.

The characteristics and advantages of the present invention can be easily understood referred to the drawings and the mode for carrying out the invention.

MODE FOR CARRYING OUT THE INVENTION

Figure 1:
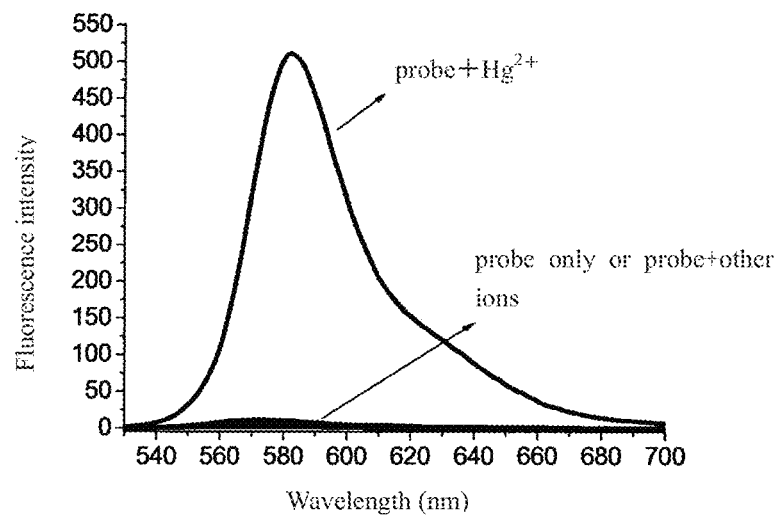
FIG. 1 is fluorescence emission spectra of fluorescence probe RHg1 in Example 1 coordinating $Hg^{2+}$ over other metal ions. Concentration of RHg1 is 5 µM, and concentrations of the metal ions are 50 equivalence ($Hg^{2+}$ is 15 equivalence). X-axis is wavelength (nm) and Y-axis is fluorescence intensity. The instrument is fluorospectrophotometer, model: LS 55.
Figure 2:
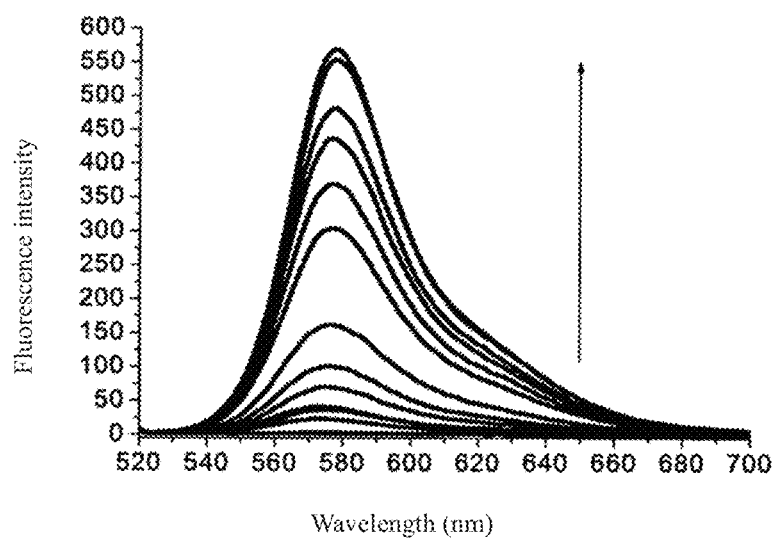
FIG. 2 is fluorescence emission spectra of RHg1 versus $Hg^{2+}$ concentration. X-axis is wavelength (nm) and Y-axis is fluorescence intensity. Concentration of RHg1 is 5 µM, and concentrations of $Hg^{2+}$ are 0, 15, 20, 25, 30, 35, 40, 45, 50, 55, 60, 65, 70, 75 and 80 µM, respectively. The instrument is fluorospectrophotometer, model: LS 55.

The terms used in the present invention have the following definitions, unless otherwise stated.

The term "alkyl" used herein includes straight and branched alkyl groups. In reference to a single alkyl such as "propyl", it specifically means a straight alkyl group, while in reference to a single branched alkyl such as "isopropyl", it specifically means a branched alkyl group. For example, "$C_{1-6}$ alkyl" includes $C_{1-4}$ alkyl, $C_{1-3}$ alkyl, methyl, ethyl, n-propyl, isopropyl and tert-butyl. The similar rule is also applicable for other groups used in the present specification.

The term "halogen" used herein includes fluorine, chlorine, bromine and iodine. Compound and its conjugate in this invention The rhodamine-based fluorescence probe described in this invention includes the following general formula I.

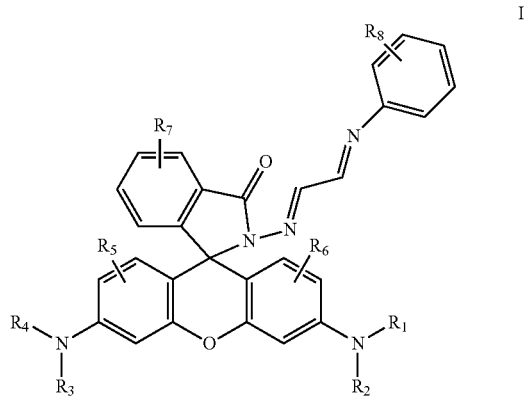

$R_1$, $R_2$, $R_3$ and $R_4$ are each independently selected from the group consisting of H, $C_{1-18}$ alkyl, $C_{1-18}$ alkyl substituted phenyl, $C_{1-18}$ alkyl substituted naphthyl, halogen, $OR_9$, $N(R_9)_2$, CN, $(CH_2CH_2O)_nH$, $(CH_2)_mCOOM$ and $(CH_2)_mSO_3M$;

$R_5$, $R_6$, $R_7$ and $R_8$ are each independently selected from the group consisting of H, $C_{1-18}$ alkyl, $C_{1-18}$ alkyl substituted phenyl, $C_{1-18}$ alkyl substituted naphthyl, halogen, hydroxyl, mercapto group, cyano group, nitro group, heterocyclic group, halogenated alkyl, alkyl amino group, acylamino group, $OR_9$, $N(R_9)_2$, $(CH_2CH_2O)_nH$, $(CH_2)_mCOOM$ and $(CH_2)_mSO_3M$;

$R_9$ is selected from the group consisting of H, $C_{1-18}$ alkyl, $C_{1-18}$ alkyl substituted phenyl, $C_{1-18}$ alkyl substituted naphthyl, halogen, CN, $(CH_2CH_2O)_nH$, $(CH_2)_mCOOM$ and $(CH_2)_m SO_3M$;

n and m are from 0 to 18;

M is selected from the group consisting of H, K, Na, Li, $NH_4$, $NH_3R_{10}$, $NH_2(R_{10})_2$, $NH(R_{10})_3$ and $N(R_{10})_4$;

$R_{10}$ is selected from the group consisting of H, $C_{1-6}$ alkyl and $CH_2CH_2OH$.

It is preferred that $R_1$, $R_2$, $R_3$ and $R_4$ are each independently selected from H or $C_{1-18}$ alkyl, H or $C_{1-12}$ alkyl is more preferable, and H or $C_{1-6}$ alkyl is most preferable.

It is preferred that $R_5$, $R_6$, $R_7$ and $R_8$ are each independently selected from the group consisting of H, $C_{1-12}$ alkyl, $C_{1-12}$ alkyl substituted phenyl, $C_{1-12}$ alkyl substituted naphthyl, halogen, hydroxyl, mercapto group, cyano group, nitro group, heterocyclic group, halogenated alkyl group, alkyl amino group, acylamino group, $OR_9$, $N(R_9)_2$, $(CH_2CH_2O)_n$ H, $(CH_2)_mCOOM$ and $(CH_2)_mSO_3M$, and H, $C_{1-6}$ alkyl, $C_{1-6}$ alkyl substituted phenyl, $C_{1-6}$ alkyl substituted naphthyl, halogen, hydroxyl, mercapto group, cyano group, nitro group, heterocyclic group, halogenated alkyl group, alkyl amino group, acylamino group, $OR_9$, $N(R_9)_2$, $(CH_2CH_2O)_n$ H, $(CH_2)_mCOOM$ or $(CH_2)_mSO_3M$ is more preferable.

$R_9$ is preferably selected from the group consisting of H, $C_{1-12}$ alkyl, $C_{1-12}$ alkyl substituted phenyl, $C_{1-12}$ alkyl substituted naphthyl, halogen, CN, $(CH_2CH_2O)_nH$, $(CH_2)_mCOOM$ and $(CH_2)_mSO_3M$, and H, $C_{1-6}$ alkyl, $C_{1-6}$ alkyl substituted phenyl, $C_{1-6}$ alkyl substituted naphthyl, halogen, CN, $(CH_2CH_2O)_nH$, $(CH_2)_mCOOM$ or $(CH_2)_mSO_3M$ is more preferable.

It is preferred that n and m are integer from 0 to 12, and more preferably integer from 0 to 6.

The compound in this invention can be directly used for $Hg^{2+}$ detection. Or, in one case, the compound in this invention can be used in a form of derivant of compound I, and the derivant includes but not limited to a conjugate.

The "conjugate" used in this invention is a compound formed by covalently bonding the fluorescence probe of this invention and other molecules.

A composition including the compound of this invention and its conjugate can also be used for $Hg^{2+}$ detection.

Synthesis of Compound

In another aspect, the present invention further provides a method for synthesizing the above-mentioned compound of formula I, which includes the following steps.

(1) synthesis of intermediate II by reacting rhodamine fluorescence dye of formula I' with hydrazine hydrate II: the rhodamine fluorescence dye of formula I' is added into an alcohol solvent and stirred at room temperature so that the rhodamine fluorescence dye is evenly dispersed in the alcohol solvent; hydrazine hydrate in an excessive amount stoichiometrically is added dropwise; after finishing the addition of hydrazine hydrate, the mixture is heated to reflux the solvent and reacted until the reaction solution becomes clear; after the solution is cooled down to room temperature, the solvent is removed by evaporation; acid is added to adjust pH to 2 to 5 and then base solution is added under stirring to adjust pH to 9 to 10 to obtain precipitation; the obtained precipitation is filtered and washed, dried under vacuum and purified by recrystallization or column chromatography.

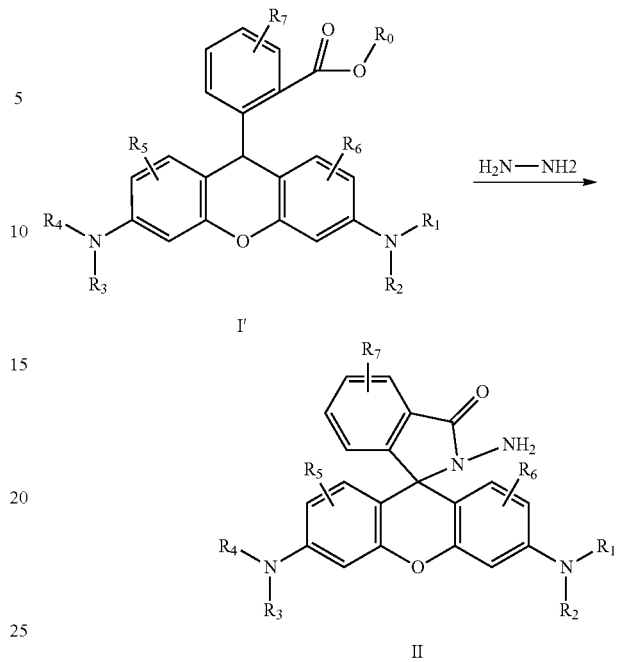

$R_0$ in formula I' is H or $C_{1-6}$ alkyl, and $R_1$, $R_2$, $R_3$, $R_4$, $R_5$, $R_6$ and $R_2$ in formula I' are defined as those in the compound I.

In the reaction, $R_0$ together with adjacent oxygen atom in formula I' is removed to form water or alcohol. $R_0$ is preferably selected from H or $C_{1-4}$ alkyl, and H or $C_{1-2}$ alkyl is more preferable.

The preferable rhodamine dye with lactone-ring is but not limited to rhodamine B, rhodamine 110, rhodamine 6G, rhodamine 3 GB, rhodamine 3GO, rhodamine 123 and so on.

The preferable hydrazine hydrate is 50% or 85% aqueous solution which is commercially available.

The preferable alcohol solvent is but not limited to methanol, ethanol, propanol, and isopropanol. The advantage of these alcohols is low boiling point along with low reflux temperature which is convenient for reflux reaction and solvent removal by evaporation after reaction.

The room temperature is usually −15° C. to 40° C.

The rhodamine dye is usually a solid at room temperature. In order to achieve good reaction effect with hydrazine hydrate, after the rhodamine dye is added into the alcohol solvent, stirring is necessary and stronger stirring is preferred to evenly disperse the rhodamine dye in the alcohol solvent, and it is preferred that the rhodamine dye is dissolved completely in the alcohol solvent.

After the rhodamine dye is dispersed or dissolved in the alcohol solvent, hydrazine hydrate in a state of aqueous solution was added dropwise. An excessive amount of hydrazine hydrate relative to that of the rhodamine dye is preferred for good performance of the reaction, and an excessive amount of 1 to 5 folds is preferable.

After finishing the addition of hydrazine hydrate, the mixture is heated to reflux the solvent and reacted until the reaction solution becomes nearly clear. The preferred reflux time is 1 to 3 h. Then the solution is cooled down to room temperature and the solvent is removed by evaporation. After that, acid (hydrochloric acid is preferred) is added to adjust pH to 2 to 5 and then base solution (aqueous base solution is preferred, and NaOH aqueous solution is more preferred) is added under stirring to adjust pH to 9 to 10 to obtain precipitation. The obtained precipitation is filtered and preferably washed 3 times with deionized water, dried under vacuum and preferably recrystallized with ethanol. The product is characterized through NMR and TOF MS. $^1$H NMR (CDCl$_3$) δ (ppm): 5.85 (s, 4H, NH$_2$) (the shift of H at other position is different according to different rhodamine dye.)

(2) synthesis of intermediate III by reacting the intermediate II obtained in (1) and glyoxal: the intermediate II is added into reactor, and then alcohol solvent, and glyoxal in an excessive amount stoichiometrically are added; the mixture is stirred and reacted for 1 to 3 h at room temperature; the solvent is removed by evaporation, and purification is carried out through recrystallization or column chromatography to obtain the compound of formula III.

aniline compound are added; the mixture is stirred and reacted for 1 to 3 h at room temperature; the solvent is removed by evaporation, and purification is carried out through recrystallization or column chromatography to obtain the compound of formula I.

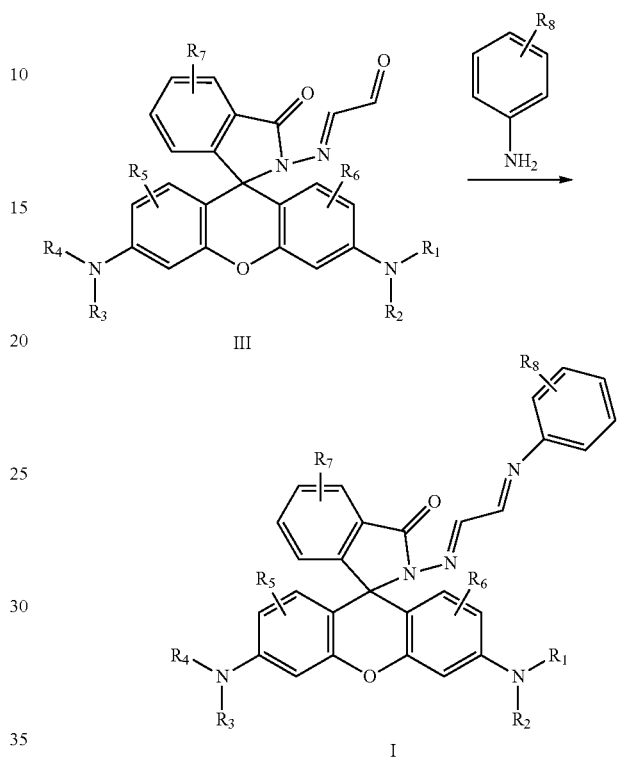

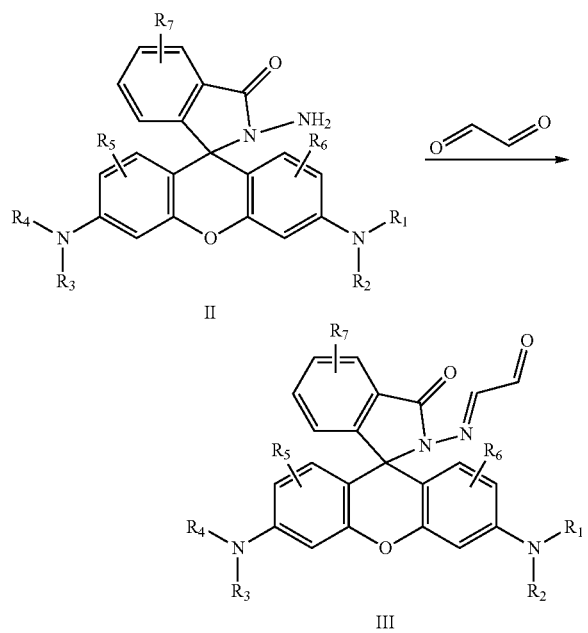

The preferable alcohol solvent is but not limited to methanol, ethanol, propanol, and isopropanol. The alcohol is low boiling point which is convenient for reflux reaction and solvent removal after reaction.

The preferable glyoxal is 40% aqueous solution which is commercially available. An excessive amount of glyoxal relative to that of the intermediate II is preferred for good performance of the reaction, and an excessive amount of 1 to 3 folds is preferable.

The reaction is preferred to be carried out under the protection of inert gas which would give a higher yield.

The room temperature is usually −15° C. to 40° C.

The reaction time is preferred 1.5 to 2.5 h, and 2 h is more preferable.

The solvent is removed by evaporation after the reaction is completed. The product is purified through recrystallization preferably using ethanol. The product is characterized through NMR and TOF MS. $^1$H NMR (CDCl$_3$) δ (ppm): 8.02 (d, 1H, =CH—), 9.42 (d, 1H, O=CH—) (the shift of H at other position is different according to different rhodamine dye.)

(3) synthesis of product compound of formula I by reacting the intermediate III obtained in (2) and R$_8$ substituted aniline compound: the intermediate III compound is added into reactor, and then alcohol solvent and an excessive amount of The preferable alcohol solvent is but not limited to methanol, ethanol, propanol, and isopropanol.

An excessive amount of the aniline compound relative to that of the intermediate III is preferred, and an excessive amount of 1 to 1.5 folds is preferable.

The reaction is preferred to be carried out under the protection of inert gas which would give a higher yield.

The reaction time is preferred 1.5 to 2.5 h, and 2 h is more preferable.

The solvent is removed by evaporation after the reaction is completed. The product is purified through recrystallization preferably using ethanol. The product is characterized through NMR and TOF MS. $^1$H NMR (CDCl$_3$) δ (ppm): 8.01 (d, 1H, —CH=N—), 8.21 (d, 1H, N—N=CH—) (the shift of H at other position is different according to different rhodamine dye.)

$R_1$, $R_2$, $R_3$, $R_4$, $R_5$, $R_6$, $R_7$, $R_8$, $R_9$, m, n, M and $R_{10}$ are defined as those in the compound I.

The obtained fluorescence dye can be separated and purified to achieve needed purity through the common methods in this field.

All the raw materials used in the present invention are commercially available, or can be easily prepared from the known raw materials through known methods in this field.

It should be known that, some of the substituents in the ring in this invention could be introduced by standard aromatic ring substitution reaction or be produced by normal functional group modification, before or after the steps mentioned above, and all of these should be included in the present invention. The reaction and the modification include, for example, introduction of substituent by aromatic ring substitution reaction, reduction of substituent, alkylation of substituent and oxidation of substituent. The reagent and reaction condition used in the process are known in this field. The aromatic ring substitution reaction, for example, includes the introduction of nitro group by concentrated nitric acid, the introduction of acyl group by acyl halide and Lewis acid (e.g. $AlCl_3$) under Friedel Crafts condition, the introduction of alkyl group by alkyl halide and Lewis acid (e.g. $AlCl_3$) under Friedel Crafts condition, and the introduction of halogen group. The modification, for example, includes reduction of nitro group to amino group by catalytic hydrogenation with nickel catalyst or heat-treatment with iron in the presence of HCl, and oxidation of alkylthio group to alkylsulfinyl group or alkyl sulfonyl group.

The conjugate including the compound of formula I in this invention can be synthesized through normal methods in this field.

Composition

In another aspect, the present invention also provides a composition including the compound of formula I or its conjugate. The composition is used for $Hg^{2+}$ detection.

It is preferred that the composition in this invention is in a form of aqueous solution, or is prepared as a solution with water before use.

Applications

In another aspect, the present invention also provides a detection method for $Hg^{2+}$ using the compound of formula I or its conjugate, or using the composition including the compound of formula I or its conjugate.

The fluorescence probe in this invention can be used for $Hg^{2+}$ detection in environment, for example for $Hg^{2+}$ detection in environmental water sample, as well as fluorescence imaging of $Hg^{2+}$ in living cells.

Next, application of probe of the present invention in living cells will be described in detail due to its particularity. In addition, application of probe of the present invention in environmental water sample and sea water sample will be described briefly.

Application in Living Cells:

In order to investigate the ability of probe to track $Hg^{2+}$ in living cells, the following experiment is carried out. A neutral buffer containing the probe is added into cells, and then cells are incubated for 0.5 h in an incubator of 37° C. containing 5% $CO_2$. The obtained cells are fully washed with the buffer or the culture medium and then imaged with fluorescent microscope to give a blank image. On the other hand, $Hg(NO_3)_2$ solution (final concentration is made to 10 μM) is added into the culture containing cells and the probe, and then cells are incubated for 0.5 h in an incubator of 37° C. containing 5% $CO_2$. The obtained cells are washed with the culture medium and then imaged with fluorescent microscope to give an image showing intracellular distribution of $Hg^{2+}$, by which the information about the presence of $Hg^{2+}$ and regional distribution of $Hg^{2+}$ in cells is obtained.

The application method of the compound, its conjugate or its composition of the present invention in environmental water is the common method in this field. Namely, the probe is dissolved in an organic solvent or an organic solvent/water to form a probe solution. Some amount into the environmental water sample containing $Hg^{2+}$ and the mixture is reacted for 10 to 30 min, and then fluorescence is detected.

The application of the fluorescence probe of the present invention in sea water is described below. Namely, the probe is dissolved in an organic solvent or an organic solvent/water to form a probe solution. Some amount of the probe solution is added into the sea water sample containing $Hg^{2+}$ and the mixture is reacted for 10 to 30 min, and then fluorescence is detected.

Results

The probe in this invention shows important application values. Especially, the probe is insensitive to pH, highly sensitive, is not interfered by other metal ions, anions and sulfides, and can realize fluorescence imaging of $Hg^{2+}$ in living cells as well, all of which making the probe as a reagent for $Hg^{2+}$ detection very useful. According to the description above and the common knowledge known by the one skilled in the art, it can be known that the rhodamine-based fluorescence probe of the present invention includes but not limited to the advantages described below.

(1) The probe in this invention has excitation and emission spectra in visible region, high fluorescence quantum yield, low sensitivity to polarity of solvent, and good chemical/photostability.

(2) The probe in this invention is designed based on the mechanism of ring-opening followed by hydrolysis induced by $Hg^{2+}$ coordination which displays large fluorescence enhancement of about 370 folds. The probe shows good selectivity to $Hg^{2+}$ without interference from sulfides such as cysteine, and is insensitive to pH. In the pH range of 4.9 to 7.7, pH change nearly does not affect the fluorescence detection of $Hg^{2+}$.

(3) The probe in this invention can be applied to detect $Hg^{2+}$ of ppb level in environmental water sample like sea water, with good linear relationship between increased fluorescence intensity and $Hg^{2+}$ concentration.

(4) The probe in this invention shows good cell permeability and low toxicity to cells, and can be applied for fluorescence imaging of $Hg^{2+}$ in living cells.

EXAMPLES

Example 1

Synthesis of RHg1:

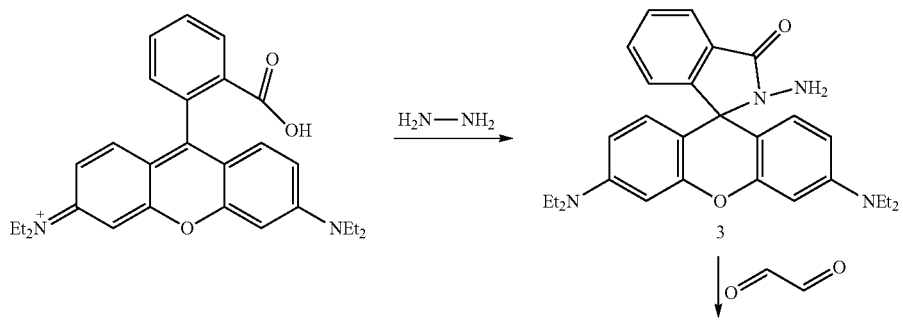

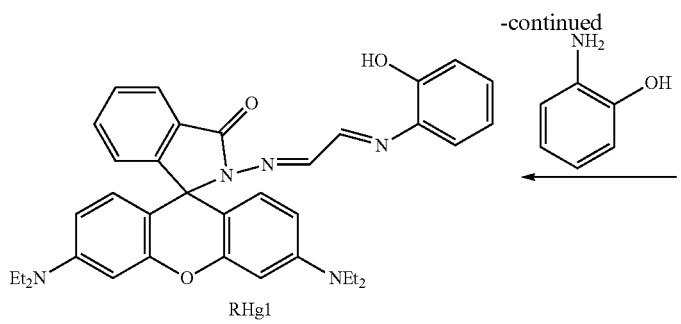
RHg1

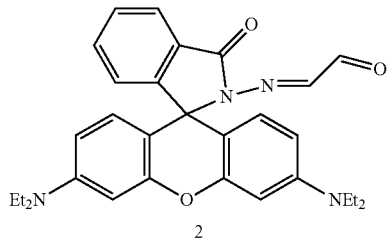
2

(1) The Synthesis of Intermediate 3:

Rhodamine B (1.2 g, 2.5 mmol) was added into a 100 ml single-necked flask containing 30 ml ethanol. The mixture was stirred vigorously at room temperature, followed by dropwise addition of excessive amount of 85% hydrazine hydrate solution (3 ml). After finishing the addition of hydrazine hydrage, the mixture was refluxed for 2 h in air until the solution changed from purple to light brown in color and finally became clear. Then the solution was cooled down to room temperature and ethanol was removed under reduced pressure. After that, 50 ml HCl (1 M) was added to give a red solution, and then 70 ml NaOH aqueous solution (1 M) was added under stirring to adjust pH to 9 to 10 to form a large amount of precipitation. The precipitation was filtered and washed with 15 ml water for three times, then dried under vacuum and purified through column chromatography to produce 0.63 g intermediate 3, yield 55.3%.

(2) The Synthesis of Intermediate 2:

The intermediate 3 (0.46 g, 1.0 mmol) was added into a 100 ml single-necked flask, and then absolute ethanol 30 ml and 40% glyoxal aqueous solution (0.58 g, 4.0 mmol) (excessive in amount) were added. The reaction mixture was stirred for 2 h at room temperature under nitrogen protection, and then the solvent was removed under reduced pressure. The product was purified through silica column chromatography with a mixture of petroleum ether (bp 60 to 90° C.) and ethyl acetate (v/v, 5/1) as elution solution to produce 0.38 g yellow solid RB1 with a yield of 76%. $^1$H NMR (400 MHz CDCl$_3$) δ (ppm): 1.15(t, J=16 Hz, 12H), 3.31(m, J=12 Hz, 8H), 6.25(d, J=8 Hz, 2H), 6.45(m, J=20 Hz, 4H), 7.07(d, J=8 Hz, 1H), 7.45(m, J=8 Hz, 1H), 7.51(t, J=16 Hz, 2H), 8.02 (d, J=8 Hz, 1H), 9.42 (d, J=8 Hz, 1H); $^{13}$C NMR (400 MHz, CDCl$_3$), δ: 12.6, 44.31, 66.04, 98.09, 103.78, 108.17, 123.98, 124.07, 126.58, 127.50, 128.62, 134.97, 141.22, 149.21, 152.64, 152.87, 165.87, 192.49.; TOF MS (ES): m/z Calcd for $C_{30}H_{34}N_4O_3{}^{2+}$: 498.2631, Found: 498.2618.

(3) The Synthesis of RHg1:

The intermediate 2 (0.51 g, 1.0 mmol) was added into a 100 ml single-necked flask, and then absolute 30 ml and 2-aminophenol (0.44 g, 4 mmol) (excessive in amount) were added. The reaction mixture was stirred for 2 h at room temperature under nitrogen protection, and then the solvent was removed under reduced pressure. The product was purified through silica column chromatography with a mixture of petroleum ether (bp 60-90° C.) and ethyl acetate (v/v, 5/1) as elution solution to produce 0.47 g yellow solid RHg1 with a yield of 80%. $^1$H NMR (400 MHz, CDCl$_3$), δ: 1.16(t, J=20 Hz, 12H), 3.33(m, J=20 Hz, 8H), 6.27(d, J=8 Hz, 2H), 6.46(s, 2H), 6.52(d, J=8 Hz, 2H), 6.79(t, J=8 Hz, 1H), 6.91(d, J=8 Hz, 1H), 7.09(d, J=20 Hz, 1H), 7.15(m, J=12 Hz, 2H), 7.20(s, 1H), 7.49(m, J=36 Hz, 2H), 8.02(m, J=20 Hz, 2H), 8.34(d, J=8 Hz, 1H); $^{13}$C NMR (400 MHz, CDCl$_3$), δ: 165.8, 156.0, 152.7, 149.2, 144.9, 134.5, 129.9, 128.4, 127.4, 123.9, 120.1, 115.4, 108.2. 104.7, 98.07, 66.0, 44.3, 12.6; TOF MS (ES): m/z Calcd for $C_{36}H_{37}N_5O_3Na^+$: 610.2794, Found: 610.2797

Example 2

The Selectivity Test of RHg1 to $Hg^{2+}$:

The synthesized compound RHg1 was adopted to test the selectivity to $Hg^{2+}$. RHg1 (5 μM) was added into ethanol aqueous solution (ethanol/water=1/1, v/v) containing metal ion (50 equivalence, except that $Hg^{2+}$ is 15 equivalence), and then the fluorescence spectrum was tested with excitation wavelength of 510 nm and emission wavelength of 580 nm, the result is shown in FIG. 1. From FIG. 1, it can be seen that, RHg1 exhibits good selectivity to $Hg^{2+}$ and large fluorescence and UV-Vis absorption enhancement is induced by $Hg^{2+}$ without the interference from $Na^+$, $K^+$, $Ca^{2+}$, $Mg^{2+}$, $Cu^{2+}$ and so on. The instrument is fluorospectrophotometer, model: LS 55.

Example 3

Figure 3:
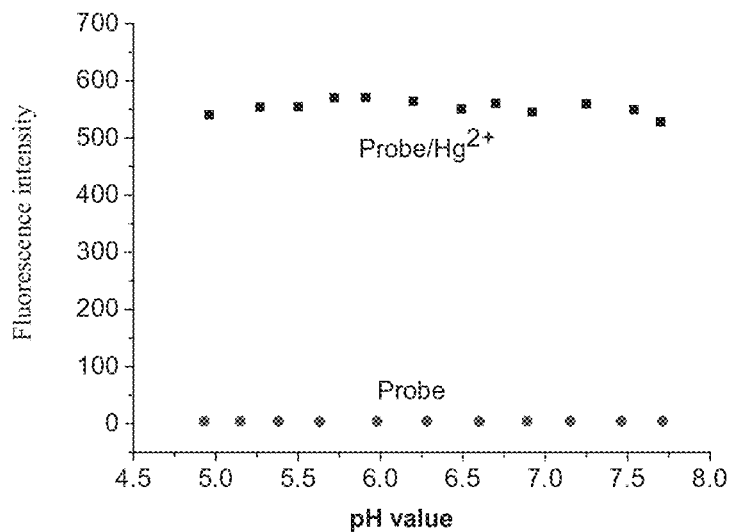
FIG. 3 is fluorescence emission spectra of RHg1 and RHg1-$Hg^{2+}$ coordination compound versus pH. X-axis is pH and Y-axis is fluorescence intensity. Concentration of RHg1 is 5 µM. pH is adjusted with NaOH (1M) and HCl (1M). The instrument is fluorospectrophotometer, model: LS 55.
Figure 4:
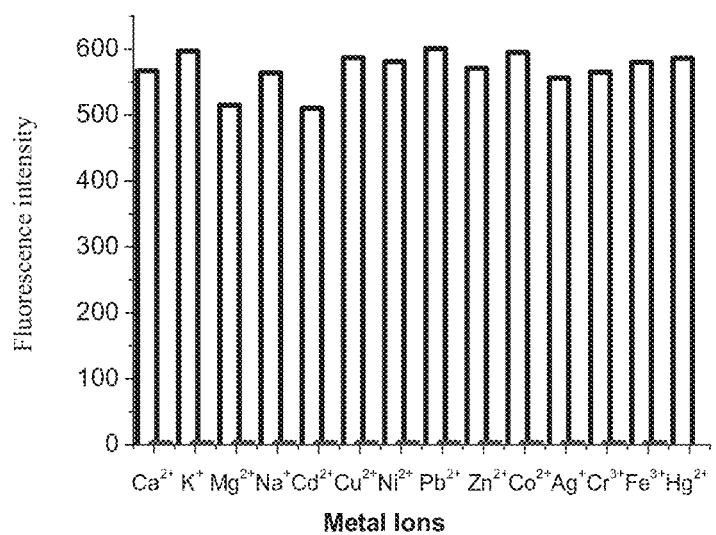
FIG. 4 is interference of metal ions to RHg1-$Hg^{2+}$ coordination compound. Black bar presents fluorescene intensity when the other metal ion except $Hg^{2+}$ is added, and white bar presents fluorescene intensity when the other metal ion plus $Hg^{2+}$ is added. Concentration of RHg1 is 5 µM. X-axis is different metal ions, and concentrations of metal ions are 50 equivalence ($Hg^{2+}$ is 15 equivalence). Y-axis is fluorescence intensity. The instrument is fluorospectrophotometer, model: LS 55.

The Insensitivity of RHg1 Towards pH:

The synthesized compound RHg1 was adopted to test the responses to different pH. The pHs of RHg1 aqueous solution and RHg1/$Hg^{2+}$ aqueous solution (ionic strength of 0.1, respectively) were adjusted to about 4.9, after measurement of fluorescence signal, a base solution was added slowly to adjust pH to 7.7, and the corresponding fluorescence signal change was measure, the results is shown in FIG. 3. From FIG. 3, it can be seen that, the fluorescene emission of RHg1 is nearly not effected by pH change in the range of 4.9 to 7.7. Therefore, RHg1 can be used for $Hg^{2+}$ detection within this pH range. The instrument is fluorospectrophotometer, model: LS 55.

Example 4

Figure 5:
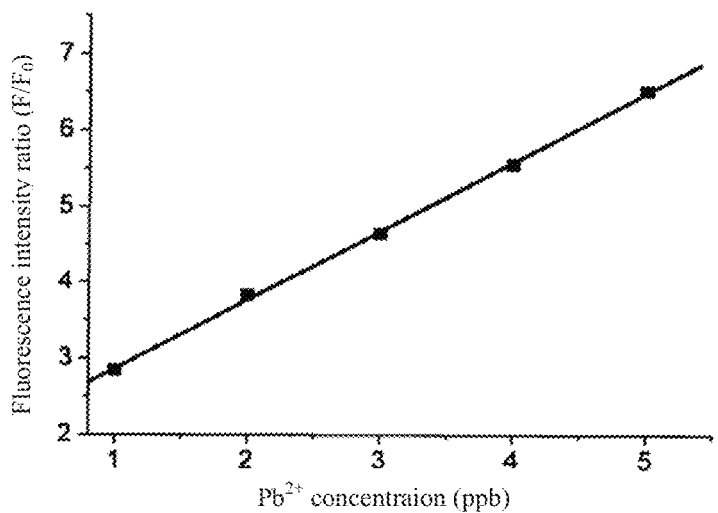
FIG. 5 shows linear relationship of fluorescence intensity of RHg1 versus $Hg^{2+}$ concentration in ppb level in sea water. Concentration of RHg1 is 1 µM. X-axis is $Hg^{2+}$ concentration and Y-axis is ratio of fluorescence intensity. The instrument is fluorospectrophotometer, model: LS 55.

The Sensitivity of RHg1 to $Hg^{2+}$:

The synthesized compound RHg1 was adopted to test the responses to $Hg^{2+}$ in ppb level. RHg1 (1 μM) was added into sea water containing 1-5 ppb $Hg^{2+}$ followed by the measurement of corresponding fluorescence change, the result is shown in FIG. 5. From FIG. 5, it can be seen that, RHg1 displays an evident fluorescence enhancement when $Hg^{2+}$ is in the range of 1 to 5 ppb, and shows good linear relationship between fluorescence intensity and $Hg^{2+}$ concentration. Therefore, RHg1 can be used for $Hg^{2+}$ detection in low concentration. The instrument is fluorospectrophotometer, model: LS 55.

Example 5

Figure 6:
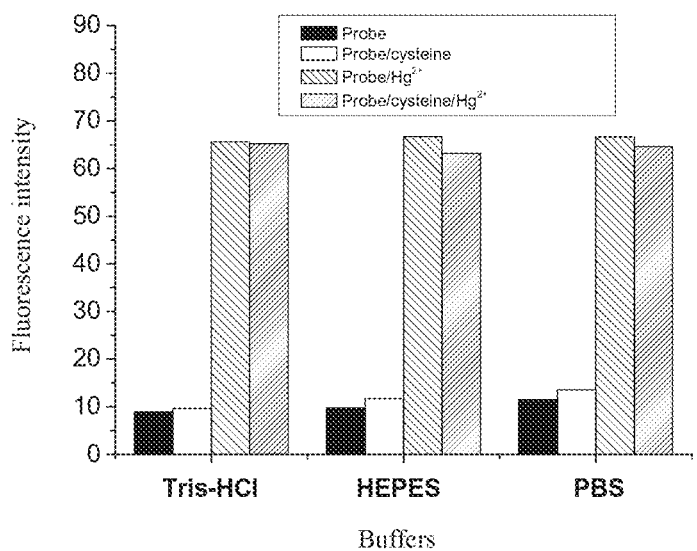
FIG. 6 is effect of L-cysteine on recognition of RHg1 to $Hg^{2+}$ in different buffers. Concentration of RHg1 is 3 µM, and concentration of $Hg^{2+}$ is 200 ppb (1 µM). Four bars represent fluorescence intensity of RHg1, fluorescence intensity of RHg1/L-cysteine, fluorescence intensity of RHg1/$Hg^{2+}$ and fluorescence intensity of RHg1/$Hg^{2+}$/L-cysteine, respectively. X-axis is different buffers: Tris-HCl, HEPES and PBS, and Y-axis is ratio of fluorescence intensity. The instrument is fluorospectrophotometer, model: LS 55.

The Effect of L-cysteine on $Hg^{2+}$ Detection:

The fluorescence of RHg1 (3 μM) was tested first, then the fluorescence of RHg1 after addition of L-cysteine (10 μM) or $Hg^{2+}$ (1 μM) was tested, and finally the fluorescence of the mixed solution containing RHg1, L-cysteine and $Hg^{2+}$ was tested. The result is shown in FIG. 6. From FIG. 6, it can be seen that L-cysteine little effects on $Hg^{2+}$ detection of RHg1. The instrument is Nikon eclipase TE 2000-5.

Example 6

Figure 7:
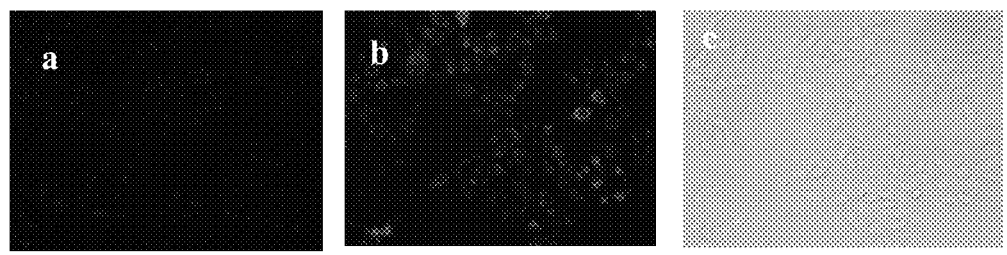
FIG. 7 is fluorescence image of Hela cells incubated with RHg1 at 37° C. for 30 min, and that of Hela cells incubated with RHg1 and $Hg^{2+}$ at 37° C. for 30 min (b). (c) is brightfield transmission image of cells in (b). Concentration of RHg1 is 10 µM and concentration of $Hg^{2+}$ is 10 µM. Excitation light is WB510-570 nm (Nikon eclipase TE 2000-5).
Figure 8:
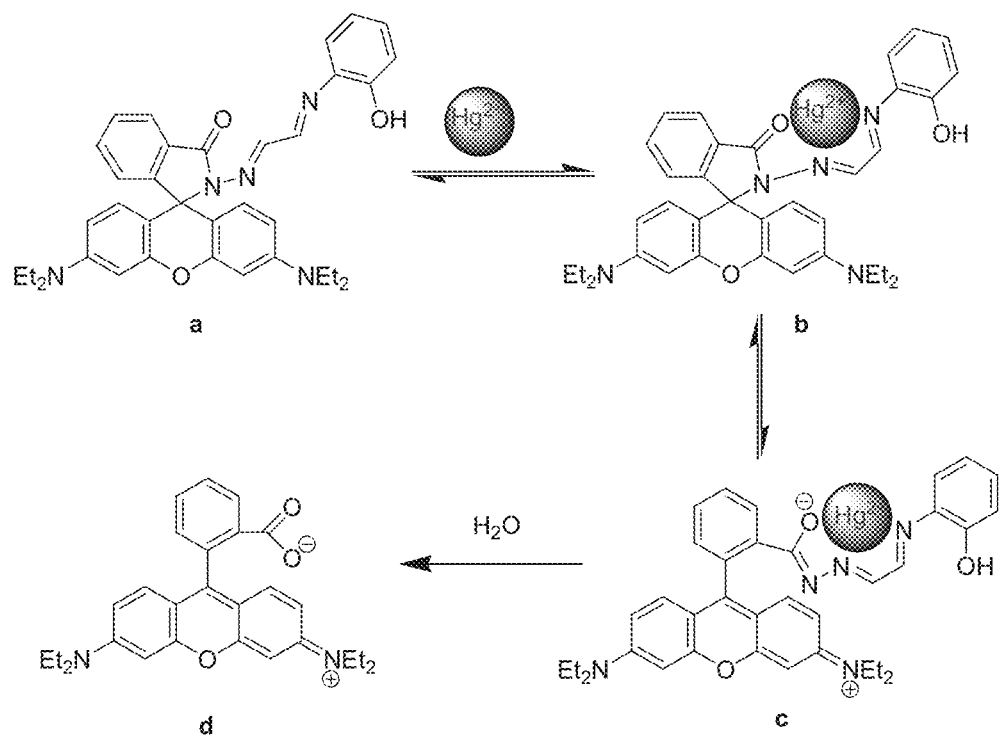
FIG. 8 is detection mechanism of the fluorescence probe in the present invention towards $Hg^{2+}$.
Figure 9:
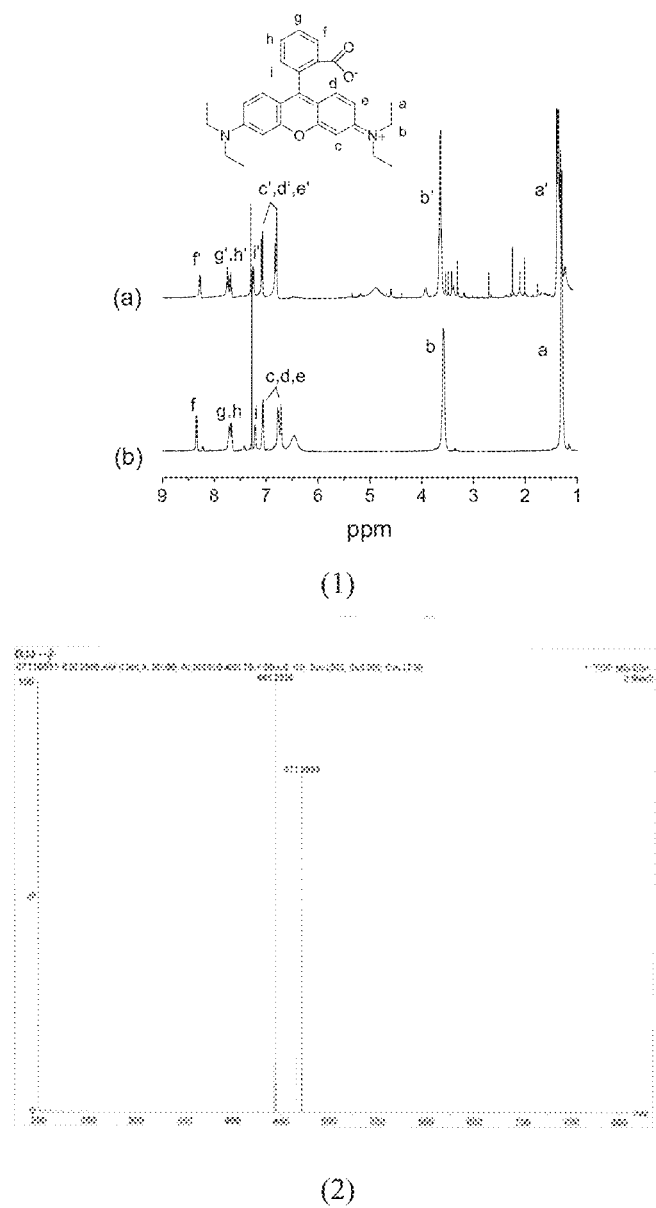
FIGS. 9 (1) and (2) are $^1$H NMR and TOF MS identifying hydrosis product (rhodamine B) of the fluorescene probe in the present invention induced by $Hg^{2+}$, respectively. (1) is $^1$H NMR of the hydrosis product and standard rhodamine B (Acros Organics, 99%), and (2) is TOF MS (ES) of the hydrolysis product: m/z calcd for $C_{28}H_{31}N_2O_3^+$: 443.2335 (molecular weight of rhodamine B), found: 443.2339.

The Fluorescence Imaging to $Hg^{2+}$ in Living Cells:

The synthesized compound RHg1 was added into Hela cells and the cells were cultured at 37° C. for 30 min, the fluorescence of RHg1 in living Hela cells was very weak (FIG. 7(a)). On the other hand, $Hg^{2+}$ was added into the culture containing the Hela cells and the probe and the cells were cultured at 37° C. for 30 min, the fluorescence became very strong in living Hela cells (FIG. 7(b)). Bright-field measurement confirmed that the Hela cells containing RHg1 and $Hg^{2+}$ can be observed throughout the imaging experiment (FIG. 7(c)). The instrument is Nikon eclipase TE 2000-5.

Example 7

The Synthesis of RHg2:

finally became clear. Then the solution was cooled down to room temperature and ethanol was removed under reduced pressure. After that, 50 ml HCl (1 M) was added to give a red solution, and then 70 ml NaOH aqueous solution (1 M) was added under stirring to adjust pH to 9 to 10 to form a large amount of precipitation. The precipitation was filtered and washed with 15 ml water for three times, then dried under vacuum and purified through column chromatography to produce 0.63 g intermediate 3, yield 55.3%. $^1$H NMR (400 MHz CDCl$_3$) δ (ppm): 1.15(t, 12H), 3.31(q, 8H), 3.60 (s, 2H), 6.25(d, J=8 Hz, 2H), 6.45(m, 4H), 7.07(d, J=8 Hz, 1H), 7.45 (m, 1H), 7.47(d, J=16 Hz, 1H), 8.02 (d, J=8 Hz, 1H), 9.42 (d, J=8 Hz, 1H); $^{13}$C NMR (400 MHz, CDCl$_3$), δ: 12.6, 44.5, 66.0, 98.0, 103.8, 108.1, 123.9, 124.0, 127.50, 128.62, 134.97, 147.22, 149.1, 152.6, 165.8; TOF MS (ES): m/z Calcd for $C_{28}H_{32}N_4O_2^+$: 456.2525, Found: 456.2536.

(2) The Synthesis of Intermediate 2:

The intermediate 3 (0.46 g, 1.0 mmol) was added into a 100 ml single-necked flask, and then absolute ethanol 30 ml and 40% glyoxal aqueous solution (0.58 g, 4.0 mmol) (excessive in amount) were added. The reaction mixture was stirred for 2 h at room temperature under nitrogen protection, and then the solvent was removed under reduced pressure. The product was purified through silica column chromatography with a mixture of petroleum ether (bp 60 to 90° C.) and ethyl acetate (v/v, 5/1) as elution solution to produce 0.38 g yellow solid 2 with a yield of 76%. $^1$H NMR (400 MHz CDCl$_3$) δ (ppm):

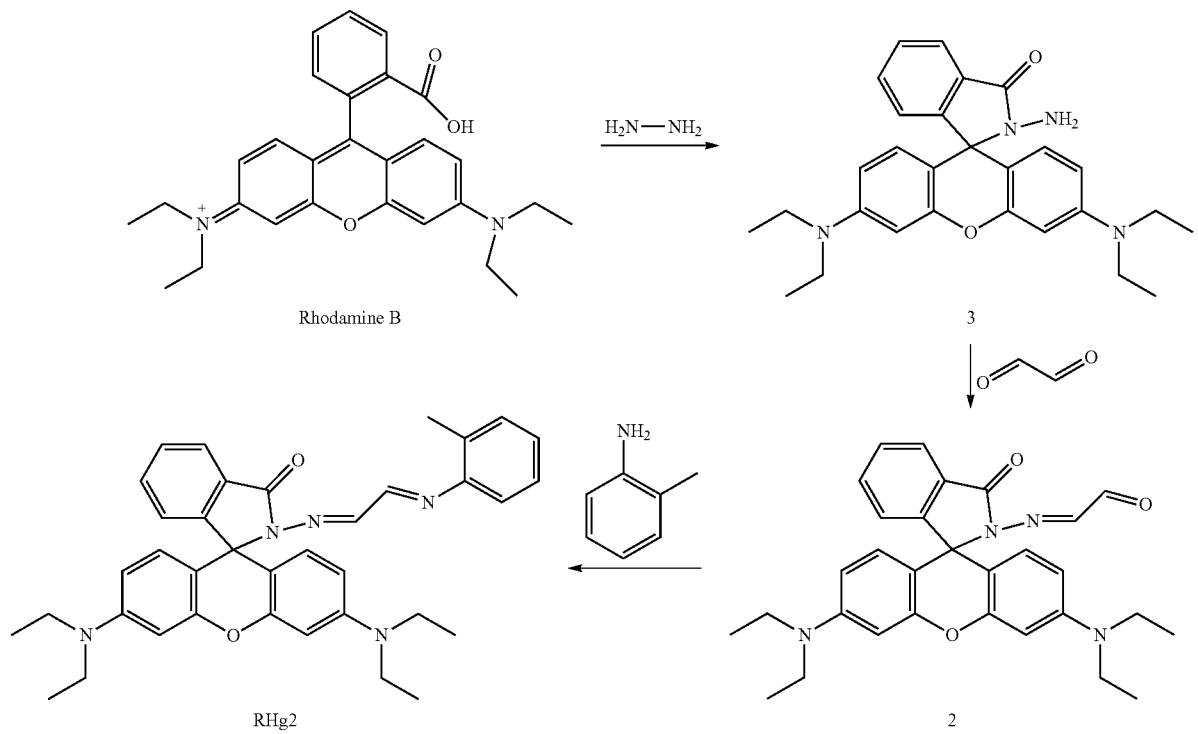

(1) The Synthesis of Intermediate 3:

Rhodamine B (1.2 g, 2.5 mmol) was added into a 100 ml single-necked flask containing 30 ml ethanol. The mixture was stirred vigorously at room temperature, followed by dropwise addition of excessive amount of 85% hydrazine hydrate solution (3 ml). After finishing the addition of hydrazine hydrage, the mixture was refluxed for 2 h in air until the solution changed from purple to light brown in color and 1.15(t, J=16 Hz, 12H), 3.31(m, J=12 Hz, 8H), 6.25(d, J=8 Hz, 2H), 6.45(m, J=20 Hz, 4H), 7.07(d, J=8 Hz, 1H), 7.45(m, J=8 Hz, 1H), 7.51(t, J=16 Hz, 2H), 8.02(d, J=8 Hz, 1H), 9.42(d, J=8 Hz, 1H); $^{13}$C NMR (400 MHz, CDCl$_3$), δ: 12.6, 44.31, 66.04, 98.09, 103.78, 108.17, 123.98, 124.07, 126.58, 127.50, 128.62, 134.97, 141.22, 149.21, 152.64, 152.87, 165.87, 192.49.; TOF MS (ES): m/z Calcd for $C_{30}H_{32}N_4O_3^+$: 498.2631, Found: 498.2618.

(3) The Synthesis of RHg2:

The intermediate 2 (0.51 g, 1.0 mmol) was added into a 100 ml single-necked flask, and then absolute 30 ml and 2-methylphenol (0.44 g, 4 mmol) (excessive in amount) were added. The reaction mixture was stirred for 2 h at room temperature under nitrogen protection, and then the solvent was removed under reduced pressure. The product was purified through silica column chromatography with a mixture of petroleum ether (bp 60-90° C.) and ethyl acetate (v/v, 5/1) as elution solution to produce 0.47 g yellow solid RHg1 with a yield of 80%. $^1$H NMR (400 MHz CDCl$_3$) δ (ppm): 1.16(t, J=20 Hz, 12H), 2.35 (s, 3H), 3.33(m, J=20 Hz, 8H), 6.27(d, J=8 Hz, 2H), 6.46(s, 2H), 6.52(d, J=8 Hz, 2H), 7.09 (m, 3H), 7.25 (m, 2H), 7.47 (m, 2H), 7.95 (d, J=8 Hz, 1H), 8.01 (d, J=8 Hz, 1H), 8.34 (d, J=8 Hz, 1H); $^{13}$C NMR (100 MHz, CDCl$_3$), δ: 12.6, 19.7, 44.3, 68.0, 103.1, 109.9, 114.8, 122.2, 126.4, 127.2, 130.5, 132.7, 139.5, 146.5, 151.8, 163.0; TOF MS (ES): m/z Calcd for $C_{20}H_{16}N_4O_2^+$: 344.1273, Found: 344.1250.

Example 8

Figure 10:
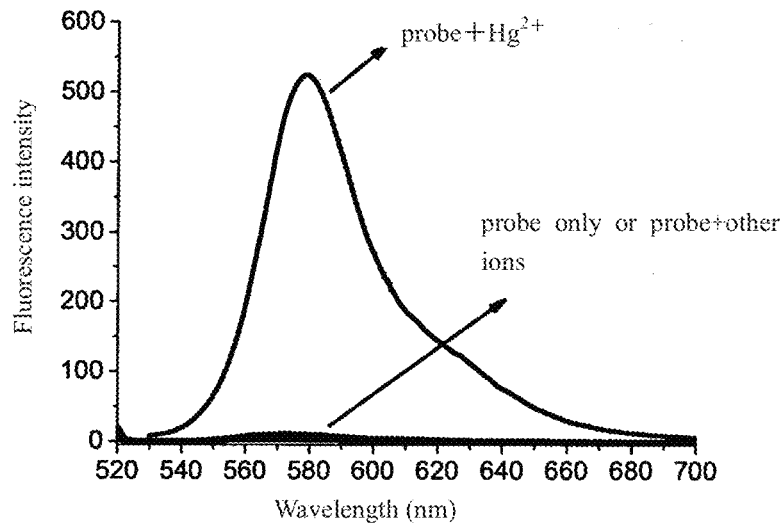
FIG. 10 is fluorescence emission spectra of fluorescence probe RHg2 in Example 7 coordinating $Hg^{2+}$ over other metal ions. Concentration of RHg2 is 5 µM, and concentrations of the metal ions are 50 equivalence ($Hg^{2+}$ is 15 equivalence). X-axis is wavelength (nm) and Y-axis is fluorescence intensity. The instrument is fluorospectrophotometer, model: LS 55.

The Selectivity Test of RHg2 to Hg$^{2+}$:

The synthesized compound RHg2 was adopted to test the selectivity to Hg$^{2+}$. RHg2 (5 μM) was added into ethanol aqueous solution (ethanol/water=1/1, v/v) containing metal ion (50 equivalence, except that Hg$^{2+}$ is 15 equivalence), and then the fluorescence spectrum was tested, the result is shown in FIG. 10. From FIG. 10, it can be seen that, RHg2 exhibits good selectivity to Hg$^{2+}$ and large fluorescence and UV-Vis absorption enhancement is induced by Hg$^{2+}$ without the interference from Na$^+$, K$^+$, Ca$^{2+}$, Mg$^{2+}$, Cu$^{2+}$ and so on. The instrument is fluorospectrophotometer, model: LS 55.

Example 9

The Synthesis of RHg3:

(1) The Synthesis of Intermediate 3:

Rhodamine B (1.2 g, 2.5 mmol) was added into a 100 ml single-necked flask containing 30 ml ethanol. The mixture was stirred vigorously at room temperature, followed by dropwise addition of excessive amount of 85% hydrazine hydrate solution (3 ml). After finishing the addition of hydrazine hydrage, the mixture was refluxed for 2 h in air until the solution changed from purple to light brown in color and finally became clear. Then the solution was cooled down to room temperature and ethanol was removed under reduced pressure. After that, 50 ml HCl (1 M) was added to give a red solution, and then 70 ml NaOH aqueous solution (1 M) was added under stirring to adjust pH to 9 to 10 to form a large amount of precipitation. The precipitation was filtered and washed with 15 ml water for three times, then dried under vacuum and purified through column chromatography to produce 0.63 g intermediate 3, yield 55.3%. $^1$H NMR (400 MHz CDCl$_3$) δ (ppm): 1.15(t, 12H), 3.31(q, 8H), 3.60(s, 2H), 6.25 (d, J=8 Hz, 2H), 6.45(m, 4H), 7.07(d, J=8 Hz, 1H), 7.45(m, 1H), 7.47(d, J=16 Hz, 1H), 8.02 (d, J=8 Hz, 1H), 9.42 (d, J=8 Hz, 1H); $^{13}$C NMR (400 MHz, CDCl$_3$), δ: 12.6, 44.5, 66.0, 98.0, 103.8, 108.1, 123.9, 124.0, 127.50, 128.62, 134.97, 147.22, 149.1, 152.6, 165.8; TOF MS (ES): m/z Calcd for $C_{28}H_{32}N_4O_2^+$: 456.2525, Found: 456.2536.

(2) The Synthesis of Intermediate 2:

The intermediate 3 (0.46 g, 1.0 mmol) was added into a 100 ml single-necked flask, and then absolute ethanol 30 ml and 40% glyoxal aqueous solution (0.58 g, 4.0 mmol) (excessive in amount) were added. The reaction mixture was stirred for 2 h at room temperature under nitrogen protection, and then the solvent was removed under reduced pressure. The product was purified through silica column chromatography with a mixture of petroleum ether (bp 60 to 90° C.) and ethyl acetate (v/v, 5/1) as elution solution to produce 0.38 g yellow solid 2 with a yield of 76%. $^1$H NMR (400 MHz CDCl$_3$) δ (ppm):

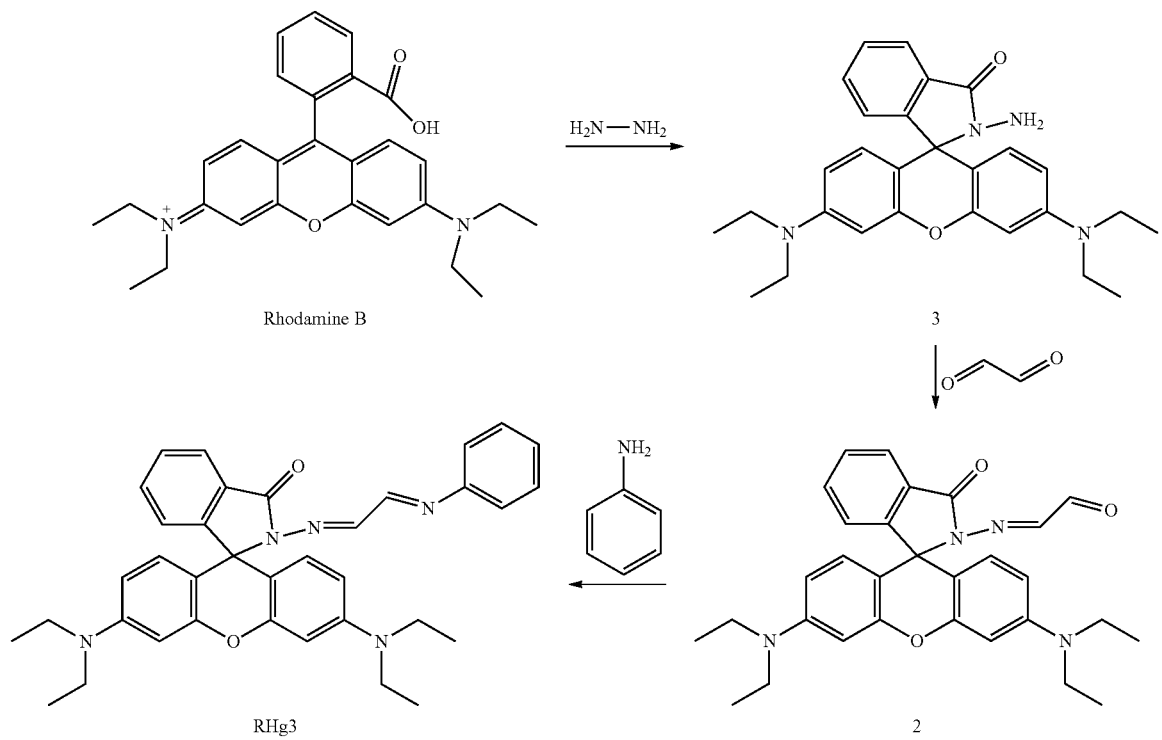

1.15(t, J=16 Hz, 12H), 3.31(m, J=12 Hz, 8H), 6.25(d, J=8 Hz, 2H), 6.45(m, J=20 Hz, 4H), 7.07(d, J=8 Hz, 1H), 7.45(m, J=8 Hz, 1H), 7.51(t, J=16 Hz, 2H), 8.02 (d, J=8 Hz, 1H), 9.42 (d, J=8 Hz, 1H); $^{13}$C NMR (400 MHz, CDCl$_3$), δ: 12.6, 44.31, 66.04, 98.09, 103.78, 108.17, 123.98, 124.07, 126.58, 127.50, 128.62, 134.97, 141.22, 149.21, 152.64, 152.87, 165.87, 192.49.; TOF MS (ES): m/z Calcd for $C_{30}H_{32}N_4O_3^+$: 498.2631, Found: 498.2618.

(3) The Synthesis of RHg3

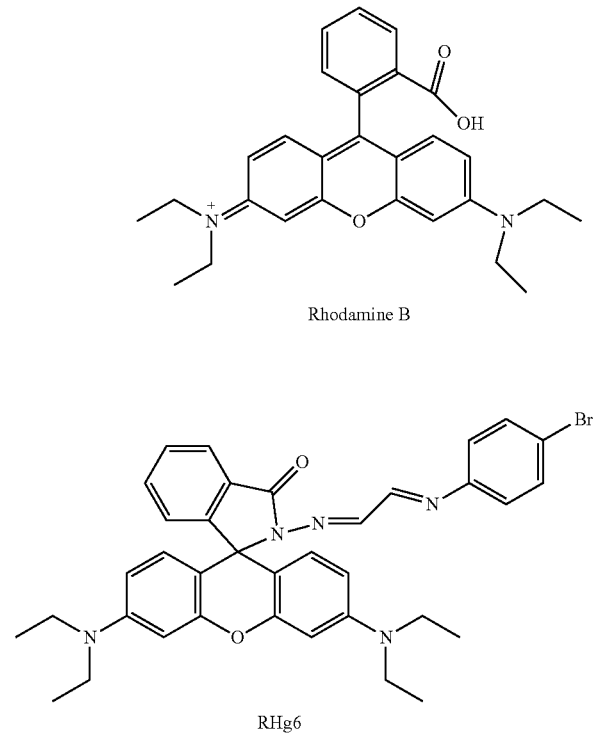
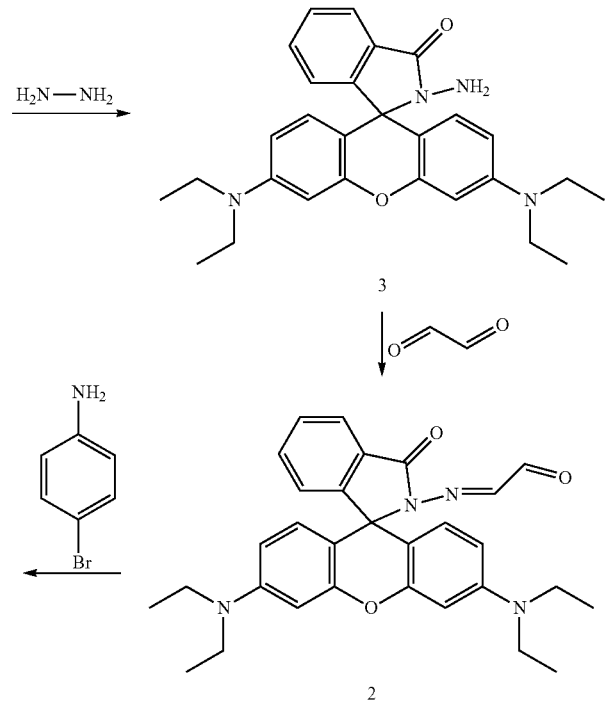

The intermediate 2 (0.51 g, 1.0 mmol) was added into a 100 ml single-necked flask, and then absolute 30 ml and aniline (0.44 g, 4 mmol) (excessive in amount) were added. The reaction mixture was stirred for 2 h at room temperature under nitrogen protection, and then the solvent was removed under reduced pressure. The product was purified through silica column chromatography with a mixture of petroleum ether (bp 60-90° C.) and ethyl acetate (v/v, 5/1) as elution solution to produce 0.47 g yellow solid RHg3 with a yield of 80%. $^1$H NMR (400 MHz CDCl$_3$) δ (ppm): 1.16(t, J=20 Hz, 12H), 3.33(m, J=20 Hz, 8H), 6.27(d, J=8 Hz, 2H), 6.46(s, 2H), 6.52(d, J=8 Hz, 2H), 7.09(m, 2H), 7.31(m, 4H), 7.47(m, 2H), 7.95 (d, J=8 Hz, 1H), 8.01 (d, J=8 Hz, 1H), 8.34 (d, J=8 Hz, 1H); $^{13}$C NMR (100 MHz, CDCl$_3$), δ: 12.6, 44.3, 68.0, 103.1, 109.9, 114.8, 122.3, 128.0, 130.1, 132.7, 139.5, 145.6, 147.5, 149.0, 151.8, 163.0, 168.0; TOF MS (ES): m/z Calcd for $C_{20}H_{16}N_4O_2^+$: 344.1273, Found: 344.1250.

Example 10

Figure 11:
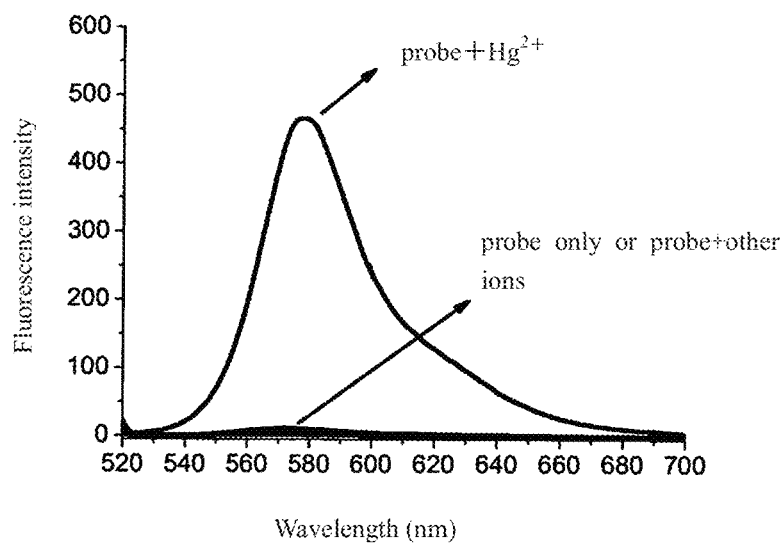
FIG. 11 is fluorescence emission spectra of fluorescence probe RHg3 coordinating $Hg^{2+}$ over other metal ions. Concentration of RHg3 is 5 µM, and concentrations of the metal ions are 50 equivalence ($Hg^{2+}$ is 15 equivalence). X-axis is wavelength (nm) and Y-axis is fluorescence intensity. The instrument is fluorospectrophotometer, model: LS 55.

The Selectivity Test of RHg3 to Hg$^{2+}$:

The synthesized compound RHg3 was adopted to test the selectivity to Hg$^{2+}$. RHg3 (5 μM) was added into ethanol aqueous solution (ethanol/water=1/1, v/v) containing metal ion (50 equivalence, except that Hg$^{2+}$ is 15 equivalence), and then the fluorescence spectrum was tested, the result is shown in FIG. 11. From FIG. 11, it can be seen that, RHg3 exhibits good selectivity to Hg$^{2+}$ and large fluorescence and UV-Vis absorption enhancement is induced by Hg$^{2+}$ without the interference from Na$^+$, K$^+$, Ca$^{2+}$, Mg$^{2+}$, Cu$^{2+}$ and so on. The instrument is fluorospectrophotometer, model: LS 55.

Example 11

The Synthesis of RHg4:

(1) The Synthesis of Intermediate 3:

Rhodamine B (1.2 g, 2.5 mmol) was added into a 100 ml single-necked flask containing 30 ml ethanol. The mixture was stirred vigorously at room temperature, followed by dropwise addition of excessive amount of 85% hydrazine hydrate solution (3 ml). After finishing the addition of hydrazine hydrage, the mixture was refluxed for 2 h in air until the solution changed from purple to light brown in color and finally became clear. Then the solution was cooled down to room temperature and ethanol was removed under reduced pressure. After that, 50 ml HCl (1 M) was added to give a red solution, and then 70 ml NaOH aqueous solution (1 M) was added under stirring to adjust pH to 9 to 10 to form a large amount of precipitation. The precipitation was filtered and washed with 15 ml water for three times, then dried under vacuum and purified through column chromatography to produce 0.63 g intermediate 3, yield 55.3%. $^1$H NMR (400 MHz CDCl$_3$) δ (ppm): 1.15(t, 12H), 3.31(q, 8H), 3.60 (s, 2H), 6.25(d, J=8 Hz, 2H), 6.45(m, 4H), 7.07(d, J=8 Hz, 1H), 7.45 (m, 1H), 7.47(d, J=16 Hz, 1H), 8.02(d, J=8 Hz, 1H), 9.42(d, J=8 Hz, 1H); $^{13}$C NMR (400 MHz, CDCl$_3$), δ: 12.6, 44.5, 66.0, 98.0, 103.8, 108.1, 123.9, 124.0, 127.50, 128.62, 134.97, 147.22, 149.1, 152.6, 165.8; TOF MS (ES): m/z Calcd for $C_{28}H_{32}N_4O_2^+$: 456.2525, Found: 456.2536.

(2) The Synthesis of Intermediate 2:

The intermediate 3 (0.46 g, 1.0 mmol) was added into a 100 ml single-necked flask, and then absolute ethanol 30 ml and 40% glyoxal aqueous solution (0.58 g, 4.0 mmol) (excessive in amount) were added. The reaction mixture was stirred for 2 h at room temperature under nitrogen protection, and then the solvent was removed under reduced pressure. The product was purified through silica column chromatography with a mixture of petroleum ether (bp 60 to 90° C.) and ethyl acetate (v/v, 5/1) as elution solution to produce 0.38 g yellow solid 2 with a yield of 76%. $^1$H NMR (400 MHz CDCl$_3$) δ (ppm): 1.15(t, J=16 Hz, 12H), 3.31(m, J=12 Hz, 8H), 6.25(d, J=8 Hz, 2H), 6.45(m, J=20 Hz, 4H), 7.07(d, J=8 Hz, 1H), 7.45(m, J=8 Hz, 1H), 7.51(t, J=16 Hz, 2H), 8.02(d, J=8 Hz, 1H), 9.42(d, J=8 Hz, 1H); $^{13}$C NMR (400 MHz, CDCl$_3$), δ: 12.6, 44.31, 66.04, 98.09, 103.78, 108.17, 123.98, 124.07, 126.58, 127.50, 128.62, 134.97, 141.22, 149.21, 152.64, 152.87, 165.87, 192.49.; TOF MS (ES): m/z Calcd for $C_{30}H_{32}N_4O_3^+$: 498.2631, Found: 498.2618.

(3) The Synthesis of RHg4:

The intermediate 2 (0.51 g, 1.0 mmol) was added into a 100 ml single-necked flask, and then absolute 30 ml and 4-bromoaniline (0.68 g, 4 mmol) (excessive in amount) were added. The reaction mixture was stirred for 2 h at room temperature under nitrogen protection, and then the solvent was removed under reduced pressure. The product was purified through silica column chromatography with a mixture of petroleum ether (bp 60-90° C.) and ethyl acetate (v/v, 5/1) as elution solution to produce 0.49 g yellow solid RHg4 with a yield of 75%. $^1$H NMR (400 MHz CDCl$_3$) δ (ppm): 1.16(t, J=20 Hz, 12H), 3.33(m, J=20 Hz, 8H), 6.27(d, J=8 Hz, 2H), 6.46 (s, 2H), 6.52(d, J=8 Hz, 2H), 7.09(m, 3H), 7.47(m, 4H), 7.95(d, J=8 Hz, 1H), 8.01(d, J=8 Hz, 1H), 8.34(d, J=8 Hz, 1H); $^{13}$C NMR (100 MHz, CDCl$_3$), δ: 12.6, 44.3, 68.0, 103.1, 114.8, 121.3, 124.5, 126.4, 128.3, 131.3, 132.9, 139.5, 145.6, 147.5, 148.0, 151.8, 163.0, 168.0; TOF MS (ES): m/z Calcd for $C_{20}H_{16}N_4O_2^+$: 344.1273, Found: 344.1250.

Example 12

Figure 12:
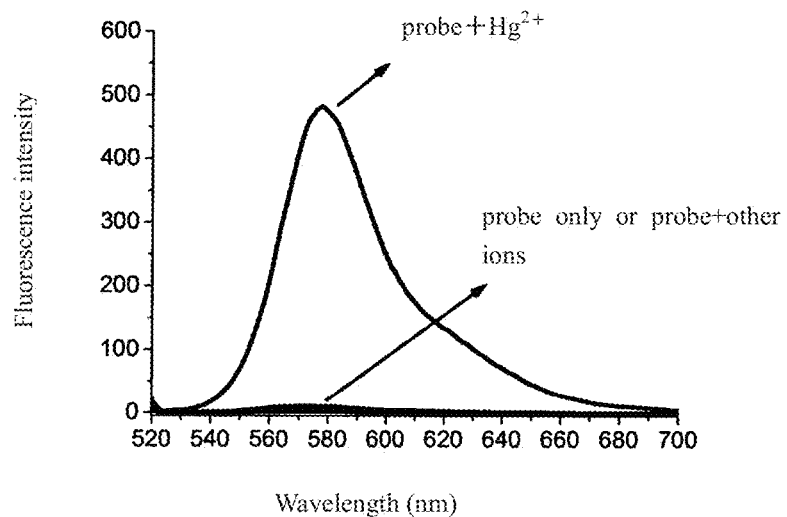
FIG. 12 is fluorescence emission spectra of fluorescence probe RHg4 coordinating $Hg^{2+}$ over other metal ions. Concentration of RHg4 is 5 µM, and concentrations of the metal ions are 50 equivalence ($Hg^{2+}$ is 15 equivalence). X-axis is wavelength (nm) and Y-axis is fluorescence intensity. The instrument is fluorospectrophotometer, model: LS 55.

The Selectivity Test of RHg4 to Hg$^{2+}$:

The synthesized compound RHg4 was adopted to test the selectivity to Hg$^{2+}$. RHg4 (5 μM) was added into ethanol aqueous solution (ethanol/water=1/1, v/v) containing metal ion (50 equivalence, except that Hg$^{2+}$ is 15 equivalence), and then the fluorescence spectrum was tested, the result is shown in FIG. 12. From FIG. 12, it can be seen that, RHg4 exhibits good selectivity to Hg$^{2+}$ and large fluorescence and UV-Vis absorption enhancement is induced by Hg$^{2+}$ without the interference from Na$^+$, K$^+$, Ca$^{2+}$, Mg$^{2+}$, Cu$^{2+}$ and so on. The instrument is fluorospectrophotometer, model: LS 55.

Example 13

The Synthesis of RHg5:

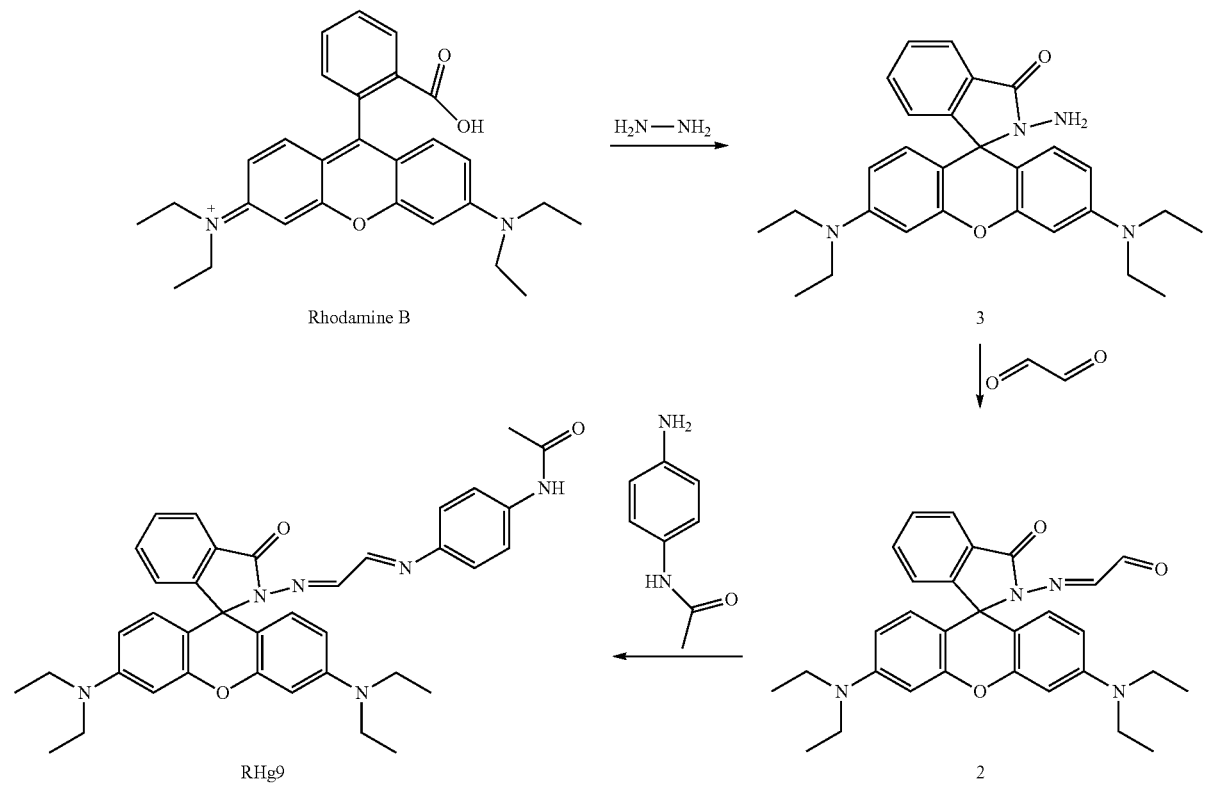

(1) The Synthesis of Intermediate 3:

Rhodamine B (1.2 g, 2.5 mmol) was added into a 100 ml single-necked flask containing 30 ml ethanol. The mixture was stirred vigorously at room temperature, followed by dropwise addition of excessive amount of 85% hydrazine hydrate solution (3 ml). After finishing the addition of hydrazine hydrage, the mixture was refluxed for 2 h in air until the solution changed from purple to light brown in color and finally became clear. Then the solution was cooled down to room temperature and ethanol was removed under reduced pressure. After that, 50 ml HCl (1 M) was added to give a red solution, and then 70 ml NaOH aqueous solution (1 M) was added under stirring to adjust pH to 9 to 10 to form a large amount of precipitation. The precipitation was filtered and washed with 15 ml water for three times, then dried under vacuum and purified through column chromatography to produce 0.63 g intermediate 3, yield 55.3%. $^1$H NMR (400 MHz CDCl$_3$) δ (ppm): 1.15(t, 12H), 3.31(q, 8H), 3.60 (s, 2H), 6.25(d, J=8 Hz, 2H), 6.45(m, 4H), 7.07(d, J=8 Hz, 1H), 7.45 (m, 1H), 7.47(d, J=16 Hz, 1H), 8.02 (d, J=8 Hz, 1H), 9.42(d, J=8 Hz, 1H); $^{13}$C NMR (400 MHz, CDCl$_3$), δ: 12.6, 44.5, 66.0, 98.0, 103.8, 108.1, 123.9, 124.0, 127.50, 128.62, 134.97, 147.22, 149.1, 152.6, 165.8; TOF MS (ES): m/z Calcd for $C_{28}H_{32}N_4O_2^+$: 456.2525, Found: 456.2536.

(2) The Synthesis of Intermediate 2:

The intermediate 3 (0.46 g, 1.0 mmol) was added into a 100 ml single-necked flask, and then absolute ethanol 30 ml and 40% glyoxal aqueous solution (0.58 g, 4.0 mmol) (excessive in amount) were added. The reaction mixture was stirred for 2 h at room temperature under nitrogen protection, and then the solvent was removed under reduced pressure. The product was purified through silica column chromatography with a mixture of petroleum ether (bp 60 to 90° C.) and ethyl acetate (v/v, 5/1) as elution solution to produce 0.38 g yellow solid 2 with a yield of 76%. $^1$H NMR (400 MHz CDCl$_3$) δ (ppm): 1.15(t, J=16 Hz, 12H), 3.31(m, J=12 Hz, 8H), 6.25(d, J=8 Hz, 2H), 6.45(m, J=20 Hz, 4H), 7.07(d, J=8 Hz, 1H), 7.45(m, J=8 Hz, 1H), 7.51(t, J=16 Hz, 2H), 8.02 (d, J=8 Hz, 1H), 9.42 (d, J=8 Hz, 1H); $^{13}$C NMR (400 MHz, CDCl$_3$), δ: 12.6, 44.31, 66.04, 98.09, 103.78, 108.17, 123.98, 124.07, 126.58, 127.50, 128.62, 134.97, 141.22, 149.21, 152.64, 152.87, 165.87, 192.49.; TOF MS (ES): m/z Calcd for $C_{30}H_{32}N_4O_3^+$: 498.2631, Found: 498.2618.

(3) The Synthesis of RHg5:

The intermediate 2 (0.50 g, 1.0 mmol) was added into a 100 ml single-necked flask, and then absolute 30 ml and N-(4-aminophenyl)acetamide (0.6 g, 4 mmol) (excessive in amount) were added. The reaction mixture was stirred for 2 h at room temperature under nitrogen protection, and then the solvent was removed under reduced pressure. The product was purified through silica column chromatography with a mixture of petroleum ether (bp 60-90° C.) and ethyl acetate (v/v, 5/1) as elution solution to produce 0.46 g yellow solid RHg5 with a yield of 73%. $^1$H NMR (400 MHz CDCl$_3$) δ (ppm): 1.16(t, J=20 Hz, 12H), 2.03(s, 3H), 3.33(m, J=20 Hz, 8H), 6.27(d, J=8 Hz, 2H), 6.46(s, 2H), 6.52(d, J=8 Hz, 2H), 7.09(s, 3H), 7.47(m, 4H), 7.95(d, J=8 Hz, 1H), 8.01(d, J=8 Hz, 1H), 8.34(d, J=8 Hz, 1H), 10.01(s, 1H); $^{13}$C NMR (100 MHz, CDCl$_3$), δ: 12.6, 22.9, 44.3, 68.1, 103.1, 109.9, 114.3, 122.9, 126.4, 128.3, 132.7, 136.9, 139.5, 144.6, 147.5, 151.8, 163.0, 168.9; TOF MS (ES): m/z Calcd for $C_{20}H_{16}N_4O_2^+$: 344.1273, Found: 344.1250.

Example 14

Figure 13:
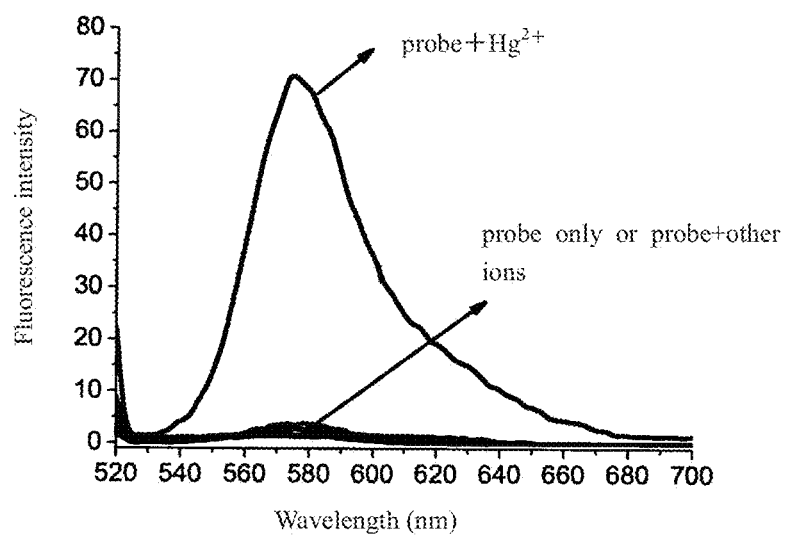
FIG. 13 is fluorescence emission spectra of fluorescence probe RHg5 coordinating $Hg^{2+}$ over other metal ions. Concentration of RHg5 is 5 µM, and concentrations of the metal ions are 50 equivalence ($Hg^{2+}$ is 15 equivalence). X-axis is wavelength (nm) and Y-axis is fluorescence intensity. The instrument is fluorospectrophotometer, model: LS 55.

The Selectivity Test of RHg5 to $Hg^{2+}$:

The synthesized compound RHg5 was adopted to test the selectivity to $Hg^{2+}$. RHg5 (5 μM) was added into ethanol aqueous solution (ethanol/water=1/1, v/v) containing metal ion (50 equivalence, except that $Hg^{2+}$ is 15 equivalence), and then the fluorescence spectrum was tested, the result is shown in FIG. 13. From FIG. 13, it can be seen that, RHg5 exhibits good selectivity to $Hg^{2+}$ and large fluorescence and UV-Vis absorption enhancement is induced by $Hg^{2+}$ without the interference from $Na^+$, $K^+$, $Ca^{2+}$, $Mg^{2+}$, $Cu^{2+}$ and so on. The instrument is fluorospectrophotometer, model: LS 55.

Example 15

The Synthesis of RHg6:

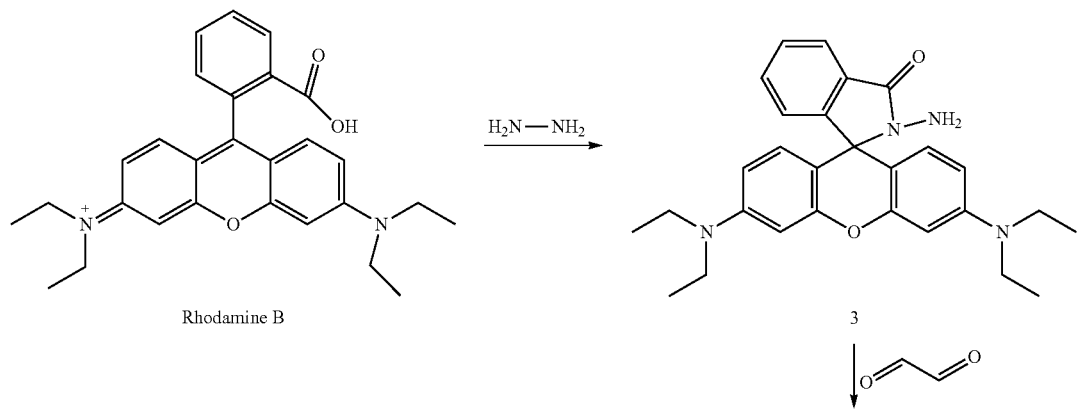

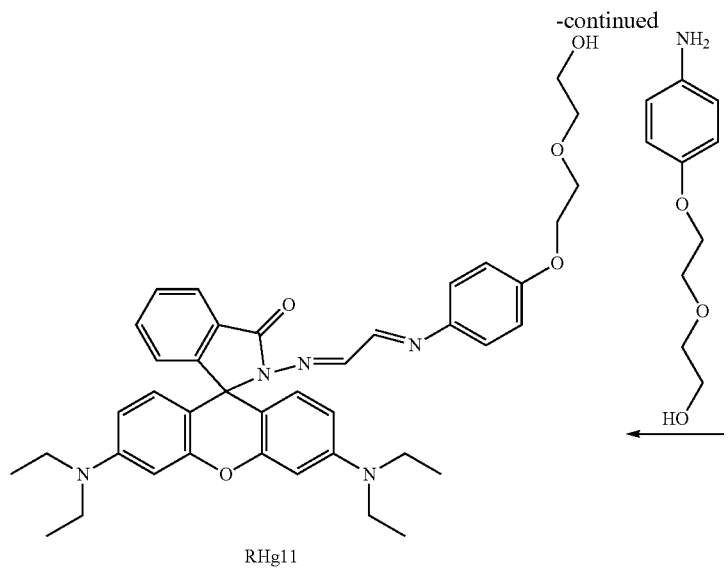

RHg11

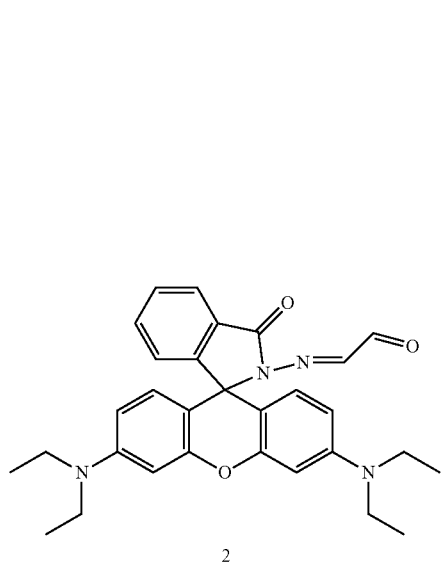

2

(1) The Synthesis of Intermediate 3:

Rhodamine B (1.2 g, 2.5 mmol) was added into a 100 ml single-necked flask containing 30 ml ethanol. The mixture was stirred vigorously at room temperature, followed by dropwise addition of excessive amount of 85% hydrazine hydrate solution (3 ml). After finishing the addition of hydrazine hydrage, the mixture was refluxed for 2 h in air until the solution changed from purple to light brown in color and finally became clear. Then the solution was cooled down to room temperature and ethanol was removed under reduced pressure. After that, 50 ml HCl (1 M) was added to give a red solution, and then 70 ml NaOH aqueous solution (1 M) was added under stirring to adjust pH to 9 to 10 to form a large amount of precipitation. The precipitation was filtered and washed with 15 ml water for three times, then dried under vacuum and purified through column chromatography to produce 0.63 g intermediate 3, yield 55.3%. $^1$H NMR (400 MHz CDCl$_3$) δ (ppm): 1.15(t, 12H), 3.31(q, 8H), 3.60 (s, 2H), 6.25(d, J=8 Hz, 2H), 6.45(m, 4H), 7.07(d, J=8 Hz, 1H), 7.45 (m, 1H), 7.47(d, J=16 Hz, 1H), 8.02(d, J=8 Hz, 1H), 9.42(d, J=8 Hz, 1H); $^{13}$C NMR (400 MHz, CDCl$_3$), δ: 12.6, 44.5, 66.0, 98.0, 103.8, 108.1, 123.9, 124.0, 127.50, 128.62, 134.97, 147.22, 149.1, 152.6, 165.8; TOF MS (ES): m/z Calcd for C$_{28}$H$_{32}$N$_4$O$_2$$^+$: 456.2525, Found: 456.2536.

(2) The Synthesis of Intermediate 2:

The intermediate 3 (0.46 g, 1.0 mmol) was added into a 100 ml single-necked flask, and then absolute ethanol 30 ml and 40% glyoxal aqueous solution (0.58 g, 4.0 mmol) (excessive in amount) were added. The reaction mixture was stirred for 2 h at room temperature under nitrogen protection, and then the solvent was removed under reduced pressure. The product was purified through silica column chromatography with a mixture of petroleum ether (bp 60 to 90° C.) and ethyl acetate (v/v, 5/1) as elution solution to produce 0.38 g yellow solid 2 with a yield of 76%. $^1$H NMR (400 MHz CDCl$_3$) δ (ppm): 1.15(t, J=16 Hz, 12H), 3.31(m, J=12 Hz, 8H), 6.25(d, J=8 Hz, 2H), 6.45(m, J=20 Hz, 4H), 7.07(d, J=8 Hz, 1H), 7.45(m, J=8 Hz, 1H), 7.51(t, J=16 Hz, 2H), 8.02(d, J=8 Hz, 1H), 9.42(d, J=8 Hz, 1H); $^{13}$C NMR (400 MHz, CDCl$_3$), δ: 12.6, 44.31, 66.04, 98.09, 103.78, 108.17, 123.98, 124.07, 126.58, 127.50, 128.62, 134.97, 141.22, 149.21, 152.64, 152.87, 165.87, 192.49; TOF MS (ES): m/z Calcd for C$_{30}$H$_{32}$N$_4$O$_3$$^+$: 498.2631, Found: 498.2618.

(3) the Synthesis of RHg6:

The intermediate 2 (0.50 g, 1.0 mmol) was added into a 100 ml single-necked flask, and then absolute 30 ml and 2-(2-(4-aminophenoxy)ethoxy)ethanol (0.79 g, 4 mmol) (excessive in amount) were added. The reaction mixture was stirred for 2 h at room temperature under nitrogen protection, and then the solvent was removed under reduced pressure. The product was purified through silica column chromatography with a mixture of petroleum ether (bp 60-90° C.) and ethyl acetate (v/v, 5/1) as elution solution to produce 0.54 g yellow solid RHg6 with a yield of 80%. $^1$H NMR (400 MHz CDCl$_3$) δ (ppm): 1.16(t, J=20 Hz, 12H), 3.33(m, J=20 Hz, 8H), 6.27(d, J=8 Hz, 2H), 6.46(s, 2H), 6.52(d, J=8 Hz, 2H), 7.10(d, J=8 Hz, 1H), 7.45(d, J=8 Hz, 1H), 7.48(t, 2H), 8.02(d, J=8 Hz, 1H), 9.42(d, J=8 Hz, 1H); $^{13}$C NMR (100 MHz, CDCl$_3$), δ: 12.6, 44.3, 66.04, 98.09, 103.78, 108.17, 123.98, 124.07, 126.58, 128.62, 134.97, 141.22, 149.21, 152.64, 152.87, 165.87, 192.49; TOF MS (ES): m/z Calcd for C$_{20}$H$_{16}$N$_4$O$_2$$^+$: 384.1222, Found: 384.1235.

Example 16

Figure 14:
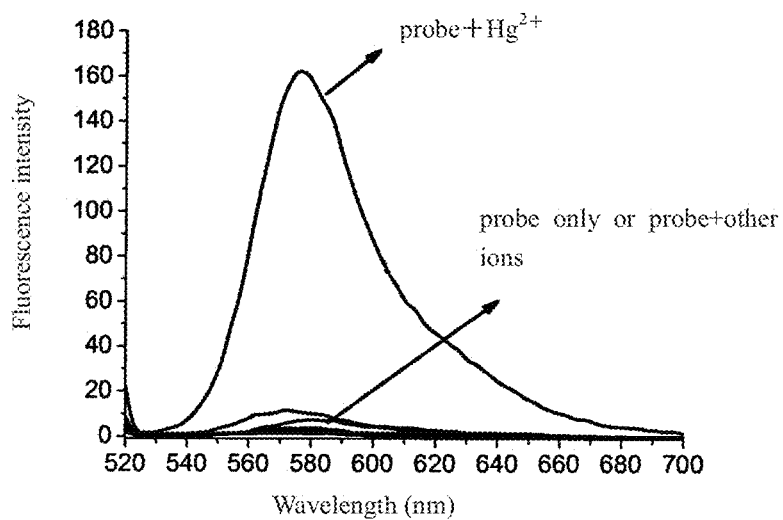
FIG. 14 is fluorescence emission spectra of fluorescence probe RHg6 coordinating $Hg^{2+}$ over other metal ions. Concentration of RHg6 is 5 µM, and concentrations of the metal ions are 50 equivalence ($Hg^{2+}$ is 15 equivalence). X-axis is wavelength (nm) and Y-axis is fluorescence intensity. The instrument is fluorospectrophotometer, model: LS 55.

The Selectivity Test of RHg6 to Hg$^{2+}$:

The synthesized compound RHg6 was adopted to test the selectivity to Hg$^{2+}$. RHg6 (5 μM) was added into ethanol aqueous solution (ethanol/water=1/1, v/v) containing metal ion (50 equivalence, except that Hg$^{2+}$ is 15 equivalence), and then the fluorescence spectrum was tested, the result is shown in FIG. 14. From FIG. 14, it can be seen that, RHg6 exhibits good selectivity to Hg$^{2+}$ and large fluorescence and UV-Vis absorption enhancement is induced by Hg$^{2+}$ without the interference from Na$^+$, K$^+$, Ca$^{2+}$, Mg$^{2+}$, Cu$^{2+}$ and so on. The instrument is fluorospectrophotometer, model: LS 55.

Example 17

The Synthesis of RHg7:

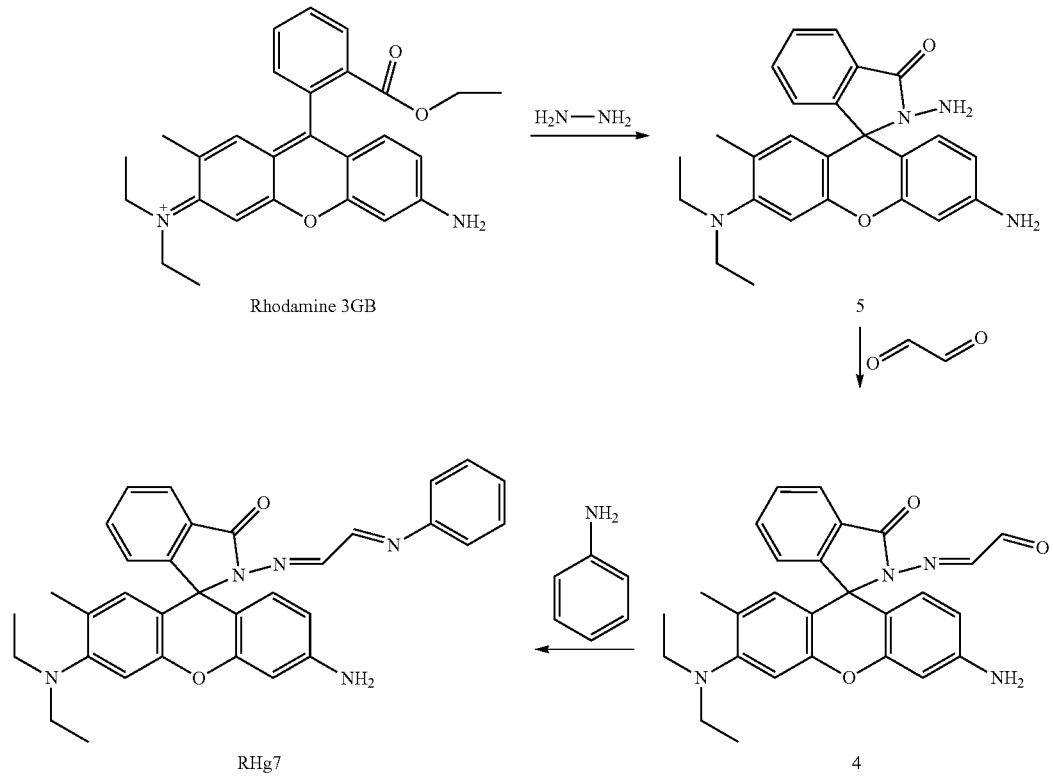

(1) The Synthesis of Intermediate 5:

Rhodamine 3 GB (1.16 g, 2.5 mmol) was added into a 100 ml single-necked flask containing 30 ml ethanol. The mixture was stirred vigorously at room temperature, followed by dropwise addition of excessive amount of 85% hydrazine hydrate solution (3 ml). After finishing the addition of hydrazine hydrage, the mixture was refluxed for 2 h in air until the solution changed from purple to light brown in color and finally became clear. Then the solution was cooled down to room temperature and ethanol was removed under reduced pressure. After that, 50 ml HCl (1 M) was added to give a red solution, and then 70 ml NaOH aqueous solution (1 M) was added under stirring to adjust pH to 9 to 10 to form a large amount of precipitation. The precipitation was filtered and washed with 15 ml water for three times, then dried under vacuum and purified through column chromatography to produce 0.67 g intermediate 5, yield 65%. $^1$H NMR (400 MHz CDCl$_3$) δ (ppm): 1.25(t, 6H), 1.97(s, 3H), 3.14(t, 4H), 4.23(s, 2H), 5.81(s, 2H), 6.01(s, 2H), 6.10(m, 1H), 6.27(s, 2H), 6.95 (d, J=8 Hz, 1H), 7.47(d, J=8 Hz, 1H), 7.48(d, J=8 Hz, 1H), 7.85(t, 1H); $^{13}$C NMR (400 MHz, CDCl$_3$), δ: 12.7, 19.8, 44.5, 66.04, 98.09, 103.78, 108.17, 109.9, 123.98, 124.07, 126.58, 128.62, 134.97, 149.21, 152.64, 152.87, 165.87; TOF MS (ES): m/z Calcd for $C_{25}H_{26}N_4O_2^+$: 414.2056, Found: 414.2072.

(2) The Synthesis of Intermediate 4:

The intermediate 5 (0.41 g, 1.0 mmol) was added into a 100 ml single-necked flask, and then absolute ethanol 30 ml and 40% glyoxal aqueous solution (0.58 g, 4.0 mmol) (excessive in amount) were added. The reaction mixture was stirred for 2 h at room temperature under nitrogen protection, and then the solvent was removed under reduced pressure. The product was purified through silica column chromatography with a mixture of petroleum ether (bp 60 to 90° C.) and ethyl acetate (v/v, 5/1) as elution solution to produce 0.42 g yellow solid 4 with a yield of 77%. $^1$H NMR (400 MHz CDCl$_3$) δ (ppm): 1.25(t, 6H), 1.97(s, 3H), 3.14(t, 4H), 4.23(s, 2H), 5.81(s, 2H), 6.10(m, 2H), 6.22(d, 2H), 6.27(s, 2H), 6.95(d, J=8 Hz, 1H), 7.47(d, J=8 Hz, 1H),7.48(d, J=8 Hz, 1H), 7.85(t, 1H); $^{13}$C NMR (400 MHz, CDCl$_3$), δ: 12.7, 19.8, 44.5, 66.04, 98.09, 103.78, 108.17, 109.9, 123.98, 124.07, 126.58, 128.62, 134.97, 149.21, 152.64, 152.87, 154.3, 165.87, 193.5; TOF MS (ES): m/z Calcd for $C_{27}H_{26}N_4O_3^+$: 454.2005, Found: 454.2014.

(3) The Synthesis of RHg7:

The intermediate 4 (0.45 g, 1.0 mmol) was added into a 100 ml single-necked flask, and then absolute 30 ml and aniline (0.44 g, 4 mmol) (excessive in amount) were added. The reaction mixture was stirred for 2 h at room temperature under nitrogen protection, and then the solvent was removed under reduced pressure. The product was purified through silica column chromatography with a mixture of petroleum ether (bp 60-90° C.) and ethyl acetate (v/v, 5/1) as elution solution to produce 0.42 g yellow solid RHg7 with a yield of 80%. $^1$H NMR (400 MHz CDCl$_3$) δ (ppm): 1.25(t, 6H), 1.97(s, 3H), 3.14(t, 4H), 5.81(s, 2H), 6.01(s, 2H), 6.10(m, 1H), 6.27(s, 2H), 7.09(m, 2H), 7.31(m, 4H), 7.47(m, 2H), 7.95(d, J=8 Hz, 1H), 8.01(d, J=8 Hz, 1H), 8.34(d, J=8 Hz, 1H); $^{13}$C NMR (100 MHz, CDCl$_3$), δ: 12.9, 20.1, 44.9, 68.0, 103.1, 109.9, 114.8, 120.6, 122.3, 128.0, 130.1, 132.7, 139.5, 145.6, 147.5, 149.0, 151.8, 163.0, 168.0; TOF MS (ES): m/z Calcd for $C_{20}H_{16}N_4O_2^+$: 344.1273, Found: 344.1250.

Example 18

Figure 15:
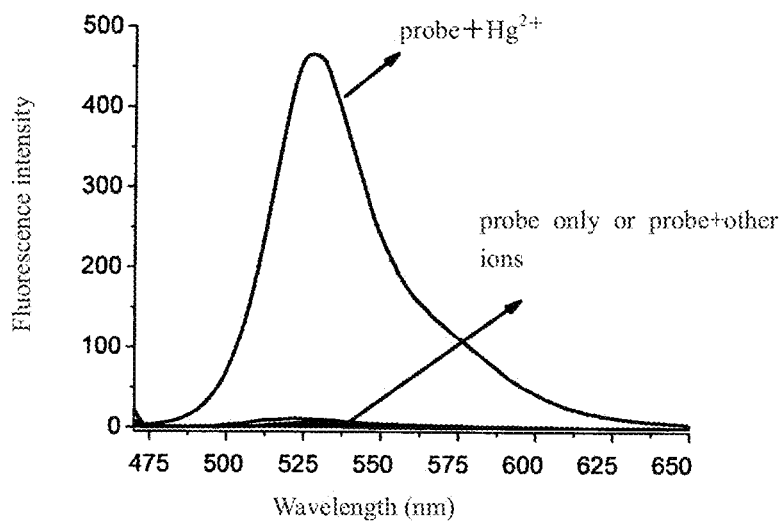
FIG. 15 is fluorescence emission spectra of fluorescence probe RHg7 coordinating $Hg^{2+}$ over other metal ions. Concentration of RHg7 is 5 µM, and concentrations of the metal ions are 50 equivalence ($Hg^{2+}$ is 15 equivalence). X-axis is wavelength (nm) and Y-axis is fluorescence intensity. The instrument is fluorospectrophotometer, model: LS 55.

The Selectivity Test of RHg7 to $Hg^{2+}$:

The synthesized compound RHg7 was adopted to test the selectivity to $Hg^{2+}$. RHg7 (5 μM) was added into ethanol aqueous solution (ethanol/water=1/1, v/v) containing metal ion (50 equivalence, except that $Hg^{2+}$ is 15 equivalence), and then the fluorescence spectrum was tested, the result is shown in FIG. 15. From FIG. 15, it can be seen that, RHg7 exhibits good selectivity to $Hg^{2+}$ and large fluorescence and UV-Vis absorption enhancement is induced by $Hg^{2+}$ without the interference from $Na^+$, $K^+$, $Ca^{2+}$, $Mg^{2+}$, $Cu^{2+}$ and so on. The instrument is fluorospectrophotometer, model: LS 55.

Example 19

The Synthesis of RHg8:

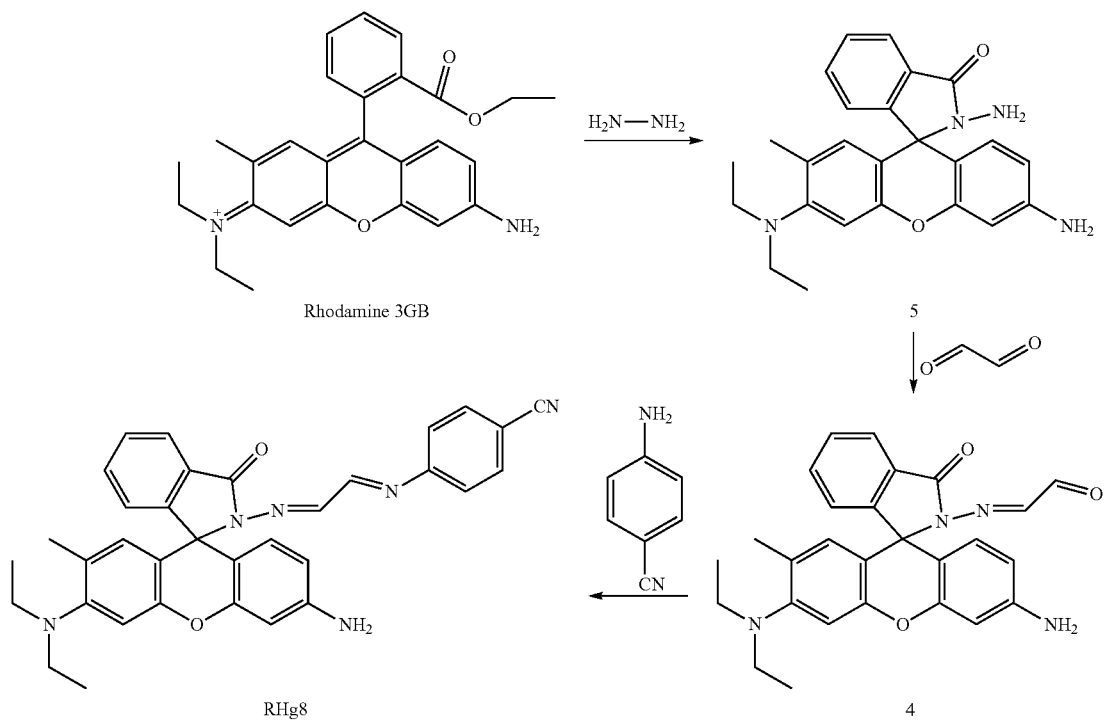

(1) The Synthesis of Intermediate 5:

Rhodamine 3 GB (1.16 g, 2.5 mmol) was added into a 100 ml single-necked flask containing 30 ml ethanol. The mixture was stirred vigorously at room temperature, followed by dropwise addition of excessive amount of 85% hydrazine hydrate solution (3 ml). After finishing the addition of hydrazine hydrage, the mixture was refluxed for 2 h in air until the solution changed from purple to light brown in color and finally became clear. Then the solution was cooled down to room temperature and ethanol was removed under reduced pressure. After that, 50 ml HCl (1 M) was added to give a red solution, and then 70 ml NaOH aqueous solution (1 M) was added under stirring to adjust pH to 9 to 10 to form a large amount of precipitation. The precipitation was filtered and washed with 15 ml water for three times, then dried under vacuum and purified through column chromatography to produce 0.67 g intermediate 5, yield 65%. $^1$H NMR (400 MHz CDCl$_3$) δ (ppm): 1.25(t, 6H), 1.97(s, 3H), 3.14(t, 4H), 4.23(s, 2H), 5.81(s, 2H), 6.01(s, 2H), 6.10(m, 1H), 6.27(s, 2H), 6.95 (d, J=8 Hz, 1H), 7.47(d, J=8 Hz, 1H), 7.48(d, J=8 Hz, 1H), 7.85(t, 1H); $^{13}$C NMR (400 MHz, CDCl$_3$), δ: 12.7, 19.8, 44.5, 66.04, 98.09, 103.78, 108.17, 109.9, 123.98, 124.07, 126.58, 128.62, 134.97, 149.21, 152.64, 152.87, 165.87; TOF MS (ES): m/z Calcd for $C_{25}H_{26}N_4O_2^+$: 414.2056, Found: 414.2072.

(2) The Synthesis of Intermediate 4:

The intermediate 5 (0.41 g, 1.0 mmol) was added into a 100 ml single-necked flask, and then absolute ethanol 30 ml and 40% glyoxal aqueous solution (0.58 g, 4.0 mmol) (excessive in amount) were added. The reaction mixture was stirred for 2 h at room temperature under nitrogen protection, and then the solvent was removed under reduced pressure. The product was purified through silica column chromatography with a mixture of petroleum ether (bp 60 to 90° C.) and ethyl acetate (v/v, 5/1) as elution solution to produce 0.42 g yellow solid 4 with a yield of 77%. $^1$H NMR (400 MHz CDCl$_3$) δ (ppm): 1.25(t, 6H), 1.97(s, 3H), 3.14(t, 4H), 4.23(s, 2H), 5.81(s, 2H), 6.10(m, 2H), 6.22(d, 2H), 6.27(s, 2H), 6.95(d, J=8 Hz, 1H), 7.47(d, J=8 Hz, 1H),7.48(d, J=8 Hz, 1H), 7.85(t, 1H); $^{13}$C NMR (400 MHz, CDCl$_3$), δ: 12.7, 19.8, 44.5, 66.04, 98.09, 103.78, 108.17, 109.9, 123.98, 124.07, 126.58, 128.62, 134.97, 149.21, 152.64, 152.87, 154.3, 165.87, 193.5; TOF MS (ES): m/z Calcd for $C_{27}H_{26}N_4O_3^+$: 454.2005, Found: 454.2014.

(3) The Synthesis of RHg8:

The intermediate 2 (0.45 g, 1 mmol) was added into a 100 ml single-necked flask, and then absolute 30 ml and 4-aminobenzonitrile (0.47 g, 4 mmol) (excessive in amount) were added. The reaction mixture was stirred for 2 h at room temperature under nitrogen protection, and then the solvent was removed under reduced pressure. The product was purified through silica column chromatography with a mixture of petroleum ether (bp 60-90° C.) and ethyl acetate (v/v, 5/1) as elution solution to produce 0.38 g yellow solid RHg8 with a yield of 78%. $^1$H NMR (400 MHz CDCl$_3$) δ (ppm): 1.25(t, 6H), 1.97(s, 3H), 3.14(t, 4H), 5.81(s, 2H), 6.01(s, 2H), 6.10 (m, 1H), 6.27(s, 2H), 7.09(d, J=8 Hz, 1H), 7.47(m, 6H), 7.95(d, J=8 Hz, 1H), 8.01(d, J=8 Hz, 1H), 8.34(d, J=8 Hz, 1H); $^{13}$C NMR (100 MHz, CDCl$_3$), δ: 12.9, 20.1, 44.9, 68.0, 103.1, 109.9, 111.1, 115.7, 120.6, 123.0, 126.4, 128.3, 131.3, 133.5, 139.5, 145.6, 147.5, 151.8, 153.3, 163.0; TOF MS (ES): m/z Calcd for $C_{20}H_{16}N_4O_2^+$: 344.1273, Found: 344.1250.

Example 20

Figure 16:
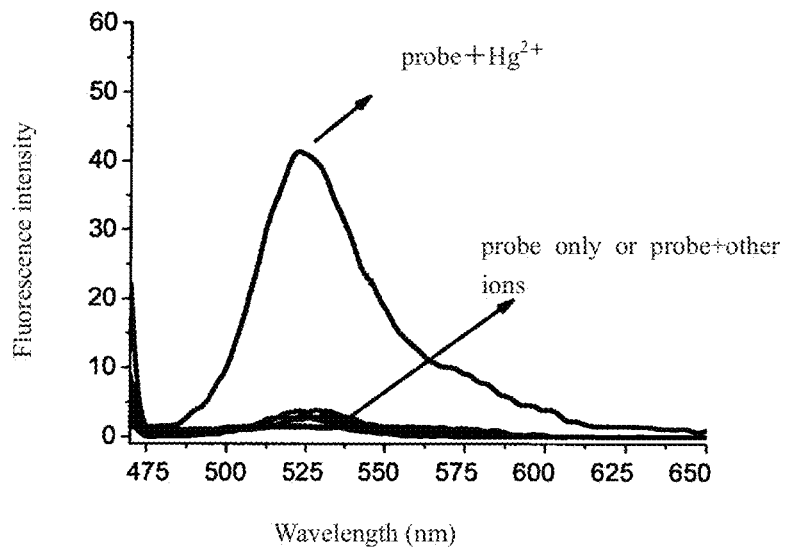
FIG. 16 is fluorescence emission spectra of fluorescence probe RHg8 coordinating $Hg^{2+}$ over other metal ions. Concentration of RHg8 is 5 µM, and concentrations of metal ions are 50 equivalence ($Hg^{2+}$ is 15 equivalence). X-axis is wavelength (nm) and Y-axis is fluorescence intensity. The instrument is fluorospectrophotometer, model: LS 55.

The Selectivity Test of RHg8 to $Hg^{2+}$:

The synthesized compound RHg8 was adopted to test the selectivity to $Hg^{2+}$. RHg8 (5 μM) was added into ethanol aqueous solution (ethanol/water=1/1, v/v) containing metal ion (50 equivalence, except that $Hg^{2+}$ is 15 equivalence), and then the fluorescence spectrum was tested, the result is shown in FIG. 16. From FIG. 16, it can be seen that, RHg8 exhibits good selectivity to $Hg^{2+}$ and large fluorescence and UV-Vis absorption enhancement is induced by $Hg^{2+}$ without the interference from $Na^+$, $K^+$, $Ca^{2+}$, $Mg^{2+}$, $Cu^{2+}$ and so on. The instrument is fluorospectrophotometer, model: LS 55.

Example 21

The Synthesis of RHg9:

solution changed from purple to light brown in color and finally became clear. Then the solution was cooled down to room temperature and ethanol was removed under reduced pressure. After that, 50 ml HCl (1 M) was added to give a red solution, and then 70 ml NaOH aqueous solution (1 M) was added under stirring to adjust pH to 9 to 10 to form a large amount of precipitation. The precipitation was filtered and washed with 15 ml water for three times, then dried under vacuum and purified through column chromatography to produce 0.67 g intermediate 5, yield 65%. $^1$H NMR (400 MHz CDCl$_3$) δ (ppm): 1.25(t, 6H), 1.97(s, 3H), 3.14(t, 4H), 4.23(s, 2H), 5.81(s, 2H), 6.01(s, 2H), 6.10(m, 1H), 6.27(s, 2H), 6.95 (d, J=8 Hz, 1H), 7.47(d, J=8 Hz, 1H), 7.48(d, J=8 Hz, 1H), 7.85 (t, 1H); $^{13}$C NMR (400 MHz, CDCl$_3$), δ: 12.7, 19.8, 44.5, 66.04, 98.09, 103.78, 108.17, 109.9, 123.98, 124.07, 126.58, 128.62, 134.97, 149.21, 152.64, 152.87, 165.87; TOF MS (ES): m/z Calcd for $C_{25}H_{26}N_4O_2^+$: 414.2056, Found: 414.2072.

(2) The Synthesis of Intermediate 4:

The intermediate 5 (0.41 g, 1.0 mmol) was added into a 100 ml single-necked flask, and then absolute ethanol 30 ml and 40% glyoxal aqueous solution (0.58 g, 4.0 mmol) (excessive in amount) were added. The reaction mixture was stirred for 2 h at room temperature under nitrogen protection, and then the solvent was removed under reduced pressure. The product

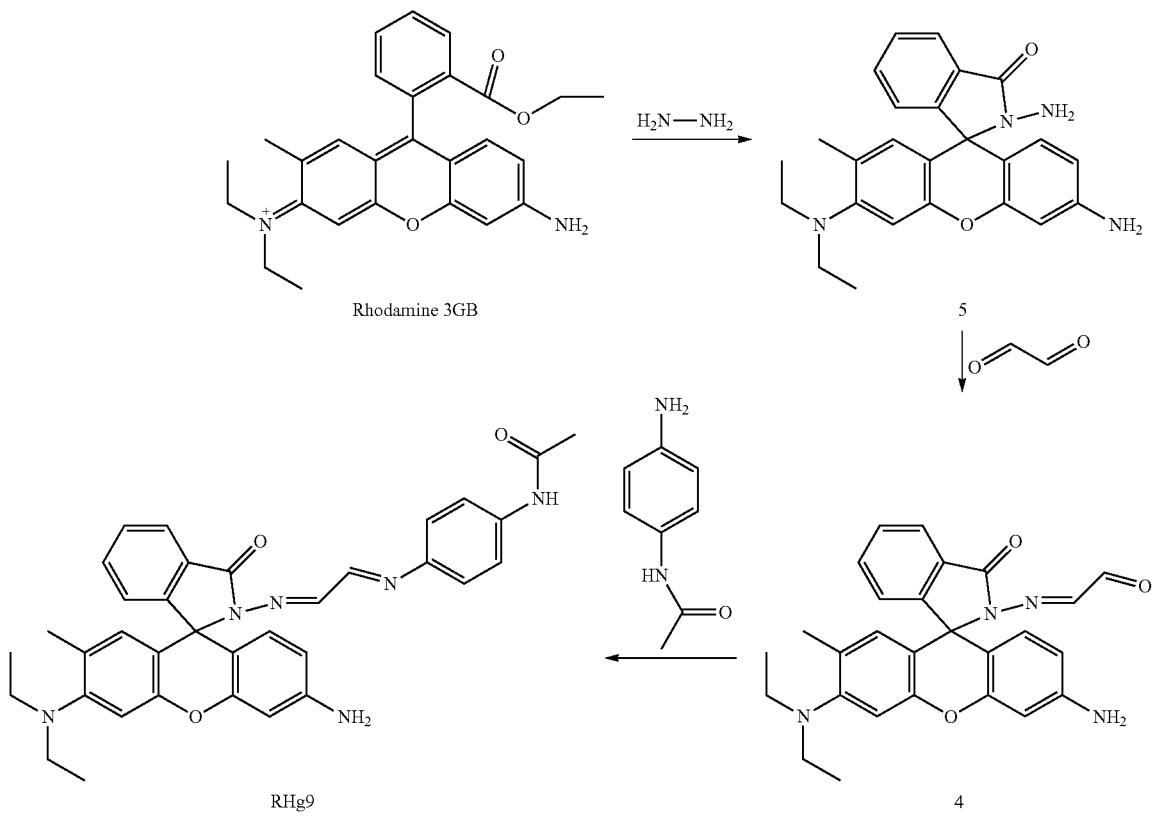

(1) The Synthesis of Intermediate 5:

Rhodamine 3 GB (1.16 g, 2.5 mmol) was added into a 100 ml single-necked flask containing 30 ml ethanol. The mixture was stirred vigorously at room temperature, followed by dropwise addition of excessive amount of 85% hydrazine hydrate solution (3 ml). After finishing the addition of hydrazine hydrage, the mixture was refluxed for 2 h in air until the was purified through silica column chromatography with a mixture of petroleum ether (bp 60 to 90° C.) and ethyl acetate (v/v, 5/1) as elution solution to produce 0.42 g yellow solid 4 with a yield of 77%. $^1$H NMR (400 MHz CDCl$_3$) δ (ppm): 1.25(t, 6H), 1.97(s, 3H), 3.14(t, 4H), 4.23(s, 2H), 5.81(s, 2H), 6.10(m, 2H), 6.22(d, 2H), 6.27(s, 2H), 6.95(d, J=8 Hz, 1H), 7.47(d, J=8 Hz, 1H), 7.48(d, J=8 Hz, 1H), 7.85(t, 1H); $^{13}$C NMR (400 MHz, CDCl$_3$), δ: 12.7, 19.8, 44.5, 66.04, 98.09, 103.78, 108.17, 109.9, 123.98, 124.07, 126.58, 128.62, 134.97, 149.21, 152.64, 152.87, 154.3, 165.87, 193.5; TOF MS (ES): m/z Calcd for $C_{27}H_{26}N_4O_3^+$: 454.2005, Found: 454.2014.

(3) The Synthesis of RHg9:

The intermediate 4 (0.45 g, 1 mmol) was added into a 100 ml single-necked flask, and then absolute 30 ml and N-(4-aminophenyl)acetamide (0.6 g, 4 mmol) (excessive in amount) were added. The reaction mixture was stirred for 2 h at room temperature under nitrogen protection, and then the solvent was removed under reduced pressure. The product was purified through silica column chromatography with a mixture of petroleum ether (bp 60-90° C.) and ethyl acetate (v/v, 5/1) as elution solution to produce 0.41 g yellow solid RHg9 with a yield of 70%. $^1$H NMR (400 MHz CDCl$_3$) δ (ppm): 1.25(t, 6H), 1.97(s, 3H), 2.03(s, 3H), 3.14(t, 4H), 5.81(s, 2H), 6.01(s, 2H), 6.10(m, 1H), 6.27(s, 2H), 7.09(s, 3H), 7.47(m, 4H), 7.95(d, J=8 Hz, 1H), 8.01(d, J=8 Hz, 1H), 8.34(d, J=8 Hz, 1H), 10.01(s, 1H); $^{13}$C NMR (400 MHz, CDCl$_3$), δ: 12.9, 20.1, 22.9, 44.9, 68.1, 103.1, 109.9, 114.3, 120.6, 122.9, 126.4, 128.3, 132.7, 136.9, 139.5, 144.6, 147.5, 151.8, 163.0, 168.9,; TOF MS (ES): m/z Calcd for $C_{20}H_{16}N_4O_2^+$: 344.1273, Found: 344.1250.

Example 22

Figure 17:
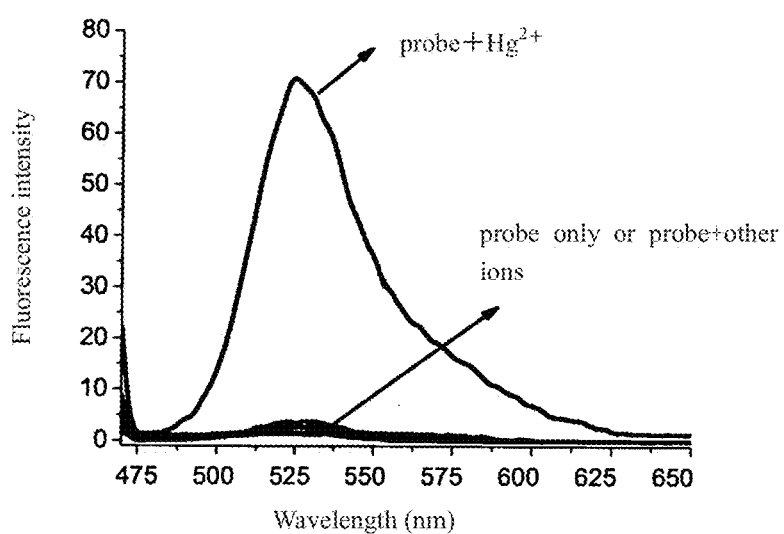
FIG. 17 is fluorescence emission spectra of fluorescence probe RHg9 coordinating $Hg^{2+}$ over other metal ions. Concentration of RHg9 is 5 µM, and concentrations of the metal ions are 50 equivalence ($Hg^{2+}$ is 15 equivalence). X-axis is wavelength (nm) and Y-axis is fluorescence intensity. The instrument is fluorospectrophotometer, model: LS 55.

The Selectivity Test of RHg9 to Hg$^{2+}$:

The synthesized compound RHg9 was adopted to test the selectivity to Hg$^{2+}$. RHg9 (5 µM) was added into ethanol aqueous solution (ethanol/water=1/1, v/v) containing metal ion (50 equivalence, except that Hg$^{2+}$ is 15 equivalence), and then the fluorescence spectrum was tested, the result is shown in FIG. 17. From FIG. 17, it can be seen that, RHg9 exhibits good selectivity to Hg$^{2+}$ and large fluorescence and UV-Vis absorption enhancement is induced by Hg$^{2+}$ without the interference from Na$^+$, K$^+$, Ca$^{2+}$, Mg$^{2+}$, Cu$^{2+}$ and so on. The instrument is fluorospectrophotometer, model: LS 55.

Example 23

The Synthesis of RHg10:

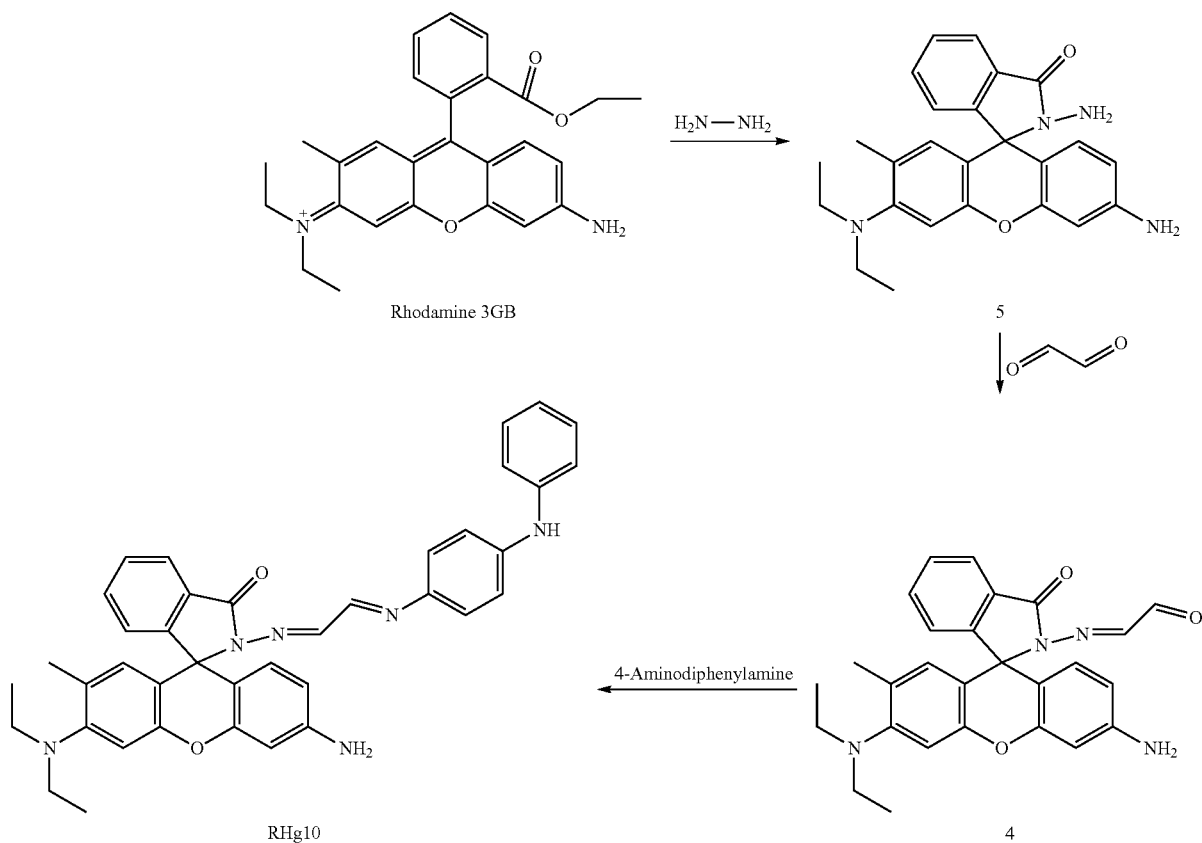

(1) The Synthesis of Intermediate 5:

Rhodamine 3 GB (1.16 g, 2.5 mmol) was added into a 100 ml single-necked flask containing 30 ml ethanol. The mixture was stirred vigorously at room temperature, followed by dropwise addition of excessive amount of 85% hydrazine hydrate solution (3 ml). After finishing the addition of hydrazine hydrage, the mixture was refluxed for 2 h in air until the solution changed from purple to light brown in color and finally became clear. Then the solution was cooled down to room temperature and ethanol was removed under reduced pressure. After that, 50 ml HCl (1 M) was added to give a red solution, and then 70 ml NaOH aqueous solution (1 M) was added under stirring to adjust pH to 9 to 10 to form a large amount of precipitation. The precipitation was filtered and washed with 15 ml water for three times, then dried under vacuum and purified through column chromatography to produce 0.67 g intermediate 5, yield 65%. $^1$H NMR (400 MHz CDCl$_3$) δ (ppm): 1.25(t, 6H), 1.97(s, 3H), 3.14(t, 4H), 4.23(s, 2H), 5.81(s, 2H), 6.01(s, 2H), 6.10(m, 1H), 6.27(s, 2H), 6.95 (d, J=8 Hz, 1H), 7.47(d, J=8 Hz, 1H), 7.48(d, J=8 Hz, 1H), 7.85(t, 1H); $^{13}$C NMR (400 MHz, CDCl$_3$), δ: 12.7, 19.8, 44.5, 66.04, 98.09, 103.78, 108.17, 109.9, 123.98, 124.07, 126.58, 128.62, 134.97, 149.21, 152.64, 152.87, 165.87; TOF MS (ES): m/z Calcd for $C_{25}H_{26}N_4O_2^+$: 414.2056, Found: 414.2072.

(2) The Synthesis of Intermediate 4:

The intermediate 5 (0.41 g, 1.0 mmol) was added into a 100 ml single-necked flask, and then absolute ethanol 30 ml and 40% glyoxal aqueous solution (0.58 g, 4.0 mmol) (excessive in amount) were added. The reaction mixture was stirred for 2 h at room temperature under nitrogen protection, and then the solvent was removed under reduced pressure. The product was purified through silica column chromatography with a mixture of petroleum ether (bp 60 to 90° C.) and ethyl acetate (v/v, 5/1) as elution solution to produce 0.42 g yellow solid 4 with a yield of 77%. $^1$H NMR (400 MHz CDCl$_3$) δ (ppm): 1.25(t, 6H), 1.97(s, 3H), 3.14(t, 4H), 4.23 (s, 2H), 5.81(s, 2H), 6.10(m, 2H), 6.22(d, 2H), 6.27(s, 2H), 6.95(d, J=8 Hz, 1H), 7.47(d, J=8 Hz, 1H), 7.48(d, J=8 Hz, 1H), 7.85(t, 1H); $^{13}$C NMR (400 MHz, CDCl$_3$), δ: 12.7, 19.8, 44.5, 66.04, 98.09, 103.78, 108.17, 109.9, 123.98, 124.07, 126.58, 128.62, 134.97, 149.21, 152.64, 152.87, 154.3, 165.87, 193.5; TOF MS (ES): m/z Calcd for $C_{27}H_{26}N_4O_3^+$: 454.2005, Found: 454.2014.

(3) The Synthesis of RHg10:

The intermediate 4 (0.45 g, 1 mmol) was added into a 100 ml single-necked flask, and then absolute 30 ml and 4-aminodiphenylamine (0.74 g, 4 mmol) (excessive in amount) were added. The reaction mixture was stirred for 2 h at room temperature under nitrogen protection, and then the solvent was removed under reduced pressure. The product was purified through silica column chromatography with a mixture of petroleum ether (bp 60-90° C.) and ethyl acetate (v/v, 5/1) as elution solution to produce 0.52 g yellow solid RHg10 with a yield of 84%. $^1$H NMR (400 MHz CDCl$_3$) δ (ppm): 1.25(t, 6H), 1.97(s, 3H), 3.14(t, 4H), 5.81(s, 2H), 6.01(s, 2H), 6.10 (m, 1H), 6.27(s, 2H), 7.09(m, 4H), 7.31(m, 4H), 7.47(m, 2H), 7.95(d, J=8 Hz, 1H), 8.01(d, J=8 Hz, 1H), 8.34(d, J=8 Hz, 1H), 9.77(s, 1H); $^{13}$C NMR (100 MHz, CDCl$_3$), δ: 12.9, 20.1, 44.6, 68.0, 103.1, 109.9, 114.8, 118.3, 119.1, 120.4, 123.2, 126.4, 128.3, 129.7, 131.3, 132.7, 138.0, 138.5, 139.5, 145.6, 147.5, 151.7, 163.0, 168.0; TOF MS (ES): m/z Calcd for $C_{20}H_{16}N_4O_2^+$: 344.1273, Found: 344.1250.

Example 24

Figure 18:
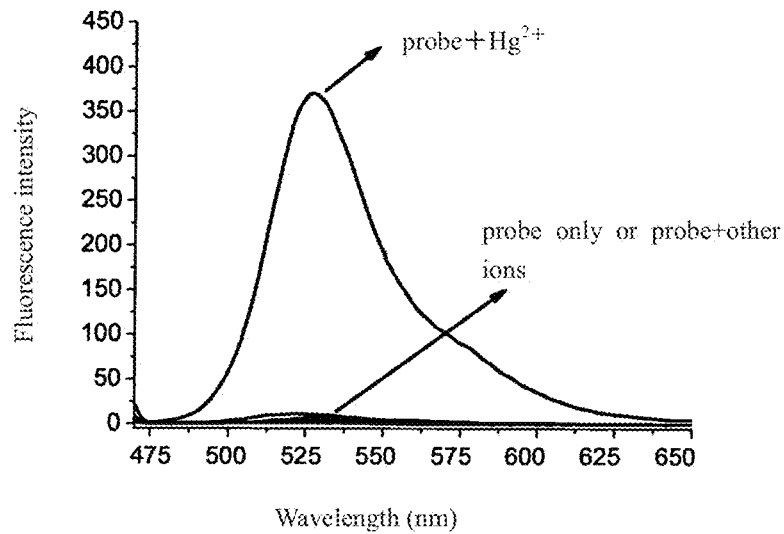
FIG. 18 is fluorescence emission spectra of fluorescence probe RHg10 coordinating $Hg^{2+}$ over other metal ions. Concentration of RHg10 is 5 µM, and concentrations of the metal ions are 50 equivalence ($Hg^{2+}$ is 15 equivalence). X-axis is wavelength (nm) and Y-axis is fluorescence intensity. The instrument is fluorospectrophotometer, model: LS 55.

The selectivity test of RHg10 to $Hg^{2+}$:

The synthesized compound RHg10 was adopted to test the selectivity to $Hg^{2+}$. RHg10 (5 μM) was added into ethanol aqueous solution (ethanol/water=1/1, v/v) containing metal ion (50 equivalence, except that $Hg^{2+}$ is 15 equivalence), and then the fluorescence spectrum was tested, the result is shown in FIG. 18. From FIG. 18, it can be seen that, RHg10 exhibits good selectivity to $Hg^{2+}$ and large fluorescence and UV-Vis absorption enhancement is induced by $Hg^{2+}$ without the interference from $Na^+$, $K^+$, $Ca^{2+}$, $Mg^{2+}$, $Cu^{2+}$ and so on. The instrument is fluorospectrophotometer, model: LS 55.

Example 25

The Synthesis of RHg11:

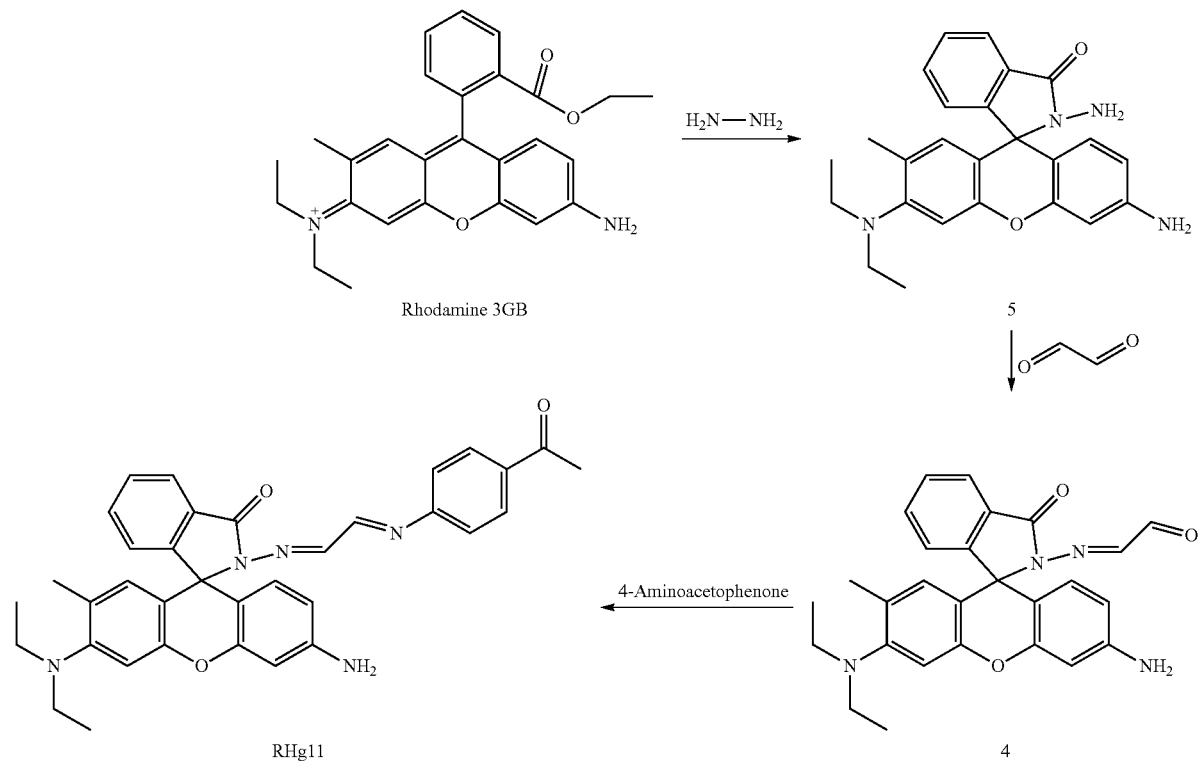

(1) The Synthesis of Intermediate 5:

Rhodamine 3 GB (1.16 g, 2.5 mmol) was added into a 100 ml single-necked flask containing 30 ml ethanol. The mixture was stirred vigorously at room temperature, followed by dropwise addition of excessive amount of 85% hydrazine hydrate solution (3 ml). After finishing the addition of hydrazine hydrage, the mixture was refluxed for 2 h in air until the solution changed from purple to light brown in color and finally became clear. Then the solution was cooled down to room temperature and ethanol was removed under reduced pressure. After that, 50 ml HCl (1 M) was added to give a red solution, and then 70 ml NaOH aqueous solution (1 M) was added under stirring to adjust pH to 9 to 10 to form a large amount of precipitation. The precipitation was filtered and washed with 15 ml water for three times, then dried under vacuum and purified through column chromatography to produce 0.67 g intermediate 5, yield 65%. $^1$H NMR (400 MHz CDCl$_3$) δ (ppm): 1.25(t, 6H), 1.97(s, 3H), 3.14(t, 4H), 4.23(s, 2H), 5.81 (s, 2H), 6.01(s, 2H), 6.10(m, 1H), 6.27(s, 2H), 6.95(d, J=8 Hz, 1H), 7.47(d, J=8 Hz, 1H), 7.48(d, J=8 Hz, 1H), 7.85(t, 1H); $^{13}$C NMR (400 MHz, CDCl$_3$), δ: 12.7, 19.8, 44.5, 66.04, 98.09, 103.78, 108.17, 109.9, 123.98, 124.07, 126.58, 128.62, 134.97, 149.21, 152.64, 152.87, 165.87; TOF MS (ES): m/z Calcd for $C_{25}H_{26}N_4O_2^+$: 414.2056, Found: 414.2072.

(2) The Synthesis of Intermediate 4:

The intermediate 5 (0.41 g, 1.0 mmol) was added into a 100 ml single-necked flask, and then absolute ethanol 30 ml and 40% glyoxal aqueous solution (0.58 g, 4.0 mmol) (excessive in amount) were added. The reaction mixture was stirred for 2 h at room temperature under nitrogen protection, and then the solvent was removed under reduced pressure. The product was purified through silica column chromatography with a mixture of petroleum ether (bp 60 to 90° C.) and ethyl acetate (v/v, 5/1) as elution solution to produce 0.42 g yellow solid 4 with a yield of 77%. $^1$H NMR (400 MHz CDCl$_3$) δ (ppm): 1.25(t, 6H), 1.97(s, 3H), 3.14(t, 4H), 4.23(s, 2H), 5.81(s, 2H), 6.10(m, 2H), 6.22(d, 2H), 6.27(s, 2H), 6.95(d, J=8 Hz, 1H), 7.47(d, J=8 Hz, 1H), 7.48(d, J=8 Hz, 1H), 7.85(t, 1H); $^{13}$C NMR (400 MHz, CDCl$_3$), δ: 12.7, 19.8, 44.5, 66.04, 98.09, 103.78, 108.17, 109.9, 123.98, 124.07, 126.58, 128.62, 134.97, 149.21, 152.64, 152.87, 154.3, 165.87, 193.5; TOF MS (ES): m/z Calcd for $C_{27}H_{26}N_4O_3^+$: 454.2005, Found: 454.2014.

(3) The Synthesis of RHg11:

The intermediate 4 (0.45 g, 1 mmol) was added into a 100 ml single-necked flask, and then absolute 30 ml and 4-aminoacetophenone (0.54 g, 4 mmol) (excessive in amount) were added. The reaction mixture was stirred for 2 h at room temperature under nitrogen protection, and then the solvent was removed under reduced pressure. The product was purified through silica column chromatography with a mixture of petroleum ether (bp 60-90° C.) and ethyl acetate (v/v, 5/1) as elution solution to produce 0.43 g yellow solid RHg11 with a yield of 75%. $^1$H NMR (400 MHz CDCl$_3$) δ (ppm): 1.25(t, 6H), 1.97(s, 3H), 2.55(s, 3H), 3.14(t, 4H), 5.81(s, 2H), 6.01(s, 2H), 6.10(m, 1H), 6.27(s, 2H), 7.09(d, J=8 Hz, 1H), 7.47(m, 4H), 7.95(m, 3H), 8.01(d, J=8 Hz, 1H), 8.34(d, J=8 Hz, 1H); $^{13}$C NMR (400 MHz, CDCl$_3$), δ: 12.9, 20.1, 29.3, 44.6, 68.0, 103.1, 109.9, 114.8, 120.9, 122.2, 126.4, 128.0, 128.3, 130.1, 132.7, 135.2, 139.5, 145.6, 147.5, 151.8, 153.4, 163.0, 168.0, 199.8; TOF MS (ES): m/z Calcd for $C_{20}H_{16}N_4O_2^+$: 344.1273, Found: 344.1250.

Example 26

Figure 19:
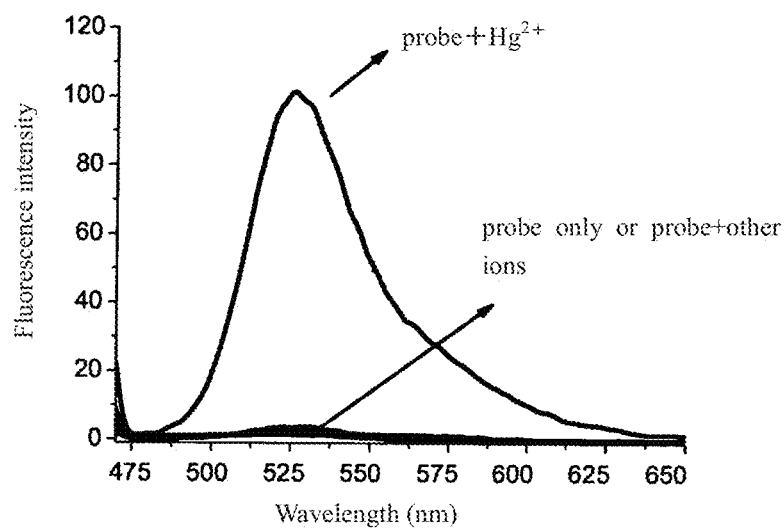
FIG. 19 is fluorescence emission spectra of fluorescence probe RHg11 coordinating $Hg^{2+}$ over other metal ions. Concentration of RHg11 is 5 µM, and concentrations of metal ions are 50 equivalence ($Hg^{2+}$ is 15 equivalence). X-axis is wavelength (nm) and Y-axis is fluorescence intensity. The instrument is fluorospectrophotometer, model: LS 55.

The Selectivity Test of RHg11 to Hg$^{2+}$:

The synthesized compound RHg11 was adopted to test the selectivity to Hg$^{2+}$. RHg11 (5 μM) was added into ethanol aqueous solution (ethanol/water=1/1, v/v) containing metal ion (50 equivalence, except that Hg$^{2+}$ is 15 equivalence), and then the fluorescence spectrum was tested, the result is shown in FIG. 19. From FIG. 19, it can be seen that, RHg11 exhibits good selectivity to Hg$^{2+}$ and large fluorescence and UV-Vis absorption enhancement is induced by Hg$^{2+}$ without the interference from Na$^+$, K$^+$, Ca$^{2+}$, Mg$^{2+}$, Cu$^{2+}$ and so on. The instrument is fluorospectrophotometer, model: LS 55.

Example 27

The Synthesis of RHg12:

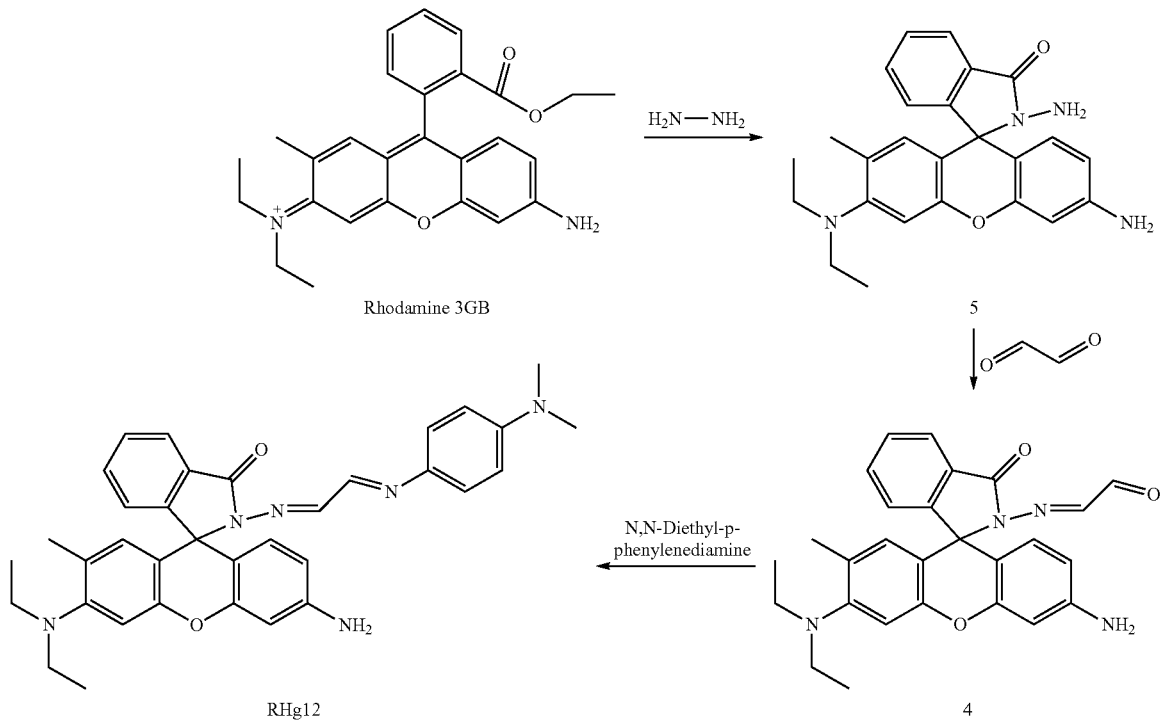

(1) The Synthesis of Intermediate 5:

Rhodamine 3 GB (1.16 g, 2.5 mmol) was added into a 100 ml single-necked flask containing 30 ml ethanol. The mixture was stirred vigorously at room temperature, followed by dropwise addition of excessive amount of 85% hydrazine hydrate solution (3 ml). After finishing the addition of hydrazine hydrage, the mixture was refluxed for 2 h in air until the solution changed from purple to light brown in color and finally became clear. Then the solution was cooled down to room temperature and ethanol was removed under reduced pressure. After that, 50 ml HCl (1 M) was added to give a red solution, and then 70 ml NaOH aqueous solution (1 M) was added under stirring to adjust pH to 9 to 10 to form a large amount of precipitation. The precipitation was filtered and washed with 15 ml water for three times, then dried under vacuum and purified through column chromatography to produce 0.67 g intermediate 5, yield 65%. $^1$H NMR (400 MHz CDCl$_3$) δ (ppm): 1.25(t, 6H), 1.97(s, 3H), 3.14(t, 4H), 4.23(s, 2H), 5.81(s, 2H), 6.01(s, 2H), 6.10(m, 1H), 6.27(s, 2H), 6.95 (d, J=8 Hz, 1H), 7.47(d, J=8 Hz, 1H), 7.48(d, J=8 Hz, 1H), 7.85(t, 1H); $^{13}$C NMR (400 MHz, CDCl$_3$), δ: 12.7, 19.8, 44.5, 66.04, 98.09, 103.78, 108.17, 109.9, 123.98, 124.07, 126.58, 128.62, 134.97, 149.21, 152.64, 152.87, 165.87; TOF MS (ES): m/z Calcd for $C_{25}H_{26}N_4O_2^+$: 414.2056, Found: 414.2072.

(2) the Synthesis of Intermediate 4:

The intermediate 5 (0.41 g, 1.0 mmol) was added into a 100 ml single-necked flask, and then absolute ethanol 30 ml and 40% glyoxal aqueous solution (0.58 g, 4.0 mmol) (excessive in amount) were added. The reaction mixture was stirred for 2 h at room temperature under nitrogen protection, and then the solvent was removed under reduced pressure. The product was purified through silica column chromatography with a mixture of petroleum ether (bp 60 to 90° C.) and ethyl acetate (v/v, 5/1) as elution solution to produce 0.42 g yellow solid 4 with a yield of 77%. $^1$H NMR (400 MHz CDCl$_3$) δ (ppm): 1.25(t, 6H), 1.97(s, 3H), 3.14(t, 4H), 4.23(s, 2H), 5.81(s, 2H), 6.10(m, 2H), 6.22(d, 2H), 6.27(s, 2H), 6.95(d, J=8 Hz, 1H), 7.47(d, J=8 Hz, 1H), 7.48(d, J=8 Hz, 1H), 7.85(t, 1H); $^{13}$C NMR (400 MHz, CDCl$_3$), δ: 12.7, 19.8, 44.5, 66.04, 98.09, 103.78, 108.17, 109.9, 123.98, 124.07, 126.58, 128.62, 134.97, 149.21, 152.64, 152.87, 154.3, 165.87, 193.5; TOF MS (ES): m/z Calcd for $C_{27}H_{26}N_4O_3^+$: 454.2005, Found: 454.2014.

(3) The Synthesis of RHg12:

The intermediate 4 (0.45 g, 1 mmol) was added into a 100 ml single-necked flask, and then absolute 30 ml and N,N-dimethyl-p-phenylenediamine (0.54 g, 4 mmol) (excessive in amount) were added. The reaction mixture was stirred for 2 h at room temperature under nitrogen protection, and then the solvent was removed under reduced pressure. The product was purified through silica column chromatography with a mixture of petroleum ether (bp 60-90° C.) and ethyl acetate (v/v, 5/1) as elution solution to produce 0.50 g yellow solid RHg12 with a yield of 88%. $^1$H NMR (400 MHz CDCl$_3$) δ (ppm): 1.25(t, 6H), 1.97(s, 3H), 3.13(s, 6H), 3.44(t, 4H), 5.81(s, 2H), 6.01(s, 2H), 6.10(m, 1H), 6.27(s, 2H), 6.83(m, 2H), 7.09(m, 3H), 7.47(m, 2H), 7.95(d, J=8 Hz, 1H), 8.01(d, J=8 Hz, 1H), 8.34(d, J=8 Hz, 1H); $^{13}$C NMR (100 MHz, CDCl$_3$), δ: 12.9, 20.1, 40.2, 44.9, 68.0, 103.1, 109.9, 114.8, 115.6, 120.9, 123.2, 126.4, 128.3, 131.3, 132.7, 138.5, 139.5, 145.6, 147.5, 148.1, 151.8, 163.0, 168.0.

Example 28

Figure 20:
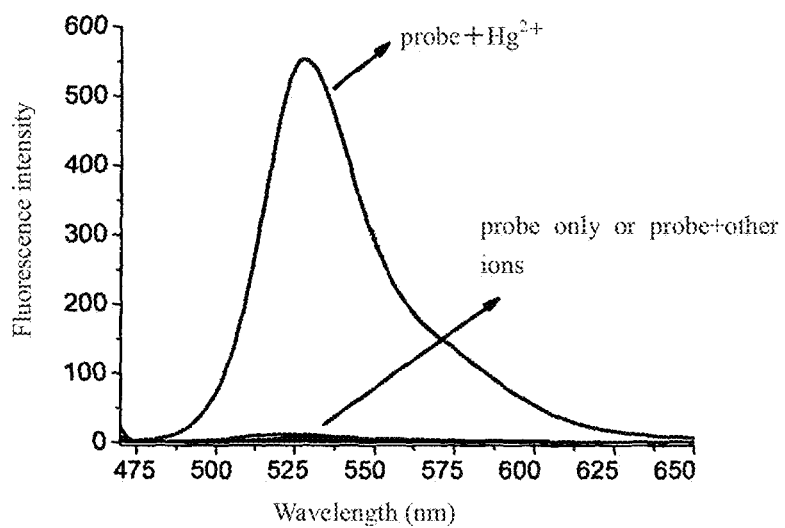
FIG. 20 is fluorescence emission spectra of fluorescence probe RHg12 coordinating $Hg^{2+}$ over other metal ions. Concentration of RHg12 is 5 μM, and concentrations of the metal ions are 50 equivalence ($Hg^{2+}$ is 15 equivalence). X-axis is wavelength (nm) and Y-axis is fluorescence intensity. The instrument is fluorospectrophotometer, model: LS 55.

The Selectivity Test of RHg12 to $Hg^{2+}$:

The synthesized compound RHg12 was adopted to test the selectivity to $Hg^{2+}$. RHg12 (5 μM) was added into ethanol aqueous solution (ethanol/water=1/1, v/v) containing metal ion (50 equivalence, except that $Hg^{2+}$ is 15 equivalence), and then the fluorescence spectrum was tested, the result is shown in FIG. 20. From FIG. 20, it can be seen that, RHg12 exhibits good selectivity to $Hg^{2+}$ and large fluorescence and UV-Vis absorption enhancement is induced by $Hg^{2+}$ without the interference from $Na^+$, $K^+$, $Ca^{2+}$, $Mg^{2+}$, $Cu^{2+}$ and so on. The instrument is fluorospectrophotometer, model: LS 55.

Example 29

The Synthesis of RHg13:

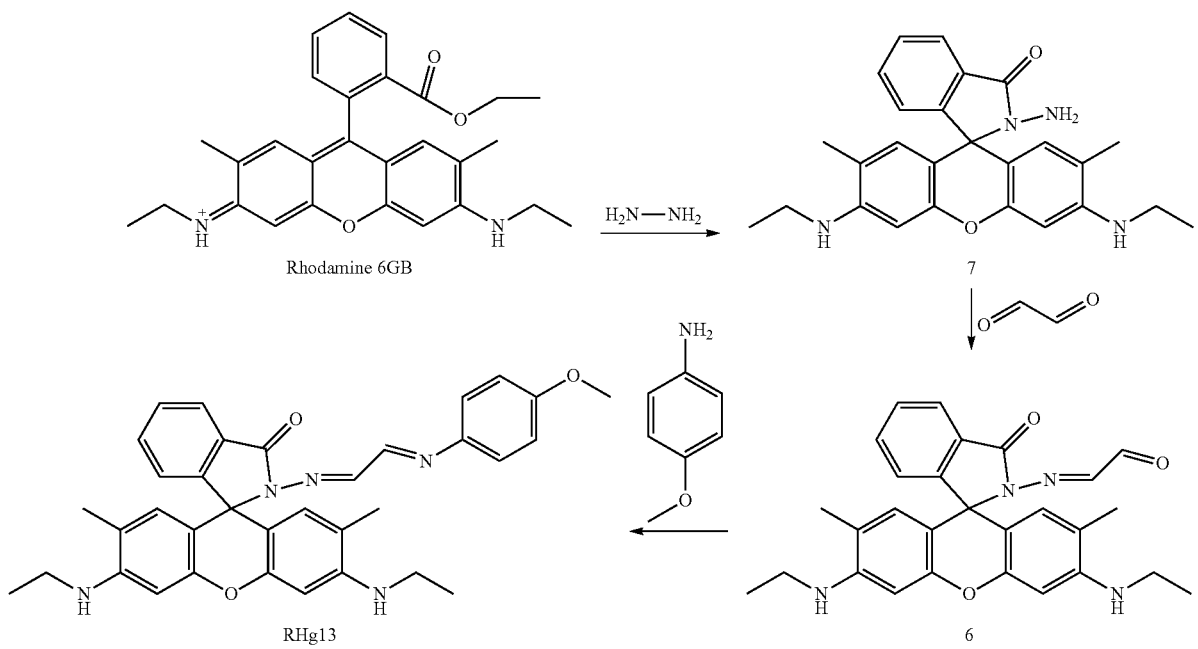

(1) The Synthesis of Intermediate 7:

Rhodamine 6G (1.2 g, 2.5 mmol) was added into a 100 ml single-necked flask containing 30 ml ethanol. The mixture was stirred vigorously at room temperature, followed by dropwise addition of excessive amount of 85% hydrazine hydrate solution (3 ml). After finishing the addition of hydrazine hydrage, the mixture was refluxed for 2 h in air until the solution changed from purple to light brown in color and finally became clear. Then the solution was cooled down to room temperature and ethanol was removed under reduced pressure. After that, 50 ml HCl (1 M) was added to give a red solution, and then 70 ml NaOH aqueous solution (1 M) was added under stirring to adjust pH to 9 to 10 to form a large amount of precipitation. The precipitation was filtered and washed with 15 ml water for three times, then dried under vacuum and purified through column chromatography to produce 0.64 g intermediate 7, yield 60%. $^1$H NMR (400 MHz CDCl$_3$) δ (ppm): 1.21(t, 6H), 1.87(s, 6H), 3.14(t, 4H), 4.23(s, 2H), 5.01(s, 1H), 6.10(s, 2H), 6.27(s, 2H), 6.95(d, J=8 Hz, 1H), 7.47(d, J=8 Hz, 1H), 7.48(d, J=8 Hz, 1H), 7.85(t, 1H); $^{13}$C NMR (400 MHz, CDCl$_3$), δ: 12.7, 19.8, 44.5, 66.04, 98.09, 103.78, 108.17, 123.98, 124.07, 126.58, 128.62, 134.97, 149.21, 152.64, 152.87, 165.87; TOF MS (ES): m/z Calcd for $C_{26}H_{28}N_4O_2^+$: 428.2212, Found: 428.2234.

(2) The Synthesis of Intermediate 6:

The intermediate 7 (0.43 g, 1.0 mmol) was added into a 100 ml single-necked flask, and then absolute ethanol 30 ml and 40% glyoxal aqueous solution (0.58 g, 4.0 mmol) (excessive in amount) were added. The reaction mixture was stirred for 2 h at room temperature under nitrogen protection, and then the solvent was removed under reduced pressure. The product was purified through silica column chromatography with a mixture of petroleum ether (bp 60 to 90° C.) and ethyl acetate (v/v, 5/1) as elution solution to produce 0.33 g yellow solid 6 with a yield of 70%. $^1$H NMR (400 MHz CDCl$_3$) δ (ppm): 1.21(t, 6H), 1.87(s, 6H), 3.14(t, 4H), 5.01(s, 1H), 6.10(s, 2H), 6.27(s, 2H), 6.95(d, J=8 Hz, 1H), 7.47(d, J=8 Hz, 1H), 7.45 (m, 1H), 7.48(d, J=8 Hz, 1H), 7.85(t, 1H), 9.42(d, J=8 Hz, 1H); $^{13}$C NMR (400 MHz, CDCl$_3$), δ: 12.7, 19.8, 44.5, 66.04, 98.09, 103.78, 108.17, 123.98, 124.07, 126.58, 128.62, 134.97, 149.21, 152.64, 152.87, 165.87; TOF MS (ES): m/z Calcd for $C_{28}H_{28}N_4O_3^+$: 468.2161, Found: 468.2178.

(3) The Synthesis of RHg13:

The intermediate 6 (0.47 g, 1 mmol) was added into a 100 ml single-necked flask, and then absolute 30 ml and 4-methoxyaniline (0.49 g, 4 mmol) (excessive in amount) were added. The reaction mixture was stirred for 2 h at room temperature under nitrogen protection, and then the solvent was removed under reduced pressure. The product was purified through silica column chromatography with a mixture of petroleum ether (bp 60-90° C.) and ethyl acetate (v/v, 5/1) as elution solution to produce 0.51 g yellow solid RHg13 with a yield of 89%. $^1$H NMR (400 MHz CDCl$_3$) δ (ppm): 1.21(t, 6H), 1.87(s, 6H), 3.14(t, 4H), 3.77(s, 3H), 4.23(s, 2H), 5.01(s, 1H), 6.10(s, 2H), 6.27(s, 2H), 7.09(m, 3H), 7.20(d, J=8 Hz, 2H), 7.47(m, 2H), 7.95(d, J=8 Hz, 1H), 8.01(d, J=8 Hz, 1H), 8.34(d, J=8 Hz, 1H),; $^{13}$C NMR (100 MHz, CDCl$_3$), δ: 12.7, 19.8, 44.5, 55.8, 68.0, 100.0, 115.6, 119.9, 123.3, 128.7, 132.7, 139.5, 141.3, 142.6, 147.5, 159.1, 163.0, 168.0; TOF MS (ES): m/z Calcd for $C_{20}H_{16}N_4O_2^+$: 344.1273, Found: 344.1250.

Example 30

Figure 21:
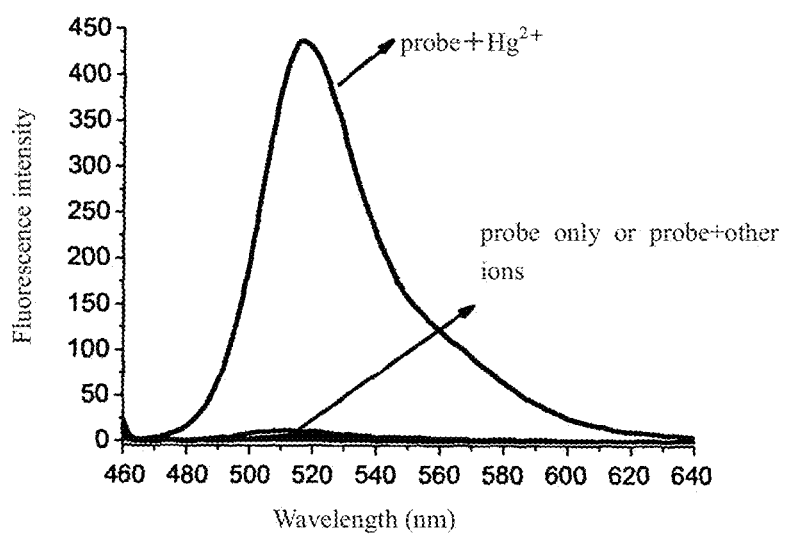
FIG. 21 is fluorescence emission spectra of fluorescence probe RHg13 coordinating $Hg^{2+}$ over other metal ions. Concentration of RHg13 is 5 μM, and concentrations of the metal ions are 50 equivalence ($Hg^{2+}$ is 15 equivalence). X-axis is wavelength (nm) and Y-axis is fluorescence intensity. The instrument is fluorospectrophotometer, model: LS 55.

The Selectivity Test of RHg13 to Hg$^{2+}$:

The synthesized compound RHg13 was adopted to test the selectivity to Hg$^{2+}$. RHg13 (5 μM) was added into ethanol aqueous solution (ethanol/water=1/1, v/v) containing metal ion (50 equivalence, except that Hg$^{2+}$ is 15 equivalence), and then the fluorescence spectrum was tested, the result is shown in FIG. 21. From FIG. 21, it can be seen that, RHg13 exhibits good selectivity to Hg$^{2+}$ and large fluorescence and UV-Vis absorption enhancement is induced by Hg$^{2+}$ without the interference from Na$^+$, K$^+$, Ca$^{2+}$, Mg$^{2+}$, Cu$^{2+}$ and so on. The instrument is fluorospectrophotometer, model: LS 55.

Example 31

The Synthesis of RHg14:

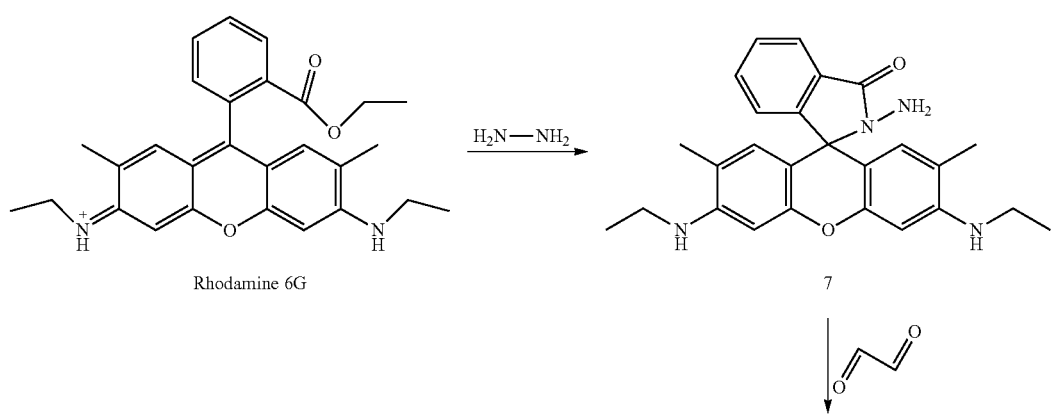

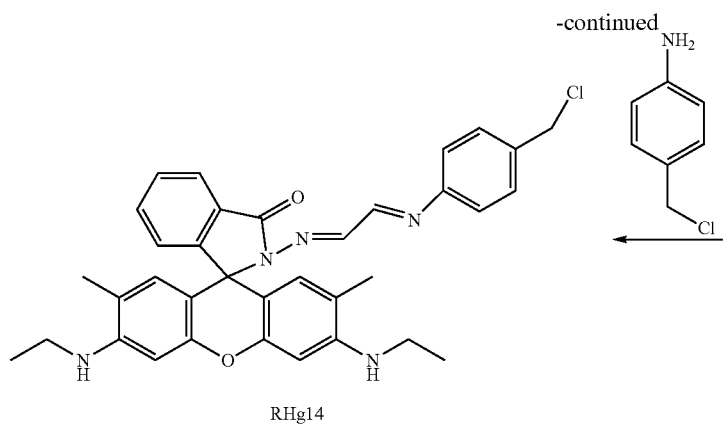

RHg14

-continued

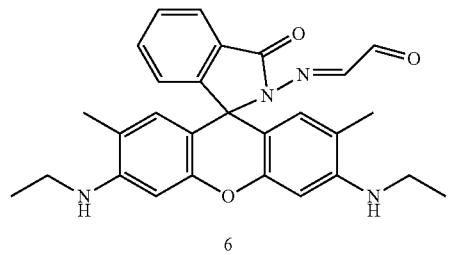

6

(1) The Synthesis of Intermediate 7:

Rhodamine 6G (1.2 g, 2.5 mmol) was added into a 100 ml single-necked flask containing 30 ml ethanol. The mixture was stirred vigorously at room temperature, followed by dropwise addition of excessive amount of 85% hydrazine hydrate solution (3 ml). After finishing the addition of hydrazine hydrage, the mixture was refluxed for 2 h in air until the solution changed from purple to light brown in color and finally became clear. Then the solution was cooled down to room temperature and ethanol was removed under reduced pressure. After that, 50 ml HCl (1 M) was added to give a red solution, and then 70 ml NaOH aqueous solution (1 M) was added under stirring to adjust pH to 9 to 10 to form a large amount of precipitation. The precipitation was filtered and washed with 15 ml water for three times, then dried under vacuum and purified through column chromatography to produce 0.64 g intermediate 7, yield 60%. $^1$H NMR (400 MHz CDCl$_3$) δ (ppm): 1.21(t, 6H), 1.87(s, 6H), 3.14(t, 4H), 4.23(s, 2H), 5.01(s, 1H), 6.10(s, 2H), 6.27(s, 2H), 6.95(d, J=8 Hz, 1H), 7.47(d, J=8 Hz, 1H), 7.48(d, J=8 Hz, 1H), 7.85(t, 1H); $^{13}$C NMR (400 MHz, CDCl$_3$), δ: 12.7, 19.8, 44.5, 66.04, 98.09, 103.78, 108.17, 123.98, 124.07, 126.58, 128.62, 134.97, 149.21, 152.64, 152.87, 165.87; TOF MS (ES): m/z Calcd for $C_{26}H_{28}N_4O_2^+$: 428.2212, Found: 428.2234.

(2) The Synthesis of Intermediate 6:

The intermediate 7 (0.43 g, 1.0 mmol) was added into a 100 ml single-necked flask, and then absolute ethanol 30 ml and 40% glyoxal aqueous solution (0.58 g, 4.0 mmol) (excessive in amount) were added. The reaction mixture was stirred for 2 h at room temperature under nitrogen protection, and then the solvent was removed under reduced pressure. The product was purified through silica column chromatography with a mixture of petroleum ether (bp 60 to 90° C.) and ethyl acetate (v/v, 5/1) as elution solution to produce 0.33 g yellow solid 6 with a yield of 70%. $^1$H NMR (400 MHz CDCl$_3$) δ (ppm): 1.21(t, 6H), 1.87(s, 6H), 3.14(t, 4H), 5.01(s, 1H), 6.10(s, 2H), 6.27(s, 2H), 6.95(d, J=8 Hz, 1H), 7.47(d, J=8 Hz, 1H), 7.45 (m, 1H), 7.48(d, J=8 Hz, 1H), 7.85(t, 1H), 9.42(d, J=8 Hz, 1H); $^{13}$C NMR (400 MHz, CDCl$_3$), δ: 12.7, 19.8, 44.5, 66.04, 98.09, 103.78, 108.17, 123.98, 124.07, 126.58, 128.62, 134.97, 149.21, 152.64, 152.87, 165.87; TOF MS (ES): m/z Calcd for $C_{28}H_{28}N_4O_3^+$: 468.2161, Found: 468.2178.

(3) The Synthesis of RHg14:

The intermediate 6 (0.47 g, 1 mmol) was added into a 100 ml single-necked flask, and then absolute 30 ml and 4-chloromethylaniline (0.56 g, 4 mmol) (excessive in amount) were added. The reaction mixture was stirred for 2 h at room temperature under nitrogen protection, and then the solvent was removed under reduced pressure. The product was purified through silica column chromatography with a mixture of petroleum ether (bp 60-90° C.) and ethyl acetate (v/v, 5/1) as elution solution to produce 0.49 g yellow solid RHg14 with a yield of 83%. $^1$H NMR (400 MHz CDCl$_3$) δ (ppm): 1.21(t, 6H), 1.87(s, 6H), 3.14(t, 4H), 4.23(s, 2H), 4.64(s, 2H), 5.01(s, 1H), 6.10(s, 2H), 6.27(s, 2H), 7.09(d, J=8 Hz, 1H), 7.47(m, 6H), 7.95(d, J=8 Hz, 1H), 8.01(d, J=8 Hz, 1H), 8.34(d, J=8 Hz, 1H); $^{13}$C NMR (400 MHz, CDCl$_3$), δ: 12.7, 19.8, 44.5, 46.3, 68.0, 103.1, 109.9, 114.8, 122.5, 126.4, 128.3, 129.9, 132.3, 136.3, 142.6, 148.8, 149.0, 163.0; TOF MS (ES): m/z Calcd for $C_{20}H_{16}N_4O_2^+$: 344.1273, Found: 344.1250.

Example 32

Figure 22:
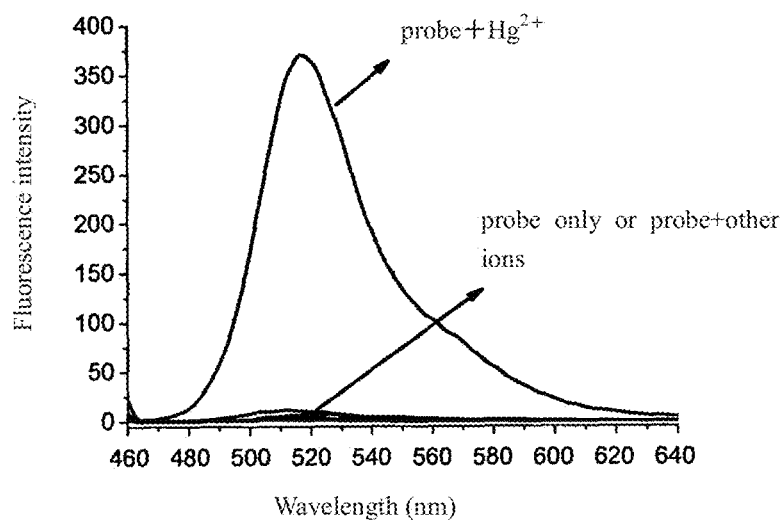
FIG. 22 is fluorescence emission spectra of fluorescence probe RHg14 coordinating $Hg^{2+}$ over other metal ions. Concentration of RHg14 is 5 μM, and concentrations of the metal ions are 50 equivalence ($Hg^{2+}$ is 15 equivalence). X-axis is wavelength (nm) and Y-axis is fluorescence intensity. The instrument is fluorospectrophotometer, model: LS 55.

The Selectivity Test of RHg14 to $Hg^{2+}$:

The synthesized compound RHg14 was adopted to test the selectivity to $Hg^{2+}$. RHg14 (5 μM) was added into ethanol aqueous solution (ethanol/water=1/1, v/v) containing metal ion (50 equivalence, except that $Hg^{2+}$ is 15 equivalence), and then the fluorescence spectrum was tested, the result is shown in FIG. 22. From FIG. 22, it can be seen that, RHg14 exhibits good selectivity to $Hg^{2+}$ and large fluorescence and UV-Vis absorption enhancement is induced by $Hg^{2+}$ without the interference from $Na^+$, $K^+$, $Ca^{2+}$, $Mg^{2+}$, $Cu^{2+}$ and so on. The instrument is fluorospectrophotometer, model: LS 55.

Example 33

The Synthesis of RHg15:

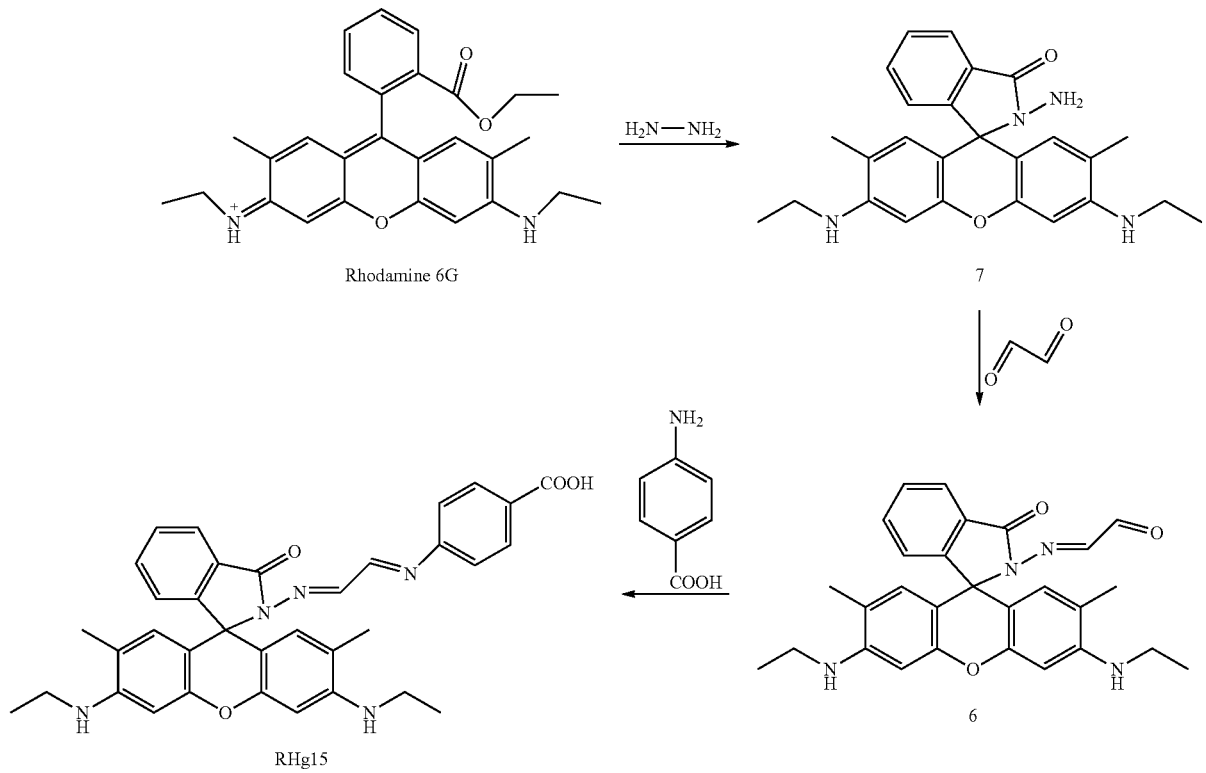

(1) The Synthesis of Intermediate 7:

Rhodamine 6G (1.2 g, 2.5 mmol) was added into a 100 ml single-necked flask containing 30 ml ethanol. The mixture was stirred vigorously at room temperature, followed by dropwise addition of excessive amount of 85% hydrazine hydrate solution (3 ml). After finishing the addition of hydrazine hydrage, the mixture was refluxed for 2 h in air until the solution changed from purple to light brown in color and finally became clear. Then the solution was cooled down to room temperature and ethanol was removed under reduced pressure. After that, 50 ml HCl (1 M) was added to give a red solution, and then 70 ml NaOH aqueous solution (1 M) was added under stirring to adjust pH to 9 to 10 to form a large amount of precipitation. The precipitation was filtered and washed with 15 ml water for three times, then dried under vacuum and purified through column chromatography to produce 0.64 g intermediate 7, yield 60%. $^1$H NMR (400 MHz CDCl$_3$) δ (ppm): 1.21(t, 6H), 1.87(s, 6H), 3.14(t, 4H), 4.23(s, 2H), 5.01(s, 1H), 6.10(s, 2H), 6.27(s, 2H), 6.95(d, J=8 Hz, 1H), 7.47(d, J=8 Hz, 1H), 7.48(d, J=8 Hz, 1H), 7.85(t, 1H); $^{13}$C NMR (400 MHz, CDCl$_3$), δ: 12.7, 19.8, 44.5, 66.04, 98.09, 103.78, 108.17, 123.98, 124.07, 126.58, 128.62, 134.97, 149.21, 152.64, 152.87, 165.87; TOF MS (ES): m/z Calcd for $C_{26}H_{28}N_4O_2^+$: 428.2212, Found: 428.2234.

(2) The Synthesis of Intermediate 6:

The intermediate 7 (0.43 g, 1.0 mmol) was added into a 100 ml single-necked flask, and then absolute ethanol 30 ml and 40% glyoxal aqueous solution (0.58 g, 4.0 mmol) (excessive in amount) were added. The reaction mixture was stirred for 2 h at room temperature under nitrogen protection, and then the solvent was removed under reduced pressure. The product was purified through silica column chromatography with a mixture of petroleum ether (bp 60 to 90° C.) and ethyl acetate (v/v, 5/1) as elution solution to produce 0.33 g yellow solid 6 with a yield of 70%. $^1$H NMR (400 MHz CDCl$_3$) δ (ppm): 1.21(t, 6H), 1.87(s, 6H), 3.14(t, 4H), 5.01(s, 1H), 6.10(s, 2H), 6.27(s, 2H), 6.95(d, J=8 Hz, 1H), 7.47(d, J=8 Hz, 1H), 7.45(m, 1H), 7.48(d, J=8 Hz, 1H), 7.85(t, 1H), 9.42(d, J=8 Hz, 1H); $^{13}$C NMR (400 MHz, CDCl$_3$), δ: 12.7, 19.8, 44.5, 66.04, 98.09, 103.78, 108.17, 123.98, 124.07, 126.58, 128.62, 134.97, 149.21, 152.64, 152.87, 165.87; TOF MS (ES): m/z Calcd for $C_{28}H_{28}N_4O_3^+$: 468.2161, Found: 468.2178.

(3) The Synthesis of RHg15:

The intermediate 6 (0.47 g, 1 mmol) was added into a 100 ml single-necked flask, and then absolute 30 ml and 4-aminobenzoic acid (0.55 g, 4 mmol) (excessive in amount) were added. The reaction mixture was stirred for 2 h at room temperature under nitrogen protection, and then the solvent was removed under reduced pressure. The product was purified through silica column chromatography with a mixture of petroleum ether (bp 60-90° C.) and ethyl acetate (v/v, 5/1) as elution solution to produce 0.47 g yellow solid RHg15 with a yield of 80%. $^1$H NMR (400 MHz CDCl$_3$) δ (ppm): 1.21(t, 6H), 1.87(s, 6H), 3.14(t, 4H), 4.23(s, 2H), 5.01(s, 1H), 6.10(s, 2H), 6.27(s, 2H), 7.09(d, J=8 Hz, 1H), 7.47(m, 4H), 7.95(d, J=8 Hz, 1H), 8.01(d, J=8 Hz, 1H), 8.18(d, J=8 Hz, 2H), 8.34(d, J=8 Hz, 1H), 12.79(s, 1H); $^{13}$C NMR (100 MHz, CDCl$_3$), δ: 12.7, 19.8, 44.5, 68.0, 100.1, 114.8, 119.9, 122.2, 126.4, 128.7, 131.6, 139.5, 142.6, 147.5, 148.8, 154.2, 163.0, 168.0, 169.3; TOF MS (ES): m/z Calcd for $C_{20}H_{16}N_4O_2^+$: 344.1273, Found: 344.1250.

Example 34

Figure 23:
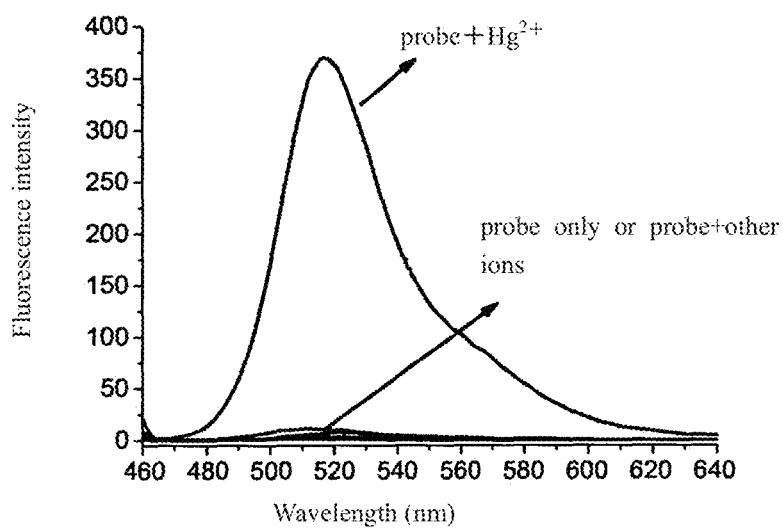
FIG. 23 is fluorescence emission spectra of fluorescence probe RHg15 coordinating $Hg^{2+}$ over other metal ions. Concentration of RHg15 is 5 μM, and concentrations of the metal ions are 50 equivalence ($Hg^{2+}$ is 15 equivalence). X-axis is wavelength (nm) and Y-axis is fluorescence intensity. The instrument is fluorospectrophotometer, model: LS 55.

The Selectivity Test of RHg15 to $Hg^{2+}$:

The synthesized compound RHg15 was adopted to test the selectivity to $Hg^{2+}$. RHg15 (5 μM) was added into ethanol aqueous solution (ethanol/water=1/1, v/v) containing metal ion (50 equivalence, except that $Hg^{2+}$ is 15 equivalence), and then the fluorescence spectrum was tested, the result is shown in FIG. 23. From FIG. 23, it can be seen that, RHg15 exhibits good selectivity to $Hg^{2+}$ and large fluorescence and UV-Vis absorption enhancement is induced by $Hg^{2+}$ without the interference from $Na^+$, $K^+$, $Ca^{2+}$, $Mg^{2+}$, $Cu^{2+}$ and so on. The instrument is fluorospectrophotometer, model: LS 55.

Example 35

The Synthesis of RHg16:

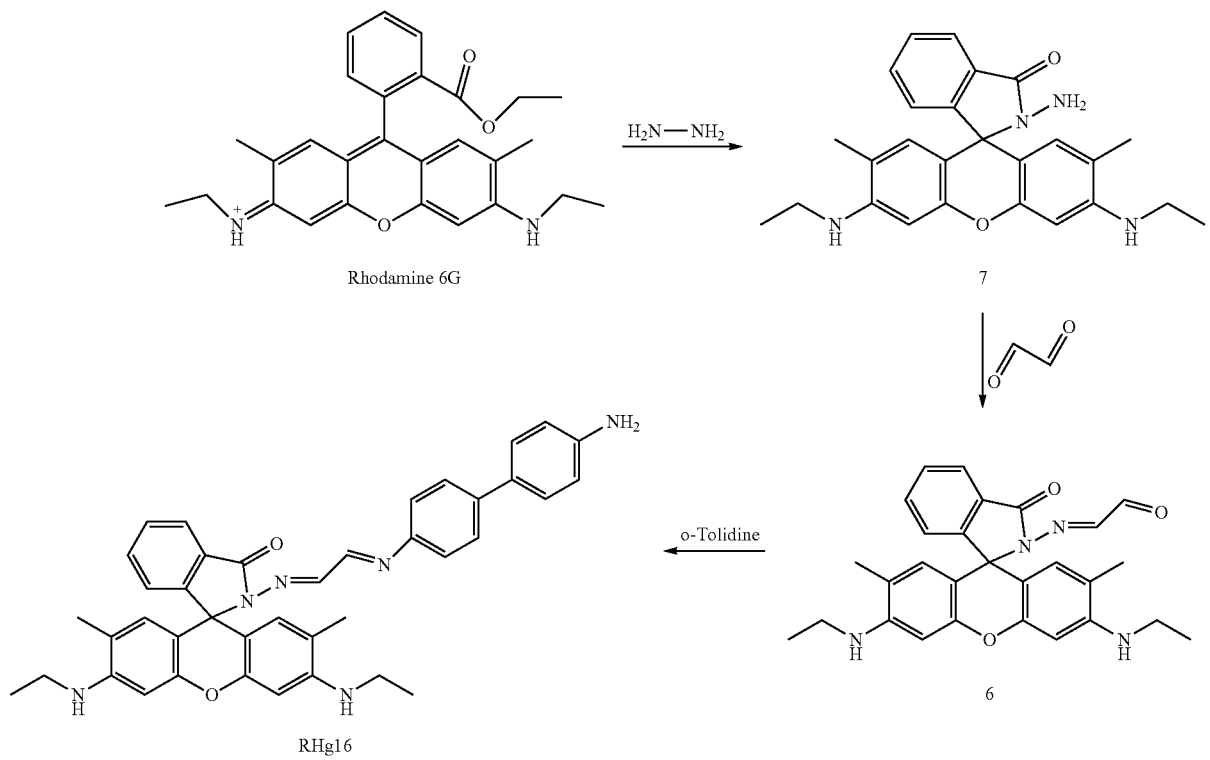

(1) The Synthesis of Intermediate 7:

Rhodamine 6G (1.2 g, 2.5 mmol) was added into a 100 ml single-necked flask containing 30 ml ethanol. The mixture was stirred vigorously at room temperature, followed by dropwise addition of excessive amount of 85% hydrazine hydrate solution (3 ml). After finishing the addition of hydrazine hydrage, the mixture was refluxed for 2 h in air until the solution changed from purple to light brown in color and finally became clear. Then the solution was cooled down to room temperature and ethanol was removed under reduced pressure. After that, 50 ml HCl (1 M) was added to give a red solution, and then 70 ml NaOH aqueous solution (1 M) was added under stirring to adjust pH to 9 to 10 to form a large amount of precipitation. The precipitation was filtered and washed with 15 ml water for three times, then dried under vacuum and purified through column chromatography to produce 0.64 g intermediate 7, yield 60%. $^1$H NMR (400 MHz $CDCl_3$) δ (ppm): 1.21(t, 6H), 1.87(s, 6H), 3.14(t, 4H), 4.23(s, 2H), 5.01(s, 1H), 6.10(s, 2H), 6.27(s, 2H), 6.95(d, J=8 Hz, 1H), 7.47(d, J=8 Hz, 1H), 7.48(d, J=8 Hz, 1H), 7.85(t, 1H); $^{13}$C NMR (400 MHz, $CDCl_3$), δ: 12.7, 19.8, 44.5, 66.04, 98.09, 103.78, 108.17, 123.98, 124.07, 126.58, 128.62, 134.97, 149.21, 152.64, 152.87, 165.87; TOF MS (ES): m/z Calcd for $C_{26}H_{28}N_4O_2^+$: 428.2212, Found: 428.2234.

(2) The Synthesis of Intermediate 6:

The intermediate 7 (0.43 g, 1.0 mmol) was added into a 100 ml single-necked flask, and then absolute ethanol 30 ml and 40% glyoxal aqueous solution (0.58 g, 4.0 mmol) (excessive in amount) were added. The reaction mixture was stirred for 2 h at room temperature under nitrogen protection, and then the solvent was removed under reduced pressure. The product was purified through silica column chromatography with a mixture of petroleum ether (bp 60 to 90° C.) and ethyl acetate (v/v, 5/1) as elution solution to produce 0.33 g yellow solid 6 with a yield of 70%. $^1$H NMR (400 MHz $CDCl_3$) δ (ppm): 1.21(t, 6H), 1.87(s, 6H), 3.14(t, 4H), 5.01(s, 1H), 6.10(s, 2H), 6.27(s, 2H), 6.95(d, J=8 Hz, 1H), 7.47(d, J=8 Hz, 1H), 7.45 (m, 1H), 7.48(d, J=8 Hz, 1H), 7.85(t, 1H), 9.42(d, J=8 Hz, 1H); $^{13}$C NMR (400 MHz, $CDCl_3$), δ: 12.7, 19.8, 44.5, 66.04, 98.09, 103.78, 108.17, 123.98, 124.07, 126.58, 128.62, 134.97, 149.21, 152.64, 152.87, 165.87; TOF MS (ES): m/z Calcd for $C_{28}H_{28}N_4O_3^+$: 468.2161, Found: 468.2178.

(3) The Synthesis of RHg16:

The intermediate 6 (0.47 g, 1 mmol) was added into a 100 ml single-necked flask, and then absolute 30 ml and o-tolidine (0.85 g, 4 mmol) (excessive in amount) were added. The reaction mixture was stirred for 2 h at room temperature under nitrogen protection, and then the solvent was removed under reduced pressure. The product was purified through silica column chromatography with a mixture of petroleum ether (bp 60-90° C.) and ethyl acetate (v/v, 5/1) as elution solution to produce 0.49 g yellow solid RHg16 with a yield of 78%. $^1$H NMR (400 MHz $CDCl_3$) δ (ppm): 1.21(t, 6H), 1.87(s, 6H), 3.14(t, 4H), 4.23(s, 2H), 5.01(s, 1H), 6.10(s, 2H), 6.27(s, 2H), 7.09(d, J=8 Hz, 1H), 7.30(d, J=8 Hz, 2H), 7.47(m, 6H), 7.95 (d, J=8 Hz, 1H), 8.01(d, J=8 Hz, 1H), 8.34(d, J=8 Hz, 1H); $^{13}$C NMR (100 MHz, CDCl$_3$), δ: 12.7, 19.8, 44.5, 68.0, 100.1, 114.8, 116.8, 119.9, 122.8, 126.4, 128.7, 129.2, 132.7, 134.9, 139.5, 142.6, 147.3, 148.8, 163.0, 168.0; TOF MS (ES): m/z Calcd for $C_{20}H_{16}N_4O_2^+$: 344.1273, Found: 344.1250.

Example 36

Figure 24:
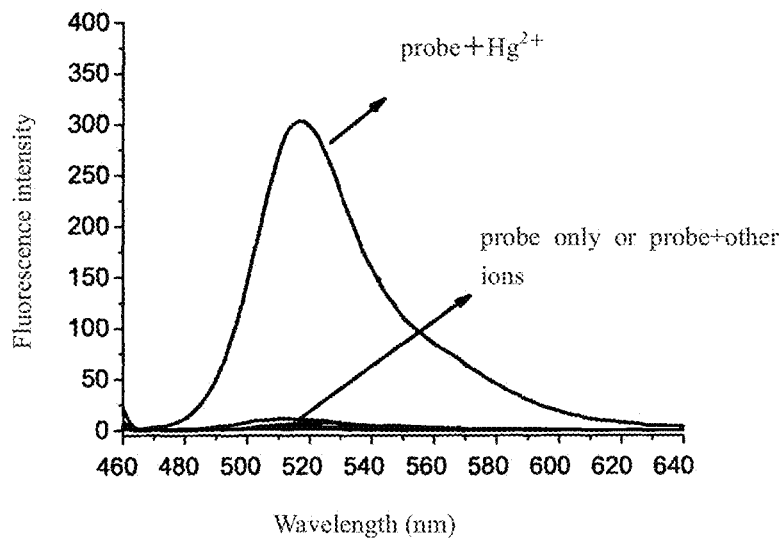
FIG. 24 is fluorescence emission spectra of fluorescence probe RHg16 coordinating $Hg^{2+}$ over other metal ions. Concentration of RHg16 is 5 μM, and concentrations of the metal ions are 50 equivalence ($Hg^{2+}$ is 15 equivalence). X-axis is wavelength (nm) and Y-axis is fluorescence intensity. The instrument is fluorospectrophotometer, model: LS 55.

The Selectivity Test of RHg16 to $Hg^{2+}$:

The synthesized compound RHg16 was adopted to test the selectivity to $Hg^{2+}$. RHg16 (5 µM) was added into ethanol aqueous solution (ethanol/water=1/1, v/v) containing metal ion (50 equivalence, except that $Hg^{2+}$ is 15 equivalence), and then the fluorescence spectrum was tested, the result is shown in FIG. 24. From FIG. 24, it can be seen that, RHg16 exhibits good selectivity to $Hg^{2+}$ and large fluorescence and UV-Vis absorption enhancement is induced by $Hg^{2+}$ without the interference from $Na^+$, $K^+$, $Ca^{2+}$, $Mg^{2+}$, $Cu^{2+}$ and so on. The instrument is fluorospectrophotometer, model: LS 55.

Example 37

The Synthesis of RHg17:

finally became clear. Then the solution was cooled down to room temperature and ethanol was removed under reduced pressure. After that, 50 ml HCl (1 M) was added to give a red solution, and then 70 ml NaOH aqueous solution (1 M) was added under stirring to adjust pH to 9 to 10 to form a large amount of precipitation. The precipitation was filtered and washed with 15 ml water for three times, then dried under vacuum and purified through column chromatography to produce 0.64 g intermediate 7, yield 60%. $^1$H NMR (400 MHz CDCl$_3$) δ (ppm): 1.21(t, 6H), 1.87(s, 6H), 3.14(t, 4H), 4.23(s, 2H), 5.01(s, 1H), 6.10(s, 2H), 6.27(s, 2H), 6.95(d, J=8 Hz, 1H), 7.47(d, J=8 Hz, 1H), 7.48(d, J=8 Hz, 1H), 7.85(t, 1H); $^{13}$C NMR (400 MHz, CDCl$_3$), δ: 12.7, 19.8, 44.5, 66.04, 98.09, 103.78, 108.17, 123.98, 124.07, 126.58, 128.62, 134.97, 149.21, 152.64, 152.87, 165.87; TOF MS (ES): m/z Calcd for $C_{26}H_{28}N_4O_2^+$: 428.2212, Found: 428.2234.

(2) The Synthesis of Intermediate 6:

The intermediate 7 (0.43 g, 1.0 mmol) was added into a 100 ml single-necked flask, and then absolute ethanol 30 ml and 40% glyoxal aqueous solution (0.58 g, 4.0 mmol) (excessive in amount) were added. The reaction mixture was stirred for 2 h at room temperature under nitrogen protection, and then the solvent was removed under reduced pressure. The product was purified through silica column chromatography with a

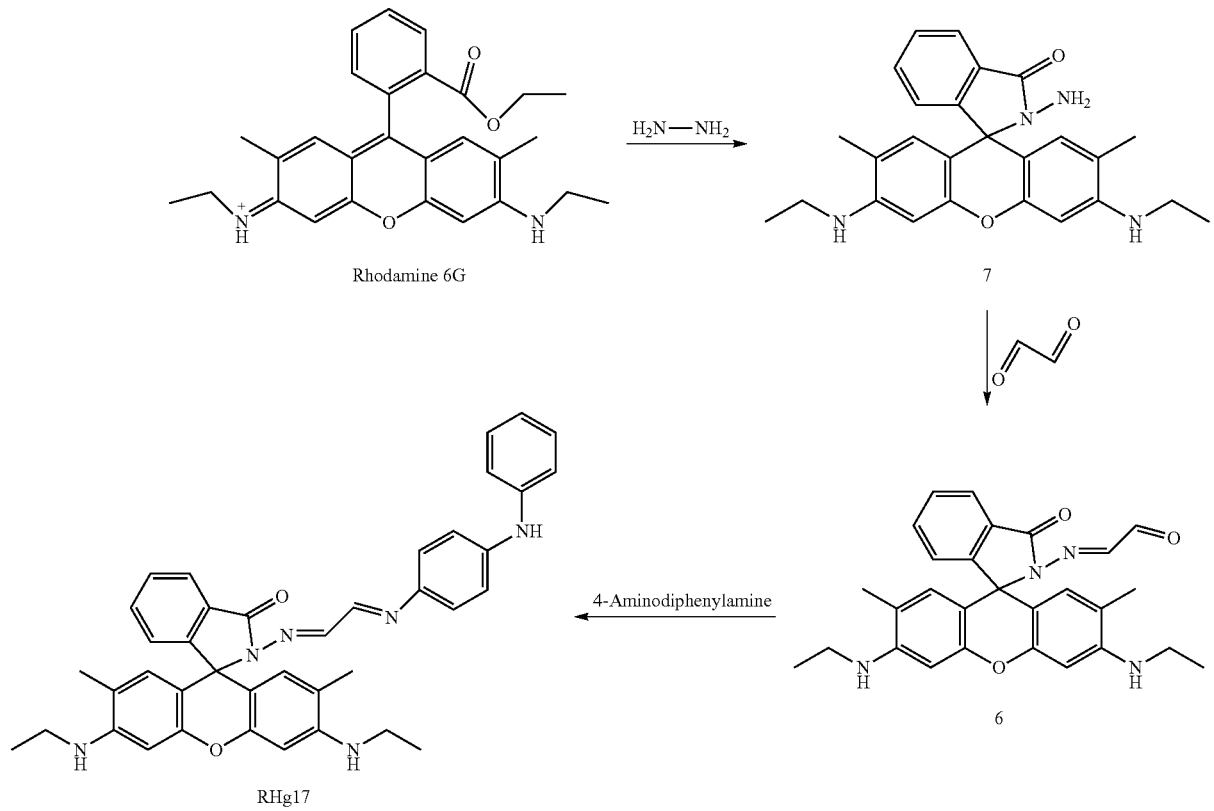

(1) The Synthesis of Intermediate 7:

Rhodamine 6G (1.2 g, 2.5 mmol) was added into a 100 ml single-necked flask containing 30 ml ethanol. The mixture was stirred vigorously at room temperature, followed by dropwise addition of excessive amount of 85% hydrazine hydrate solution (3 ml). After finishing the addition of hydrazine hydrage, the mixture was refluxed for 2 h in air until the solution changed from purple to light brown in color and mixture of petroleum ether (bp 60 to 90° C.) and ethyl acetate (v/v, 5/1) as elution solution to produce 0.33 g yellow solid 6 with a yield of 70%. $^1$H NMR (400 MHz CDCl$_3$) δ (ppm): 1.21(t, 6H), 1.87(s, 6H), 3.14(t, 4H), 5.01(s, 1H), 6.10(s, 2H), 6.27(s, 2H), 6.95(d, J=8 Hz, 1H), 7.47(d, J=8 Hz, 1H), 7.45 (m, 1H), 7.48(d, J=8 Hz, 1H), 7.85(t, 1H), 9.42(d, J=8 Hz, 1H); $^{13}$C NMR (400 MHz, CDCl$_3$), δ: 12.7, 19.8, 44.5, 66.04, 98.09, 103.78, 108.17, 123.98, 124.07, 126.58, 128.62, 134.97, 149.21, 152.64, 152.87, 165.87; TOF MS (ES): m/z Calcd for $C_{28}H_{28}N_4O_3^+$: 468.2161, Found: 468.2178.

(3) The Synthesis of RHg17:

The intermediate 6 (0.47 g, 1 mmol) was added into a 100 ml single-necked flask, and then absolute 30 ml and 4-aminodiphenylamine (0.74 g, 4 mmol) (excessive in amount) were added. The reaction mixture was stirred for 2 h at room temperature under nitrogen protection, and then the solvent was removed under reduced pressure. The product was purified through silica column chromatography with a mixture of petroleum ether (bp 60-90° C.) and ethyl acetate (v/v, 5/1) as elution solution to produce 0.53 g yellow solid RHg17 with a yield of 83%. $^1$H NMR (400 MHz CDCl$_3$) δ (ppm): 1.21(t, 6H), 1.87(s, 6H), 3.14(t, 4H), 4.23(s, 2H), 5.01(s, 1H), 6.10(s, 2H), 6.27(s, 2H), 7.09(m, 4H), 7.31(m, 4H), 7.47(m, 2H), 7.95(d, J=8 Hz, 1H), 8.01(d, J=8 Hz, 1H), 8.34(d, J=8 Hz, 1H), 9.77(s, 1H); $^{13}$C NMR (100 MHz, CDCl$_3$), δ: 12.7, 19.8, 44.5, 68.0, 100.1, 114.8, 119.9, 118.3, 119.1, 120.4, 123.2, 126.4, 128.3, 129.7, 131.3, 132.7, 138.0, 138.5, 139.5, 142.6, 147.5, 148.7, 163.0, 168.0; TOF MS (ES): m/z Calcd for $C_{20}H_{16}N_4O_2^+$: 344.1273, Found: 344.1250.

Example 38

Figure 25:
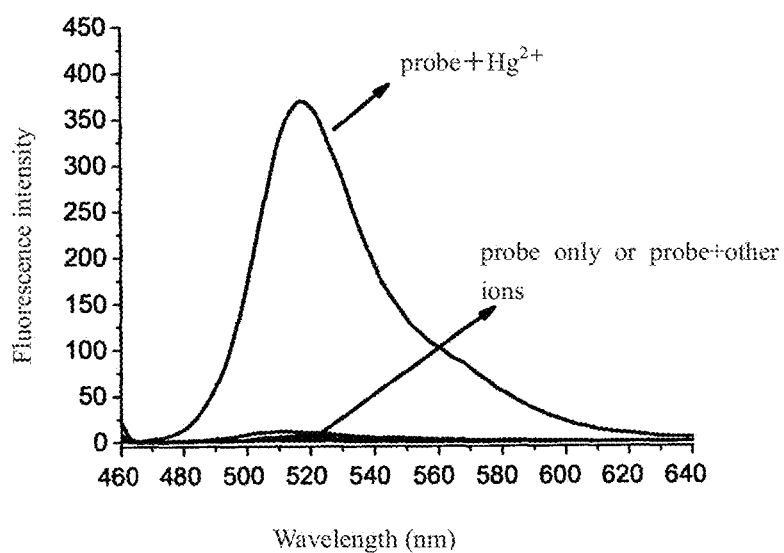
FIG. 25 is fluorescence emission spectra of fluorescence probe RHg17 coordinating $Hg^{2+}$ over other metal ions. Concentration of RHg17 is 5 μM, and concentrations of the metal ions are 50 equivalence ($Hg^{2+}$ is 15 equivalence). X-axis is wavelength (nm) and Y-axis is fluorescence intensity. The instrument is fluorospectrophotometer, model: LS 55.

The Selectivity Test of RHg17 to $Hg^{2+}$:

The synthesized compound RHg17 was adopted to test the selectivity to $Hg^{2+}$. RHg17 (5 μM) was added into ethanol aqueous solution (ethanol/water=1/1, v/v) containing metal ion (50 equivalence, except that $Hg^{2+}$ is 15 equivalence), and then the fluorescence spectrum was tested, the result is shown in FIG. 25. From FIG. 25, it can be seen that, RHg17 exhibits good selectivity to $Hg^{2+}$ and large fluorescence and UV-Vis absorption enhancement is induced by $Hg^{2+}$ without the interference from $Na^+$, $K^+$, $Ca^{2+}$, $Mg^{2+}$, $Cu^{2+}$ and so on. The instrument is fluorospectrophotometer, model: LS 55.

Example 39

The Synthesis of RHg18:

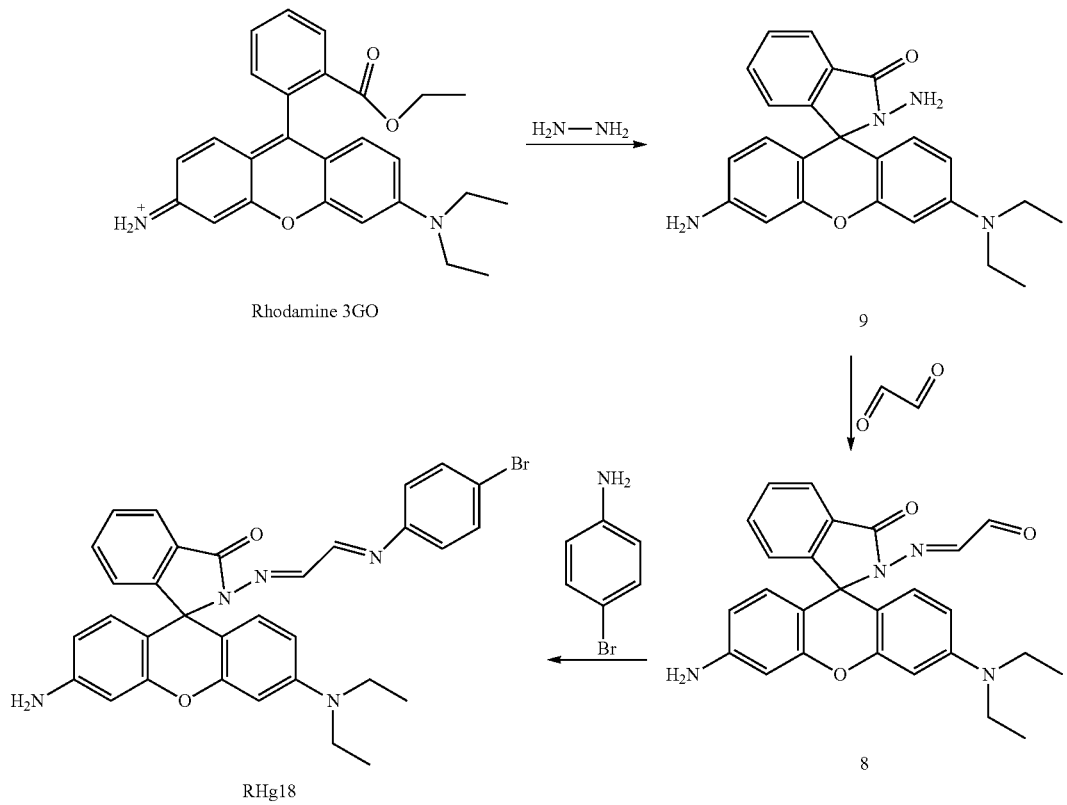

(1) The Synthesis of Intermediate 9:

Rhodamine 3GO (1.1 g, 2.5 mmol) was added into a 100 ml single-necked flask containing 30 ml ethanol. The mixture was stirred vigorously at room temperature, followed by dropwise addition of excessive amount of 85% hydrazine hydrate solution (3 ml). After finishing the addition of hydrazine hydrage, the mixture was refluxed for 2 h in air until the solution changed from purple to light brown in color and finally became clear. Then the solution was cooled down to room temperature and ethanol was removed under reduced pressure. After that, 50 ml HCl (1 M) was added to give a red solution, and then 70 ml NaOH aqueous solution (1 M) was added under stirring to adjust pH to 9 to 10 to form a large amount of precipitation. The precipitation was filtered and washed with 15 ml water for three times, then dried under vacuum and purified through column chromatography to produce 0.65 g intermediate 9, yield 65%. $^1$H NMR (400 MHz CDCl$_3$) δ (ppm): 1.18(t, 6H), 3.35(q, 4H), 3.62(s, 2H), 5.85(s, 4H), 6.14(d, J=8 Hz, 2H), 6.25(m, 4H), 7.10(d, J=8 Hz, 1H), 7.48(t, 2H), 8.02(d, J=8 Hz, 1H); $^{13}$C NMR (400 MHz, CDCl$_3$), δ: 12.7, 44.5, 66.04, 98.09, 103.78, 108.17, 123.98, 124.07, 126.58, 128.62, 134.97, 149.21, 152.64, 152.87, 165.87; TOF MS (ES): m/z Calcd for $C_{24}H_{24}N_4O_2^+$: 400.1899, Found: 400.1886.

(2) The Synthesis of Intermediate 8:

The intermediate 9 (0.40 g, 1.0 mmol) was added into a 100 ml single-necked flask, and then absolute ethanol 30 ml and 40% glyoxal aqueous solution (0.58 g, 4.0 mmol) (excessive in amount) were added. The reaction mixture was stirred for 2 h at room temperature under nitrogen protection, and then the solvent was removed under reduced pressure. The product was purified through silica column chromatography with a mixture of petroleum ether (bp 60 to 90° C.) and ethyl acetate (v/v, 5/1) as elution solution to produce 0.35 g yellow solid 8 with a yield of 79%. $^1$H NMR (400 MHz CDCl$_3$) δ (ppm): 1.18(t, 6H), 3.35(q, 4H), 3.62(s, 2H), 5.85(s, 2H), 6.14(d, J=8 Hz, 2H), 6.25(m, 4H), 7.10(d, J=8 Hz, 1H), 7.45(m, J=8 Hz, 1H), 7.48(t, 2H), 8.02 (d, J=8 Hz, 1H), 9.42(d, J=8 Hz, 1H); $^{13}$C NMR (400 MHz, CDCl$_3$), δ: 12.7, 44.5, 66.04, 98.09, 103.78, 108.17, 123.98, 124.07, 126.58, 128.62, 134.97, 141.22, 149.21, 152.64, 152.87, 165.87, 192.49; TOF MS (ES): m/z Calcd for $C_{26}H_{24}N_4O_3^+$: 440.1848, Found: 440.1862.

(3) The Synthesis of RHg18:

The intermediate 8 (0.44 g, 1 mmol) was added into a 100 ml single-necked flask, and then absolute 30 ml and 4-bromoaniline (0.68 g, 4 mmol) (excessive in amount) were added. The reaction mixture was stirred for 2 h at room temperature under nitrogen protection, and then the solvent was removed under reduced pressure. The product was purified through silica column chromatography with a mixture of petroleum ether (bp 60-90° C.) and ethyl acetate (v/v, 5/1) as elution solution to produce 0.48 g yellow solid RHg18 with a yield of 81%. $^1$H NMR (400 MHz CDCl$_3$) δ (ppm): 1.18(t, 6H), 3.35(q, 4H), 5.85(s, 2H), 6.27(d, J=8 Hz, 2H), 6.44(s, 2H), 6.54(d, J=8 Hz, 2H), 7.09(m, 3H), 7.47(m, 4H), 7.95(d, J=8 Hz, 1H), 8.01(d, J=8 Hz, 1H), 8.34(d, J=8 Hz, 1H); $^{13}$C NMR (100 MHz, CDCl$_3$), δ: 12.7, 44.5, 68.0, 103.1, 114.8, 121.3, 124.5, 126.4, 128.3, 131.3, 132.9, 139.5, 145.6, 147.5, 148.0, 151.8, 163.0, 168.0; TOF MS (ES): m/z Calcd for $C_{20}H_{16}N_4O_2^+$: 344.1273, Found: 344.1250.

Example 40

Figure 26:
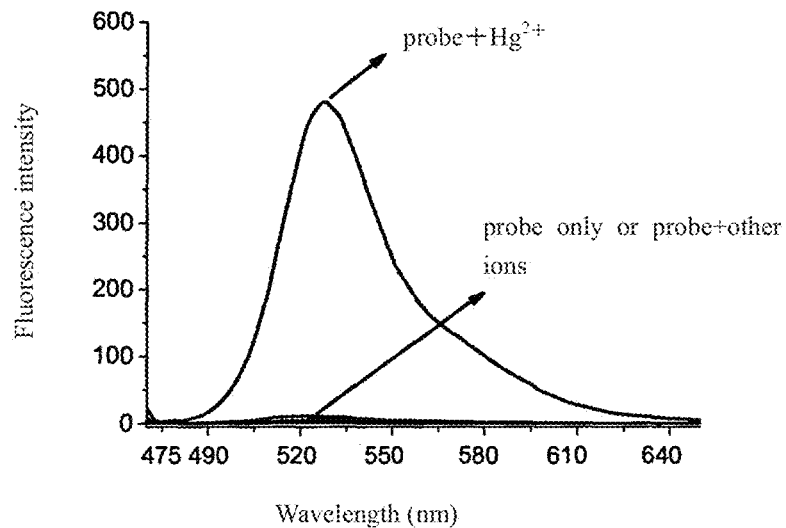
FIG. 26 is fluorescence emission spectra of fluorescence probe RHg18 coordinating $Hg^{2+}$ over other metal ions. Concentration of RHg18 is 5 μM, and concentrations of the metal ions are 50 equivalence ($Hg^{2+}$ is 15 equivalence). X-axis is wavelength (nm) and Y-axis is fluorescence intensity. The instrument is fluorospectrophotometer, model: LS 55.

The Selectivity Test of RHg18 to Hg$^{2+}$:

The synthesized compound RHg18 was adopted to test the selectivity to Hg$^{2+}$. RHg18 (5 μM) was added into ethanol aqueous solution (ethanol/water=1/1, v/v) containing metal ion (50 equivalence, except that Hg$^{2+}$ is 15 equivalence), and then the fluorescence spectrum was tested, the result is shown in FIG. 26. From FIG. 26, it can be seen that, RHg18 exhibits good selectivity to Hg$^{2+}$ and large fluorescence and UV-Vis absorption enhancement is induced by Hg$^{2+}$ without the interference from Na$^+$, K$^+$, Ca$^{2+}$, Mg$^{2+}$, Cu$^{2+}$ and so on. The instrument is fluorospectrophotometer, model: LS 55.

Example 41

The Synthesis of RHg19:

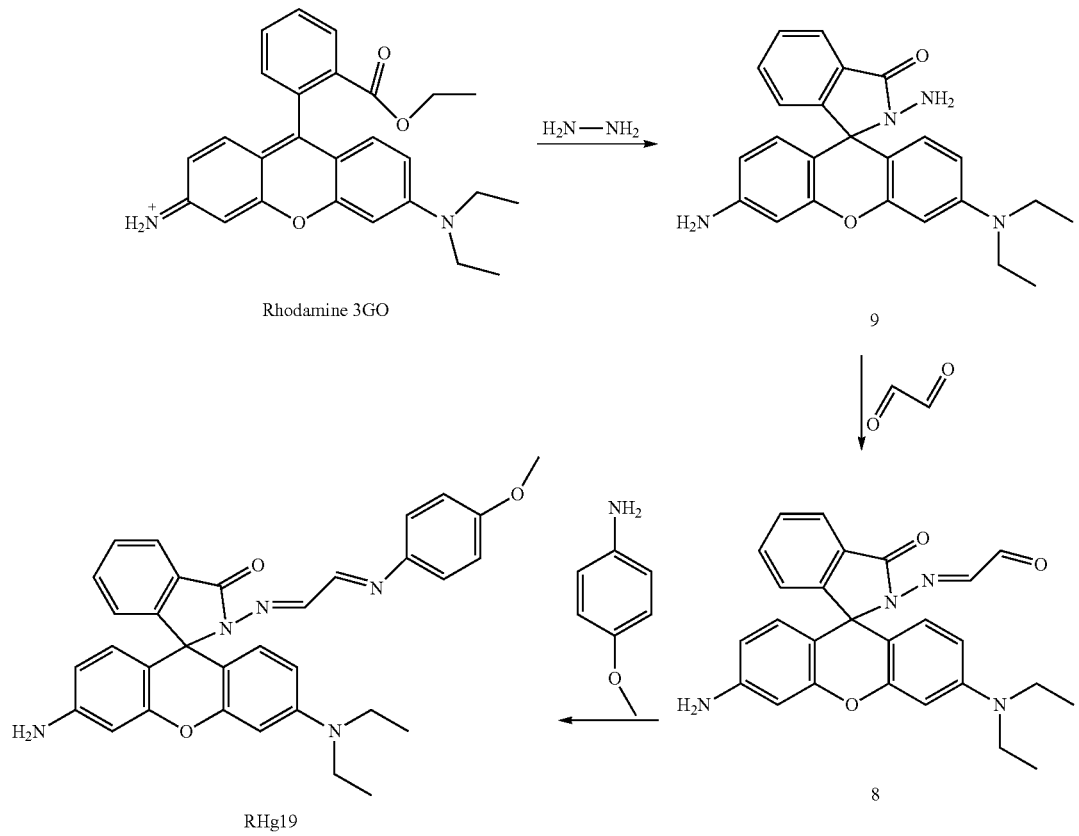

(1) The Synthesis of Intermediate 9:

Rhodamine 3GO (1.1 g, 2.5 mmol) was added into a 100 ml single-necked flask containing 30 ml ethanol. The mixture was stirred vigorously at room temperature, followed by dropwise addition of excessive amount of 85% hydrazine hydrate solution (3 ml). After finishing the addition of hydrazine hydrage, the mixture was refluxed for 2 h in air until the solution changed from purple to light brown in color and finally became clear. Then the solution was cooled down to room temperature and ethanol was removed under reduced pressure. After that, 50 ml HCl (1 M) was added to give a red solution, and then 70 ml NaOH aqueous solution (1 M) was added under stirring to adjust pH to 9 to 10 to form a large amount of precipitation. The precipitation was filtered and washed with 15 ml water for three times, then dried under vacuum and purified through column chromatography to produce 0.65 g intermediate 9, yield 65%. $^1$H NMR (400 MHz CDCl$_3$) δ (ppm): 1.18(t, 6H), 3.35(q, 4H), 3.62(s, 2H), 5.85(s, 4H), 6.14(d, J=8 Hz, 2H), 6.25(m, 4H), 7.10(d, J=8 Hz, 1H), 7.48(t, 2H), 8.02(d, J=8 Hz, 1H); $^{13}$C NMR (400 MHz, CDCl$_3$), δ: 12.7, 44.5, 66.04, 98.09, 103.78, 108.17, 123.98, 124.07, 126.58, 128.62, 134.97, 149.21, 152.64, 152.87, 165.87; TOF MS (ES): m/z Calcd for $C_{24}H_{24}N_4O_2^+$: 400.1899, Found: 400.1886.

(2) The Synthesis of Intermediate 8:

The intermediate 9 (0.40 g, 1.0 mmol) was added into a 100 ml single-necked flask, and then absolute ethanol 30 ml and 40% glyoxal aqueous solution (0.58 g, 4.0 mmol) (excessive in amount) were added. The reaction mixture was stirred for 2 h at room temperature under nitrogen protection, and then the solvent was removed under reduced pressure. The product was purified through silica column chromatography with a mixture of petroleum ether (bp 60 to 90° C.) and ethyl acetate (v/v, 5/1) as elution solution to produce 0.35 g yellow solid 8 with a yield of 79%. $^1$H NMR (400 MHz CDCl$_3$) δ (ppm): 1.18(t, 6H), 3.35(q, 4H), 3.62(s, 2H), 5.85(s, 2H), 6.14(d, J=8 Hz, 2H), 6.25(m, 4H), 7.10(d, J=8 Hz, 1H), 7.45(m, J=8 Hz, 1H), 7.48(t, 2H), 8.02(d, J=8 Hz, 1H), 9.42(d, J=8 Hz, 1H); $^{13}$C NMR (400 MHz, CDCl$_3$), δ: 12.7, 44.5, 66.04, 98.09, 103.78, 108.17, 123.98, 124.07, 126.58, 128.62, 134.97, 141.22, 149.21, 152.64, 152.87, 165.87, 192.49; TOF MS (ES): m/z Calcd for $C_{26}H_{24}N_4O_3^+$: 440.1848, Found: 440.1862.

(3) The Synthesis of RHg19:

The intermediate 8 (0.44 g, 1 mmol) was added into a 100 ml single-necked flask, and then absolute 30 ml and 4-methoxyaniline (0.49 g, 4 mmol) (excessive in amount) were added. The reaction mixture was stirred for 2 h at room temperature under nitrogen protection, and then the solvent was removed under reduced pressure. The product was purified through silica column chromatography with a mixture of petroleum ether (bp 60-90° C.) and ethyl acetate (v/v, 5/1) as elution solution to produce 0.47 g yellow solid RHg19 with a yield of 87%. $^1$H NMR (400 MHz CDCl$_3$) δ (ppm): 1.18(t, 6H), 3.35(q, 4H), 3.77(s, 3H), 5.85(s, 2H), 6.27(d, J=8 Hz, 2H), 6.44(s, 2H), 6.54(d, J=8 Hz, 2H), 7.09(m, 3H), 7.20(d, J=8 Hz, 2H), 7.47(m, 2H), 7.95(d, J=8 Hz, 1H), 8.01(d, J=8 Hz, 1H), 8.34(d, J=8 Hz, 1H); $^{13}$C NMR (400 MHz, CDCl$_3$), δ: 12.7, 44.5, 55.8, 68.0, 103.0, 109.9, 115.6, 123.3, 128.7, 132.7, 139.5, 141.3, 145.6, 147.5, 159.1, 163.0, 168.0; TOF MS (ES): m/z Calcd for $C_{20}H_{16}N_4O_2^+$: 344.1273, Found: 344.1250.

Example 42

Figure 27:
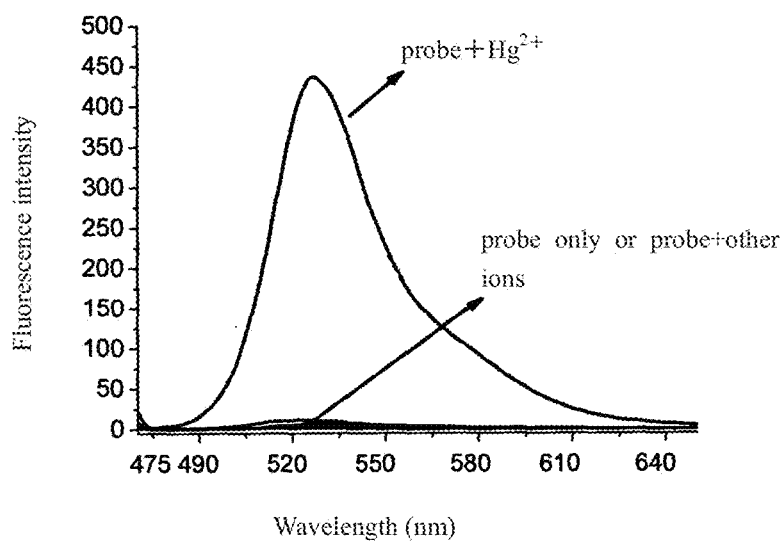
FIG. 27 is fluorescence emission spectra of fluorescence probe RHg19 coordinating $Hg^{2+}$ over other metal ions. Concentration of RHg19 is 5 μM, and concentrations of the metal ions are 50 equivalence ($Hg^{2+}$ is 15 equivalence). X-axis is wavelength (nm) and Y-axis is fluorescence intensity. The instrument is fluorospectrophotometer, model: LS 55.

The Selectivity Test of RHg19 to $Hg^{2+}$:

The synthesized compound RHg19 was adopted to test the selectivity to $Hg^{2+}$. RHg19 (5 μM) was added into ethanol aqueous solution (ethanol/water=1/1, v/v) containing metal ion (50 equivalence, except that $Hg^{2+}$ is 15 equivalence), and then the fluorescence spectrum was tested, the result is shown in FIG. 27. From FIG. 27, it can be seen that, RHg19 exhibits good selectivity to $Hg^{2+}$ and large fluorescence and UV-Vis absorption enhancement is induced by $Hg^{2+}$ without the interference from $Na^+$, $K^+$, $Ca^{2+}$, $Mg^{2+}$, $Cu^{2+}$ and so on. The instrument is fluorospectrophotometer, model: LS 55.

Example 43

The Synthesis of RHg20:

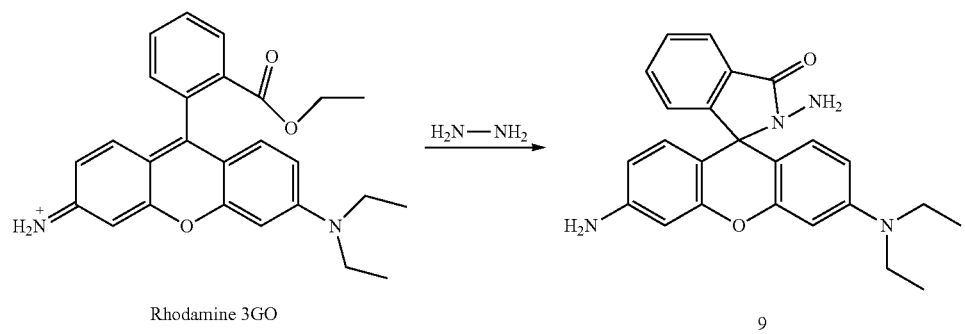

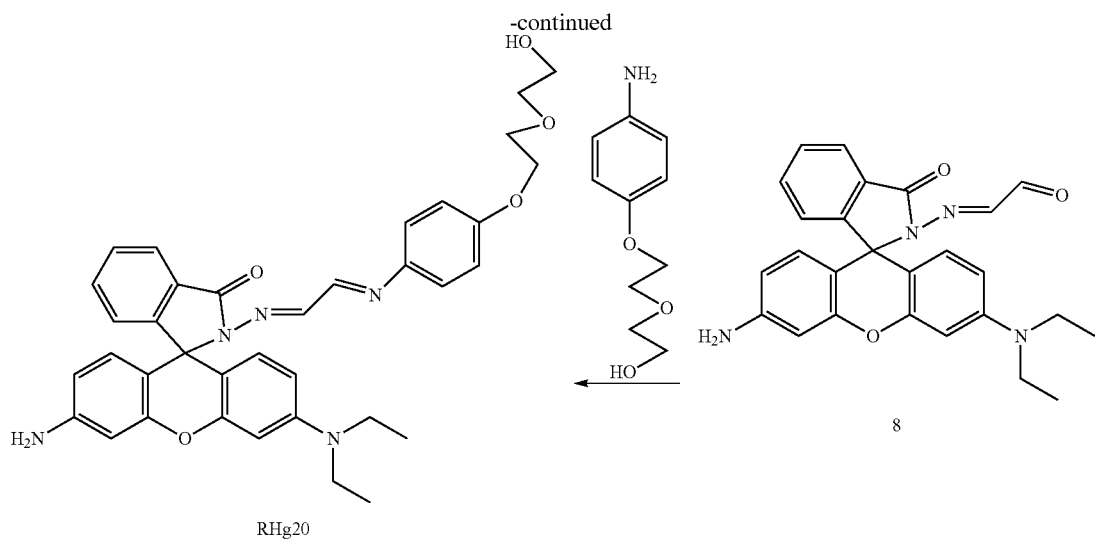

-continued

RHg20

8

(1) The Synthesis of Intermediate 9:

Rhodamine 3GO (1.1 g, 2.5 mmol) was added into a 100 ml single-necked flask containing 30 ml ethanol. The mixture was stirred vigorously at room temperature, followed by dropwise addition of excessive amount of 85% hydrazine hydrate solution (3 ml). After finishing the addition of hydrazine hydrage, the mixture was refluxed for 2 h in air until the solution changed from purple to light brown in color and finally became clear. Then the solution was cooled down to room temperature and ethanol was removed under reduced pressure. After that, 50 ml HCl (1 M) was added to give a red solution, and then 70 ml NaOH aqueous solution (1 M) was added under stirring to adjust pH to 9 to 10 to form a large amount of precipitation. The precipitation was filtered and washed with 15 ml water for three times, then dried under vacuum and purified through column chromatography to produce 0.65 g intermediate 9, yield 65%. $^1$H NMR (400 MHz CDCl$_3$) δ (ppm): 1.18(t, 6H), 3.35(q, 4H), 3.62(s, 2H), 5.85(s, 4H), 6.14(d, J=8 Hz, 2H), 6.25(m, 4H), 7.10(d, J=8 Hz, 1H), 7.48(t, 2H), 8.02(d, J=8 Hz, 1H); $^{13}$C NMR (400 MHz, CDCl$_3$), δ: 12.7, 44.5, 66.04, 98.09, 103.78, 108.17, 123.98, 124.07, 126.58, 128.62, 134.97, 149.21, 152.64, 152.87, 165.87; TOF MS (ES): m/z Calcd for $C_{24}H_{24}N_4O_2^+$: 400.1899, Found: 400.1886.

(2) The Synthesis of Intermediate 8:

The intermediate 9 (0.40 g, 1.0 mmol) was added into a 100 ml single-necked flask, and then absolute ethanol 30 ml and 40% glyoxal aqueous solution (0.58 g, 4.0 mmol) (excessive in amount) were added. The reaction mixture was stirred for 2 h at room temperature under nitrogen protection, and then the solvent was removed under reduced pressure. The product was purified through silica column chromatography with a mixture of petroleum ether (bp 60 to 90° C.) and ethyl acetate (v/v, 5/1) as elution solution to produce 0.35 g yellow solid 8 with a yield of 79%. $^1$H NMR (400 MHz CDCl$_3$) δ (ppm): 1.18(t, 6H), 3.35(q, 4H), 3.62(s, 2H), 5.85(s, 2H), 6.14(d, J=8 Hz, 2H), 6.25(m, 4H), 7.10(d, J=8 Hz, 1H), 7.45(m, J=8 Hz, 1H), 7.48(t, 2H), 8.02(d, J=8 Hz, 1H), 9.42(d, J=8 Hz, 1H); $^{13}$C NMR (400 MHz, CDCl$_3$), δ: 12.7, 44.5, 66.04, 98.09, 103.78, 108.17, 123.98, 124.07, 126.58, 128.62, 134.97, 141.22, 149.21, 152.64, 152.87, 165.87, 192.49; TOF MS (ES): m/z Calcd for $C_{26}H_{24}N_4O_3^+$: 440.1848, Found: 440.1862.

(3) The Synthesis of RHg20:

The intermediate 8 (0.44 g, 1 mmol) was added into a 100 ml single-necked flask, and then absolute 30 ml and 2-(2-(4-aminophenoxy)ethoxy)ethanol (0.79 g, 4 mmol) (excessive in amount) were added. The reaction mixture was stirred for 2 h at room temperature under nitrogen protection, and then the solvent was removed under reduced pressure. The product was purified through silica column chromatography with a mixture of petroleum ether (bp 60-90° C.) and ethyl acetate (v/v, 5/1) as elution solution to produce 0.43 g yellow solid RHg20 with a yield of 70%. $^1$H NMR (400 MHz CDCl$_3$) δ (ppm): 1.18(t, 6H), 3.35(q, 4H), 3.56(t, 2H), 3.70(t, 2H), 3.79(t, 2H), 4.11(t, 2H), 4.78(s, 1H), 5.85(s, 2H), 6.14(d, J=8 Hz, 2H), 6.25(m, 4H), 7.10(d, J=8 Hz, 1H), 7.48(t, 2H), 8.02 (d, J=8 Hz, 1H); $^{13}$C NMR (400 MHz, CDCl$_3$), δ: 12.7, 44.5, 61.3, 68.0, 70.0, 72.6, 103.1, 115.7, 122.9, 128.3, 131.0, 132.7, 135.9, 140.6, 145.6, 147.5, 151.8, 155.9, 168.3; TOF MS (ES): m/z Calcd for $C_{20}H_{16}N_4O_2^+$: 344.1273, Found: 344.1250.

Example 44

Figure 28:
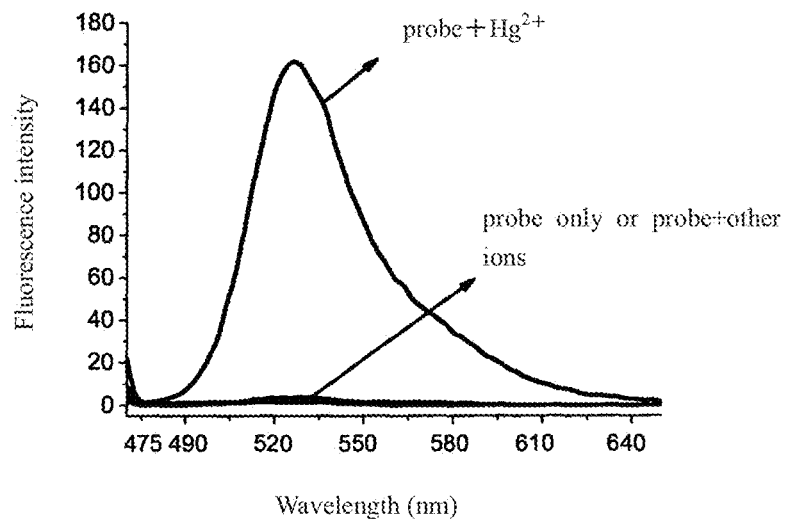
FIG. 28 is fluorescence emission spectra of fluorescence probe RHg20 coordinating $Hg^{2+}$ over other metal ions. Concentration of RHg20 is 5 μM, and concentrations of the metal ions are 50 equivalence ($Hg^{2+}$ is 15 equivalence). X-axis is wavelength (nm) and Y-axis is fluorescence intensity. The instrument is fluorospectrophotometer, model: LS 55.

The Selectivity Test of RHg20 to Hg$^{2+}$:

The synthesized compound RHg20 was adopted to test the selectivity to Hg$^{2+}$. RHg20 (5 μM) was added into ethanol aqueous solution (ethanol/water=1/1, v/v) containing metal ion (50 equivalence, except that Hg$^{2+}$ is 15 equivalence), and then the fluorescence spectrum was tested, the result is shown in FIG. 28. From FIG. 28, it can be seen that, RHg20 exhibits good selectivity to Hg$^{2+}$ and large fluorescence and UV-Vis absorption enhancement is induced by Hg$^{2+}$ without the interference from Na$^+$, K$^+$, Ca$^{2+}$, Mg$^{2+}$, Cu$^{2+}$ and so on. The instrument is fluorospectrophotometer, model: LS 55.

Example 45

The Synthesis of RHg21:

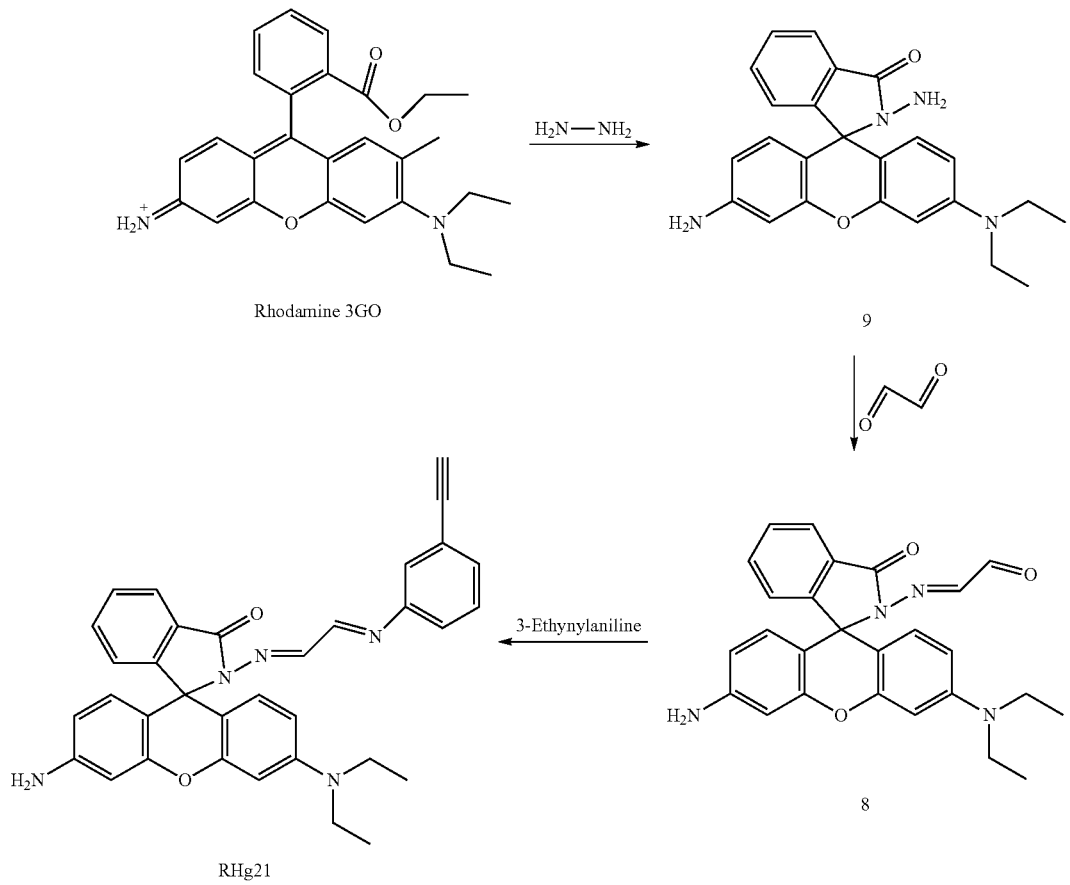

(1) The Synthesis of Intermediate 9:

Rhodamine 3GO (1.1 g, 2.5 mmol) was added into a 100 ml single-necked flask containing 30 ml ethanol. The mixture was stirred vigorously at room temperature, followed by dropwise addition of excessive amount of 85% hydrazine hydrate solution (3 ml). After finishing the addition of hydrazine hydrage, the mixture was refluxed for 2 h in air until the solution changed from purple to light brown in color and finally became clear. Then the solution was cooled down to room temperature and ethanol was removed under reduced pressure. After that, 50 ml HCl (1 M) was added to give a red solution, and then 70 ml NaOH aqueous solution (1 M) was added under stirring to adjust pH to 9 to 10 to form a large amount of precipitation. The precipitation was filtered and washed with 15 ml water for three times, then dried under vacuum and purified through column chromatography to produce 0.65 g intermediate 9, yield 65%. $^1$H NMR (400 MHz CDCl$_3$) δ (ppm): 1.18(t, 6H), 3.35(q, 4H), 3.62(s, 2H), 5.85(s, 4H), 6.14(d, J=8 Hz, 2H), 6.25(m, 4H), 7.10(d, J=8 Hz, 1H), 7.48(t, 2H), 8.02(d, J=8 Hz, 1H); $^{13}$C NMR (400 MHz, CDCl$_3$), δ: 12.7, 44.5, 66.04, 98.09, 103.78, 108.17, 123.98, 124.07, 126.58, 128.62, 134.97, 149.21, 152.64, 152.87, 165.87; TOF MS (ES): m/z Calcd for C$_{24}$H$_{24}$N$_4$O$_2$$^+$: 400.1899, Found: 400.1886.

(2) The Synthesis of Intermediate 8:

The intermediate 9 (0.40 g, 1.0 mmol) was added into a 100 ml single-necked flask, and then absolute ethanol 30 ml and 40% glyoxal aqueous solution (0.58 g, 4.0 mmol) (excessive in amount) were added. The reaction mixture was stirred for 2 h at room temperature under nitrogen protection, and then the solvent was removed under reduced pressure. The product was purified through silica column chromatography with a mixture of petroleum ether (bp 60 to 90° C.) and ethyl acetate (v/v, 5/1) as elution solution to produce 0.35 g yellow solid 8 with a yield of 79%. $^1$H NMR (400 MHz CDCl$_3$) δ (ppm): 1.18(t, 6H), 3.35(q, 4H), 3.62(s, 2H), 5.85(s, 2H), 6.14(d, J=8 Hz, 2H), 6.25(m, 4H), 7.10(d, J=8 Hz, 1H), 7.45(m, J=8 Hz, 1H), 7.48(t, 2H), 8.02(d, J=8 Hz, 1H), 9.42 (d, J=8 Hz, 1H); $^{13}$C NMR (400 MHz, CDCl$_3$), δ: 12.7, 44.5, 66.04, 98.09, 103.78, 108.17, 123.98, 124.07, 126.58, 128.62, 134.97, 141.22, 149.21, 152.64, 152.87, 165.87, 192.49; TOF MS (ES): m/z Calcd for C$_{26}$H$_{24}$N$_4$O$_3$$^+$: 440.1848, Found: 440.1862.

(3) The Synthesis of RHg21:

The intermediate 8 (0.44 g, 1 mmol) was added into a 100 ml single-necked flask, and then absolute 30 ml and 3-ethynylaniline (0.47 g, 4 mmol) (excessive in amount) were added. The reaction mixture was stirred for 2 h at room temperature under nitrogen protection, and then the solvent was removed under reduced pressure. The product was purified through silica column chromatography with a mixture of petroleum ether (bp 60-90° C.) and ethyl acetate (v/v, 5/1) as elution solution to produce 0.40 g yellow solid RHg21 with a yield of 75%. $^1$H NMR (400 MHz CDCl$_3$) δ (ppm): 1.18(t, 6H), 3.06(s, 1H), 3.35(q, 4H), 5.85(s, 2H), 6.27 (d, J=8 Hz, 2H), 6.44(s, 2H), 6.54(d, J=8 Hz, 2H), 7.09(d, J=8 Hz, 1H), 7.20(m, 2H), 7.47(m, 4H), 7.95(d, J=8 Hz, 1H), 8.01(d, J=8

Hz, 1H), 8.34(d, J=8 Hz, 1H); $^{13}$C NMR (100 MHz, CDCl$_3$), δ: 12.7, 44.5, 68.0, 79.9, 82.3, 103.1, 109.9, 114.8, 122.0, 124.0, 126.4, 127.8, 128.3, 129.7, 130.8, 131.3, 132.7, 139.5, 145.6, 147.5, 148.6, 151.8, 163.0; TOF MS (ES): m/z Calcd for $C_{30}H_{21}N_5O_2{}^+$: 344.1273, Found: 344.1250.

Example 46

Figure 29:
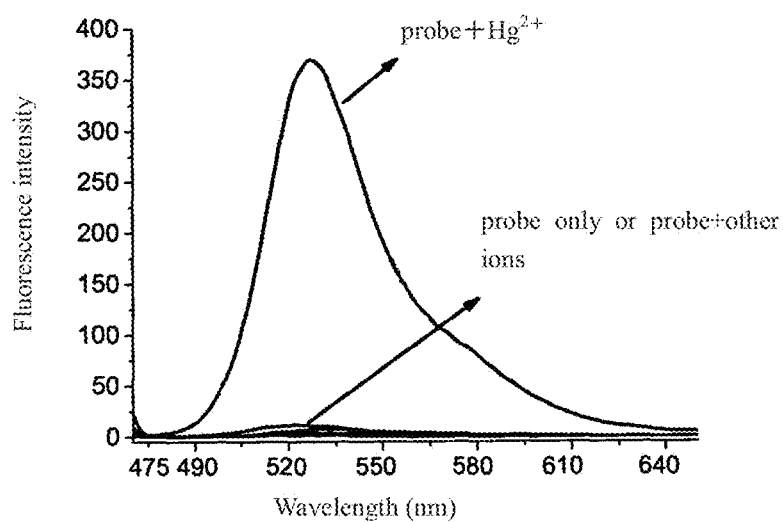
FIG. 29 is fluorescence emission spectra of fluorescence probe RHg21 coordinating $Hg^{2+}$ over other metal ions. Concentration of RHg21 is 5 μM, and concentrations of the metal ions are 50 equivalence ($Hg^{2+}$ is 15 equivalence). X-axis is wavelength (nm) and Y-axis is fluorescence intensity. The instrument is fluorospectrophotometer, model: LS 55.

The Selectivity Test of RHg21 to Hg$^{2+}$:

The synthesized compound RHg21 was adopted to test the selectivity to Hg$^{2+}$. RHg21 (5 μM) was added into ethanol aqueous solution (ethanol/water=1/1, v/v) containing metal ion (50 equivalence, except that Hg$^{2+}$ is 15 equivalence), and then the fluorescence spectrum was tested, the result is shown in FIG. 29. From FIG. 29, it can be seen that, RHg21 exhibits good selectivity to Hg$^{2+}$ and large fluorescence and UV-Vis absorption enhancement is induced by Hg$^{2+}$ without the interference from Na$^+$, K$^+$, Ca$^{2+}$, Mg$^{2+}$, Cu$^{2+}$ and so on. The instrument is fluorospectrophotometer, model: LS 55.

Example 47

The Synthesis of RHg22:

zine hydrage, the mixture was refluxed for 2 h in air until the solution changed from purple to light brown in color and finally became clear. Then the solution was cooled down to room temperature and ethanol was removed under reduced pressure. After that, 50 ml HCl (1 M) was added to give a red solution, and then 70 ml NaOH aqueous solution (1 M) was added under stirring to adjust pH to 9 to 10 to form a large amount of precipitation. The precipitation was filtered and washed with 15 ml water for three times, then dried under vacuum and purified through column chromatography to produce 0.52 g intermediate 11, yield 60%. $^1$H NMR (400 MHz CDCl$_3$) δ (ppm): 3.62(s, 2H), 5.85(s, 4H), 6.14(d, J=8 Hz, 2H), 6.25(m, 4H), 7.10(d, J=8 Hz, 1H), 7.48(t, 2H), 8.02(d, J=8 Hz, 1H); $^{13}$C NMR (400 MHz, CDCl$_3$), δ: 66.04, 98.09, 103.78, 108.17, 123.98, 124.07, 126.58, 128.62, 134.97, 149.21, 152.64, 152.87, 165.87; TOF MS (ES): m/z Calcd for $C_{20}H_{17}N_4O_2{}^+$: 345.1346, Found: 345.1351.

(2) The Synthesis of Intermediate 10:

The intermediate 11 (0.34 g, 1.0 mmol) was added into a 100 ml single-necked flask, and then absolute ethanol 30 ml and 40% glyoxal aqueous solution (0.58 g, 4.0 mmol) (exces-

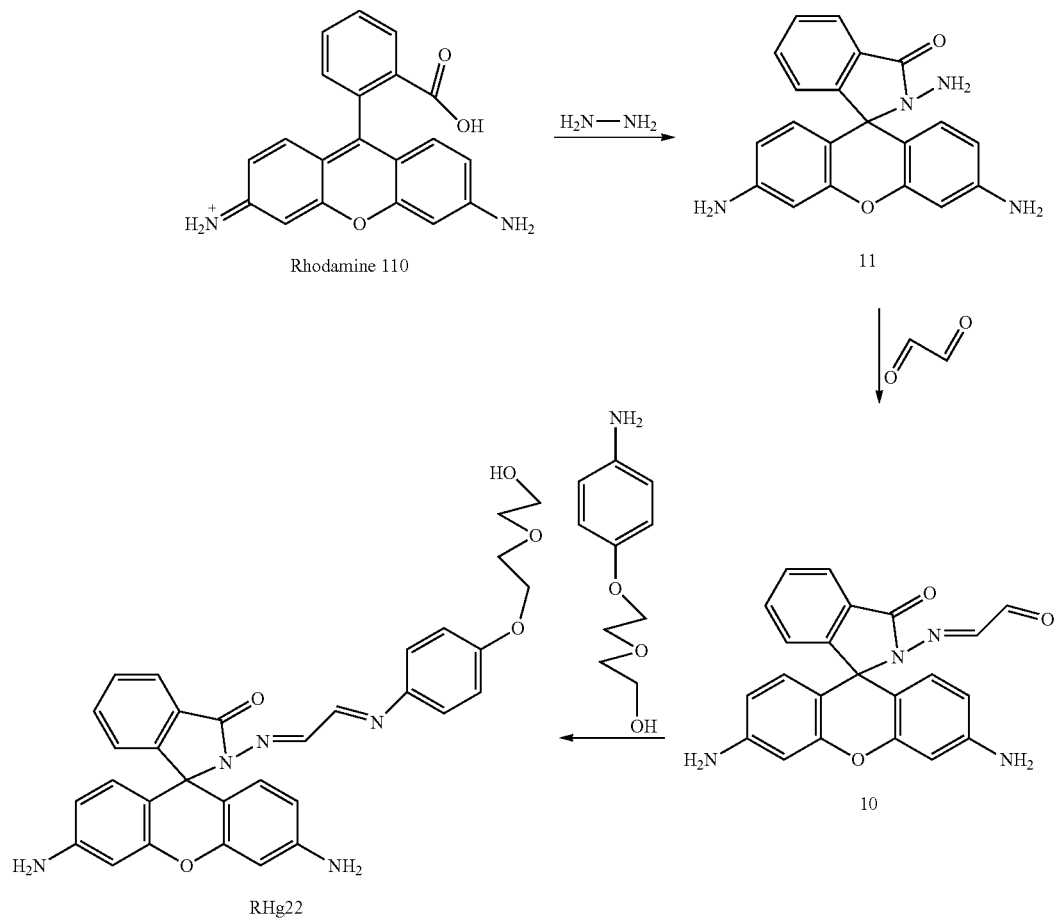

Figure 30:
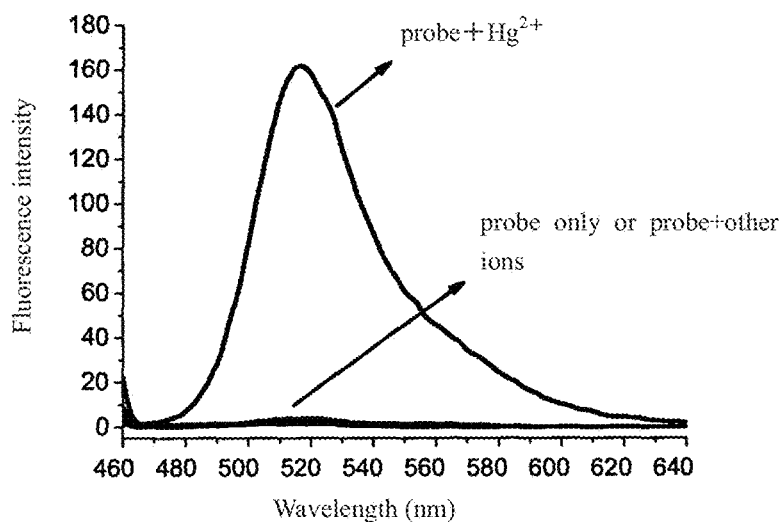
FIG. 30 is fluorescence emission spectra of fluorescence probe RHg22 coordinating $Hg^{2+}$ over other metal ions. Concentration of RHg22 is 5 μM, and concentrations of the metal ions are 50 equivalence ($Hg^{2+}$ is 15 equivalence). X-axis is wavelength (nm) and Y-axis is fluorescence intensity. The instrument is fluorospectrophotometer, model: LS 55.

(1) The Synthesis of Intermediate 11:

Rhodamine 110 (0.9 g, 2.5 mmol) was added into a 100 ml single-necked flask containing 30 ml ethanol. The mixture was stirred vigorously at room temperature, followed by dropwise addition of excessive amount of 85% hydrazine hydrate solution (3 ml). After finishing the addition of hydrasive in amount) were added. The reaction mixture was stirred for 2 h at room temperature under nitrogen protection, and then the solvent was removed under reduced pressure. The product was purified through silica column chromatography with a mixture of petroleum ether (bp 60 to 90° C.) and ethyl acetate (v/v, 5/1) as elution solution to produce 0.31 g yellow solid 10 with a yield of 81%. $^1$H NMR (400 MHz CDCl$_3$) δ (ppm): 5.85(s, 4H), 6.14(d, J=8 Hz, 2H), 6.25(m, 4H), 7.10(d, J=8 Hz, 1H), 7.45(m, J=8 Hz, 1H), 7.48(t, 2H), 8.02(d, J=8 Hz, 1H), 9.42(d, J=8 Hz, 1H); $^{13}$C NMR (400 MHz, CDCl$_3$), δ: 66.04, 98.09, 103.78, 108.17, 123.98, 124.07, 126.58, 128.62, 134.97, 141.22, 149.21, 152.64, 152.87, 165.87, 192.49; TOF MS (ES): m/z Calcd for C$_{22}$H$_{17}$N$_4$O$_3$$^+$: 385.1295, Found: 385.1283.

in FIG. 30. From FIG. 30, it can be seen that, RHg22 exhibits good selectivity to Hg$^{2+}$ and large fluorescence and UV-Vis absorption enhancement is induced by Hg$^{2+}$ without the interference from Na$^+$, K$^+$, Ca$^{2+}$, Mg$^{2+}$, Cu$^{2+}$ and so on. The instrument is fluorospectrophotometer, model: LS 55.

Example 49

The Synthesis of RHg23:

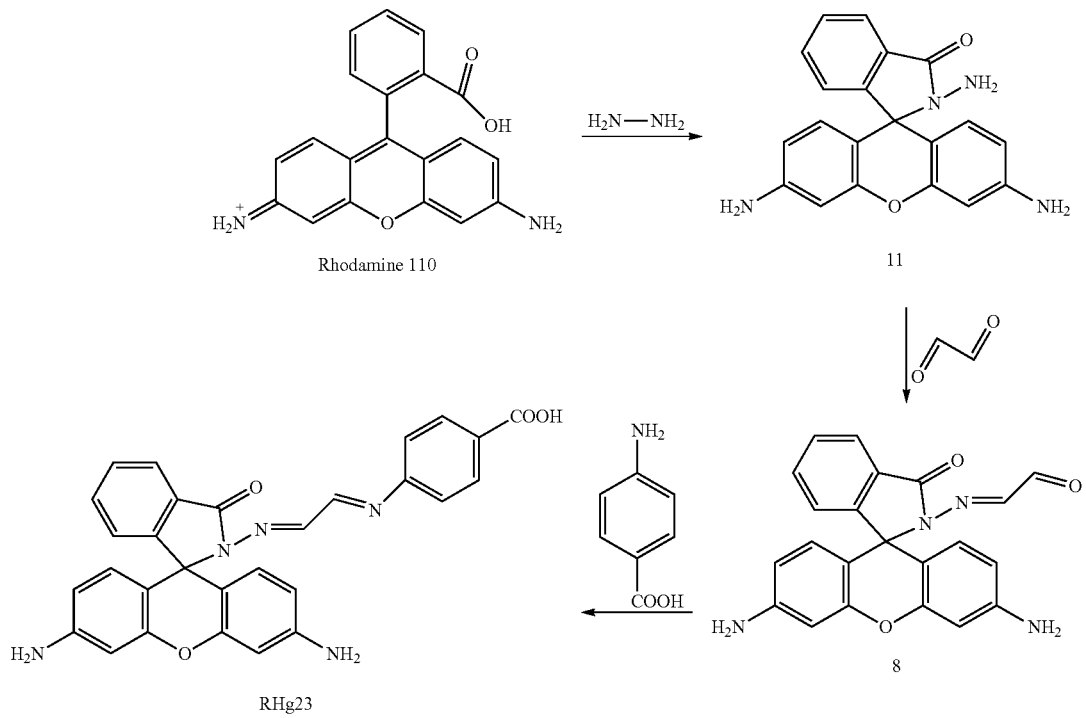

(3) The Synthesis of RHg22:

The intermediate 10 (0.38 g, 1 mmol) was added into a 100 ml single-necked flask, and then absolute 30 ml and 2-(2-(4-aminophenoxy)ethoxy)ethanol (0.79 g, 4 mmol) (excessive in amount) were added. The reaction mixture was stirred for 2 h at room temperature under nitrogen protection, and then the solvent was removed under reduced pressure. The product was purified through silica column chromatography with a mixture of petroleum ether (bp 60-90° C.) and ethyl acetate (v/v, 5/1) as elution solution to produce 0.44 g yellow solid RHg22 with a yield of 76%, $^1$H NMR (400 MHz CDCl$_3$) δ (ppm): 3.56(t, 2H), 3.70(t, 2H), 3.79(t, 2H), 4.11(t, 2H), 4.78 (s, 1H), 5.85(s, 4H), 6.14(d, J=8 Hz, 2H), 6.25(m, 4H), 7.10 (d, J=8 Hz, 1H), 7.48(t, 2H), 8.02(d, J=8 Hz, 1H); $^{13}$C NMR (400 MHz, CDCl$_3$), δ: 61.3, 68.0, 70.0, 72.6, 103.1, 115.7, 122.9, 128.3, 131.0, 132.7, 135.9, 140.6, 145.6, 147.5, 151.8, 155.9, 168.3; TOF MS (ES): m/z Calcd for C$_{32}$H$_{30}$H$_5$O$_5$$^+$: 564.2241, Found: 564.2259.

Example 48

The Selectivity Test of RHg22 to Hg$^{2+}$:

The synthesized compound RHg22 was adopted to test the selectivity to Hg$^{2+}$. RHg22 (5 μM) was added into ethanol aqueous solution (ethanol/water=1/1, v/v) containing metal ion (50 equivalence, except that Hg$^{2+}$ is 15 equivalence), and then the fluorescence spectrum was tested, the result is shown (1) Synthesis of Intermediate 11:

Rhodamine 110 (0.9 g, 2.5 mmol) was added into a 100 ml single-necked flask containing 30 ml ethanol. The mixture was stirred vigorously at room temperature, followed by dropwise addition of excessive amount of 85% hydrazine hydrate solution (3 ml). After finishing the addition of hydrazine hydrage, the mixture was refluxed for 2 h in air until the solution changed from purple to light brown in color and finally became clear. Then the solution was cooled down to room temperature and ethanol was removed under reduced pressure. After that, 50 ml HCl (1 M) was added to give a red solution, and then 70 ml NaOH aqueous solution (1 M) was added under stirring to adjust pH to 9 to 10 to form a large amount of precipitation. The precipitation was filtered and washed with 15 ml water for three times, then dried under vacuum and purified through column chromatography to produce 0.52 g intermediate 11, yield 60%. $^1$H NMR (400 MHz CDCl$_3$) δ (ppm): 3.62(s, 2H), 5.85(s, 4H), 6.14(d, J=8 Hz, 2H), 6.25(m, 4H), 7.10(d, J=8 Hz, 1H), 7.48(t, 2H), 8.02(d, J=8 Hz, 1H); $^{13}$C NMR (400 MHz, CDCl$_3$), δ: 66.04, 98.09, 103.78, 108.17, 123.98, 124.07, 126.58, 128.62, 134.97, 149.21, 152.64, 152.87, 165.87; TOF MS (ES): m/z Calcd for C$_{20}$H$_{17}$N$_4$O$_2$$^+$: 345.1346, Found: 345.1351.

(2) The Synthesis of Intermediate 10:

The intermediate 11 (0.34 g, 1.0 mmol) was added into a 100 ml single-necked flask, and then absolute ethanol 30 ml and 40% glyoxal aqueous solution (0.58 g, 4.0 mmol) (excessive in amount) were added. The reaction mixture was stirred for 2 h at room temperature under nitrogen protection, and then the solvent was removed under reduced pressure. The product was purified through silica column chromatography with a mixture of petroleum ether (bp 60 to 90° C.) and ethyl acetate (v/v, 5/1) as elution solution to produce 0.31 g yellow solid 10 with a yield of 81%. $^1$H NMR (400 MHz CDCl$_3$) δ (ppm): 5.85(s, 4H), 6.14(d, J=8 Hz, 2H), 6.25(m, 4H), 7.10(d, J=8 Hz, 1H), 7.45(m, J=8 Hz, 1H), 7.48(t, 2H), 8.02(d, J=8 Hz, 1H), 9.42(d, J=8 Hz, 1H); $^{13}$C NMR (400 MHz, CDCl$_3$), δ: 66.04, 98.09, 103.78, 108.17, 123.98, 124.07, 126.58, 128.62, 134.97, 141.22, 149.21, 152.64, 152.87, 165.87, 192.49; TOF MS (ES): m/z Calcd for C$_{22}$H$_{17}$N$_4$O$_3^+$: 385.1295, Found: 385.1283.

(3) The Synthesis of RHg23:

The intermediate 10 (0.38 g, 1 mmol) was added into a 100 ml single-necked flask, and then absolute 30 ml and 4-aminobenzoic acid (0.55 g, 4 mmol) (excessive in amount) were added. The reaction mixture was stirred for 2 h at room temperature under nitrogen protection, and then the solvent was removed under reduced pressure. The product was purified through silica column chromatography with a mixture of petroleum ether (bp 60-90° C.) and ethyl acetate (v/v, 5/1) as elution solution to produce 0.41 g yellow solid RHg23 with a yield of 82%. $^1$H NMR (400 MHz CDCl$_3$) δ (ppm): 5.85(s, 4H), 6.27(d, J=8 Hz, 2H), 6.44(s, 2H), 6.54(d, J=8 Hz, 2H), 7.09(d, J=8 Hz, 1H), 7.47(m, 4H), 7.95(d, J=8 Hz, 1H), 8.01 (d, J=8 Hz, 1H), 8.18(d, J=8 Hz, 2H), 8.34(d, J=8 Hz, 1H), 12.79(s, 1H); $^{13}$C NMR (400 MHz, CDCl$_3$), δ: 68.0, 103.1, 109.9, 114.8, 122.2, 126.4, 128.7, 131.6, 139.5, 145.6, 147.5, 151.8, 154.2, 163.0, 168.0, 169.3; TOF MS (ES): m/z Calcd for C$_{29}$H$_{22}$N$_5$O$_4^+$: 504.1666, Found: 504.1685.

Example 50

Figure 31:
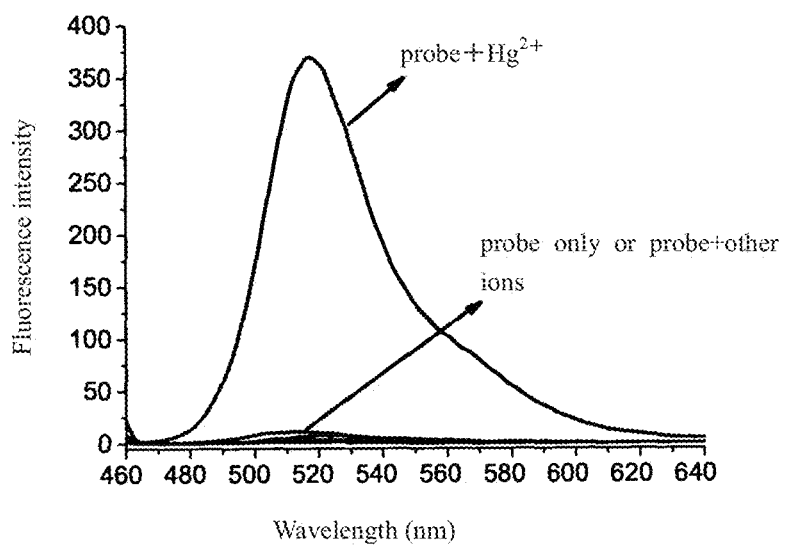
FIG. 31 is fluorescence emission spectra of fluorescence probe RHg23 coordinating $Hg^{2+}$ over other metal ions. Concentration of RHg23 is 5 μM, and concentrations of the metal ions are 50 equivalence ($Hg^{2+}$ is 15 equivalence). X-axis is wavelength (nm) and Y-axis is fluorescence intensity. The instrument is fluorospectrophotometer, model: LS 55.

The Selectivity Test of RHg23 to Hg$^{2+}$:

The synthesized compound RHg23 was adopted to test the selectivity to Hg$^{2+}$. RHg23 (5 μM) was added into ethanol aqueous solution (ethanol/water=1/1, v/v) containing metal ion (50 equivalence, except that Hg$^{2+}$ is 15 equivalence), and then the fluorescence spectrum was tested, the result is shown in FIG. 31. From FIG. 31, it can be seen that, RHg23 exhibits good selectivity to Hg$^{2+}$ and large fluorescence and UV-Vis absorption enhancement is induced by Hg$^{2+}$ without the interference from Na$^+$, K$^+$, Ca$^{2+}$, Mg$^{2+}$, Cu$^{2+}$ and so on. The instrument is fluorospectrophotometer, model: LS 55.

Example 51

The Synthesis of RHg24:

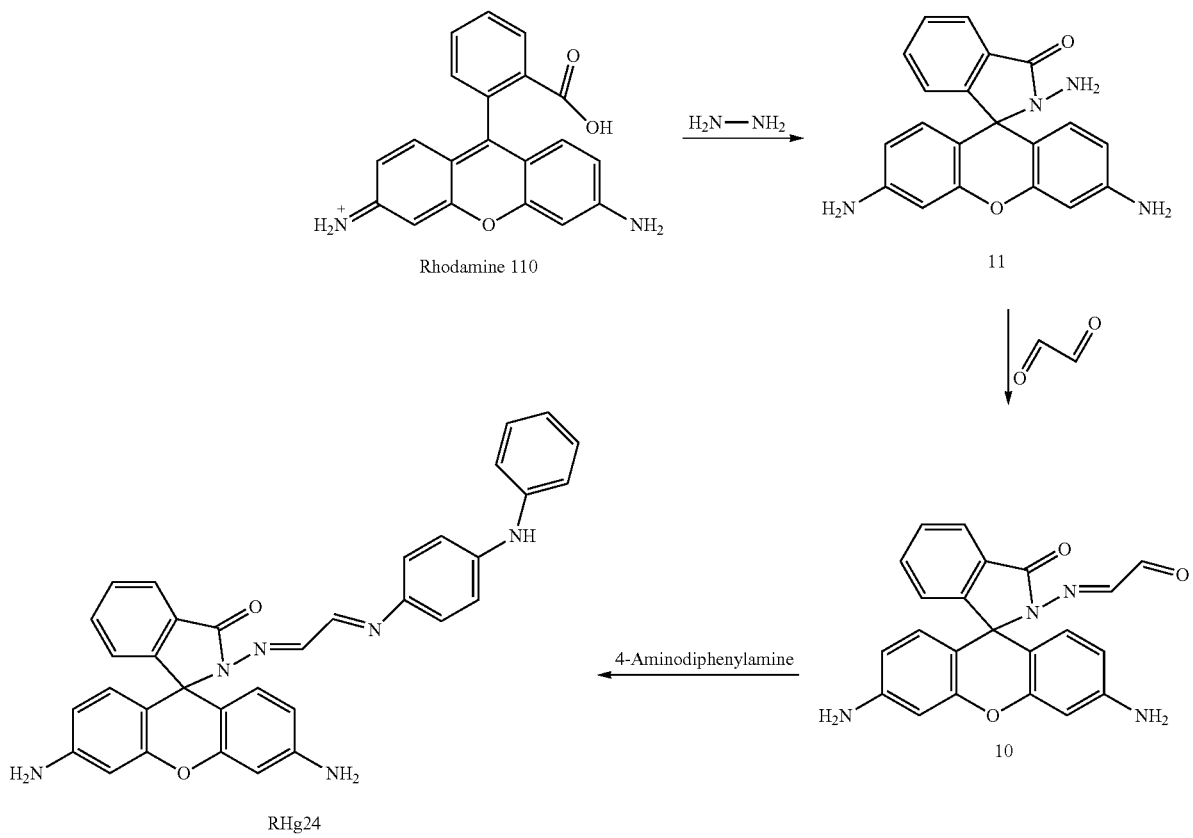

(1) Synthesis of Intermediate 11:

Rhodamine 110 (0.9 g, 2.5 mmol) was added into a 100 ml single-necked flask containing 30 ml ethanol. The mixture was stirred vigorously at room temperature, followed by dropwise addition of excessive amount of 85% hydrazine hydrate solution (3 ml). After finishing the addition of hydrazine hydrage, the mixture was refluxed for 2 h in air until the solution changed from purple to light brown in color and finally became clear. Then the solution was cooled down to room temperature and ethanol was removed under reduced pressure. After that, 50 ml HCl (1 M) was added to give a red solution, and then 70 ml NaOH aqueous solution (1 M) was added under stirring to adjust pH to 9 to 10 to form a large amount of precipitation. The precipitation was filtered and washed with 15 ml water for three times, then dried under vacuum and purified through column chromatography to produce 0.52 g intermediate 11, yield 60%. $^1$H NMR (400 MHz CDCl$_3$) δ (ppm): 3.62(s, 2H), 5.85(s, 4H), 6.14(d, J=8 Hz, 2H), 6.25(m, 4H), 7.10(d, J=8 Hz, 1H), 7.48(t, 2H), 8.02(d, J=8 Hz, 1H); $^{13}$C NMR (400 MHz, CDCl$_3$), δ: 66.04, 98.09, 103.78, 108.17, 123.98, 124.07, 126.58, 128.62, 134.97, 149.21, 152.64, 152.87, 165.87; TOF MS (ES): m/z Calcd for C$_{20}$H$_{17}$N$_4$O$_2^+$: 345.1346, Found: 345.1351.

(2) The Synthesis of Intermediate 10:

The intermediate 11 (0.34 g, 1.0 mmol) was added into a 100 ml single-necked flask, and then absolute ethanol 30 ml and 40% glyoxal aqueous solution (0.58 g, 4.0 mmol) (excessive in amount) were added. The reaction mixture was stirred for 2 h at room temperature under nitrogen protection, and then the solvent was removed under reduced pressure. The product was purified through silica column chromatography with a mixture of petroleum ether (bp 60 to 90° C.) and ethyl acetate (v/v, 5/1) as elution solution to produce 0.31 g yellow solid 10 with a yield of 81%. $^1$H NMR (400 MHz CDCl$_3$) δ (ppm): 5.85(s, 4H), 6.14(d, J=8 Hz, 2H), 6.25(m, 4H), 7.10(d, J=8 Hz, 1H), 7.45(m, J=8 Hz, 1H), 7.48(t, 2H), 8.02(d, J=8 Hz, 1H), 9.42(d, J=8 Hz, 1H); $^{13}$C NMR (400 MHz, CDCl$_3$), δ: 66.04, 98.09, 103.78, 108.17, 123.98, 124.07, 126.58, 128.62, 134.97, 141.22, 149.21, 152.64, 152.87, 165.87, 192.49; TOF MS (ES): m/z Calcd for C$_{22}$H$_{17}$N$_4$O$_3^+$: 385.1295, Found: 385.1283.

(3) The Synthesis of RHg24:

was removed under reduced pressure. The product was purified through silica column chromatography with a mixture of petroleum ether (bp 60-90° C.) and ethyl acetate (v/v, 5/1) as elution solution to produce 0.47 g yellow solid RHg24 with a yield of 83%. $^1$H NMR (400 MHz CDCl$_3$) δ (ppm): 5.85(s, 4H), 6.27(d, J=8 Hz, 2H), 6.44(s, 2H), 6.54(m, 4H), 7.09(m, 4H), 7.31(m, 4H), 7.47(m, 2H), 7.95(d, J=8 Hz, 1H), 8.01(d, J=8 Hz, 1H), 8.34(d, J=8 Hz, 1H), 9.77(s, 1H); $^{13}$C NMR (400 MHz, CDCl$_3$), δ: 68.0, 103.1, 109.9, 114.8, 118.3, 119.1, 120.4, 123.2, 126.4, 128.3, 129.7, 131.3, 132.7, 138.0, 138.5, 139.5, 145.6, 147.5, 151.7, 163.0, 168.0; TOF MS (ES): m/z Calcd for C$_{34}$H$_{27}$N$_6$O$_2^+$: 551.2190, Found: 551.2169.

Example 52

Figure 32:
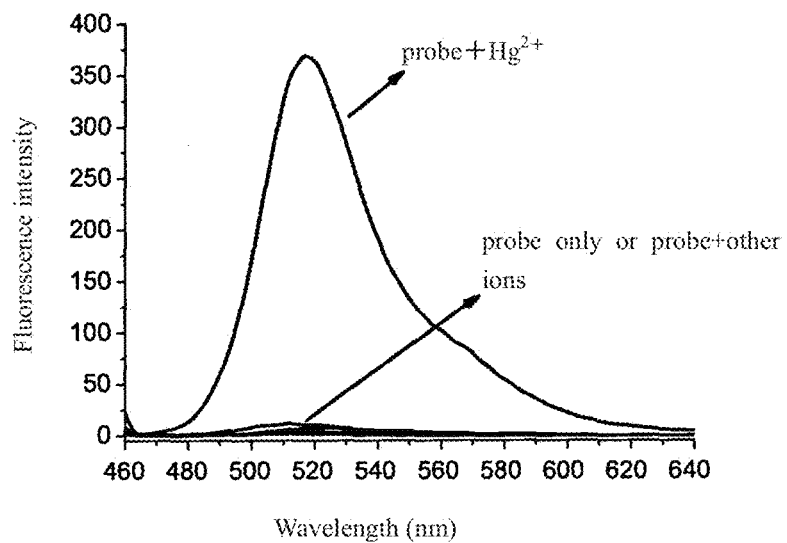
FIG. 32 is fluorescence emission spectra of fluorescence probe RHg24 coordinating $Hg^{2+}$ over other metal ions. Concentration of RHg24 is 5 μM, and concentrations of the metal ions are 50 equivalence ($Hg^{2+}$ is 15 equivalence). X-axis is wavelength (nm) and Y-axis is fluorescence intensity. The instrument is fluorospectrophotometer, model: LS 55.

The Selectivity Test of RHg24 to Hg$^{2+}$:

The synthesized compound RHg24 was adopted to test the selectivity to Hg$^{2+}$. RHg24 (5 μM) was added into ethanol aqueous solution (ethanol/water=1/1, v/v) containing metal ion (50 equivalence, except that Hg$^{2+}$ is 15 equivalence), and then the fluorescence spectrum was tested, the result is shown in FIG. 32. From FIG. 32, it can be seen that, RHg24 exhibits good selectivity to Hg$^{2+}$ and large fluorescence and UV-Vis absorption enhancement is induced by Hg$^{2+}$ without the interference from Na$^+$, K$^+$, Ca$^{2+}$, Mg$^{2+}$, Cu$^{2+}$ and so on. The instrument is fluorospectrophotometer, model: LS 55.

Example 53

The Synthesis of RHg25:

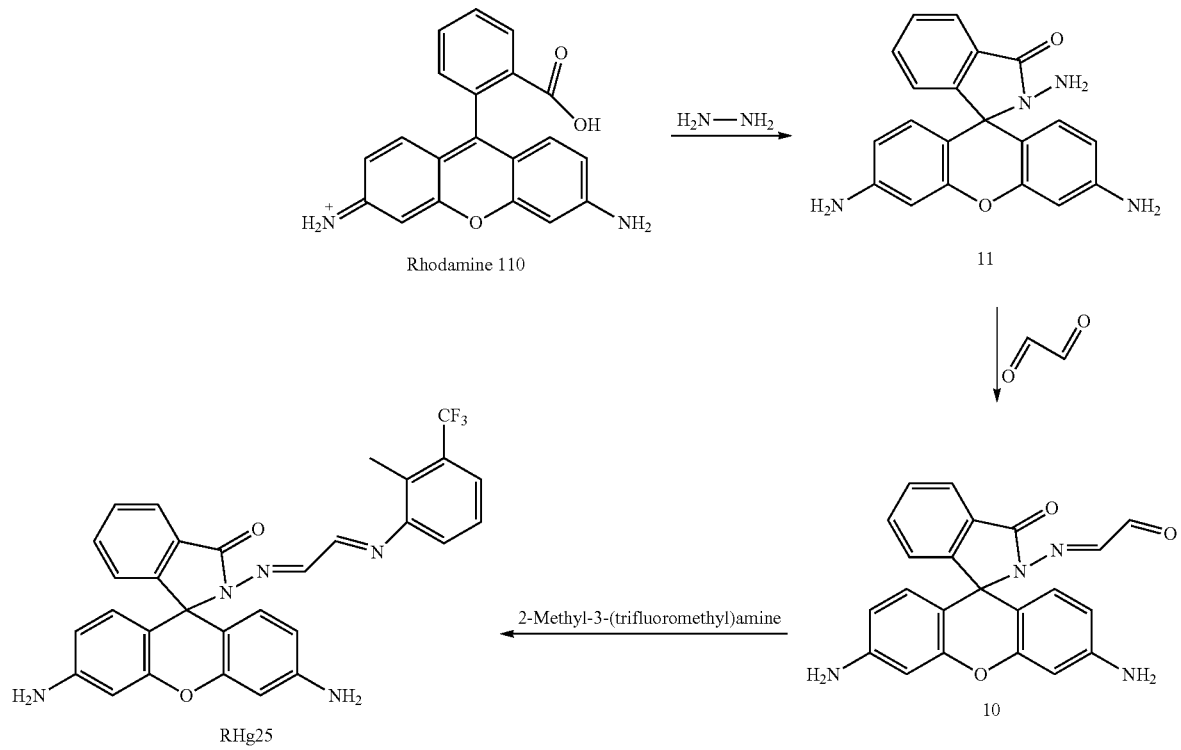

The intermediate 10 (0.38 g, 1 mmol) was added into a 100 ml single-necked flask, and then absolute 30 ml and 4-aminodiphenylamine (0.74 g, 4 mmol) (excessive in amount) were added. The reaction mixture was stirred for 2 h at room temperature under nitrogen protection, and then the solvent (1) Synthesis of Intermediate 11:

Rhodamine 110 (0.9 g, 2.5 mmol) was added into a 100 ml single-necked flask containing 30 ml ethanol. The mixture was stirred vigorously at room temperature, followed by dropwise addition of excessive amount of 85% hydrazine hydrate solution (3 ml). After finishing the addition of hydrazine hydrage, the mixture was refluxed for 2 h in air until the solution changed from purple to light brown in color and finally became clear. Then the solution was cooled down to room temperature and ethanol was removed under reduced pressure. After that, 50 ml HCl (1 M) was added to give a red solution, and then 70 ml NaOH aqueous solution (1 M) was added under stirring to adjust pH to 9 to 10 to form a large amount of precipitation. The precipitation was filtered and washed with 15 ml water for three times, then dried under vacuum and purified through column chromatography to produce 0.52 g intermediate 11, yield 60%. $^1$H NMR (400 MHz CDCl$_3$) δ (ppm): 3.62(s, 2H), 5.85(s, 4H), 6.14(d, J=8 Hz, 2H), 6.25(m, 4H), 7.10(d, J=8 Hz, 1H), 7.48(t, 2H), 8.02(d, J=8 Hz, 1H); $^{13}$C NMR (400 MHz, CDCl$_3$), δ: 66.04, 98.09, 103.78, 108.17, 123.98, 124.07, 126.58, 128.62, 134.97, 149.21, 152.64, 152.87, 165.87; TOF MS (ES): m/z Calcd for $C_{20}H_{17}N_4O_2^+$: 345.1346, Found: 345.1351.

(2) The Synthesis of Intermediate 10:

The intermediate 11 (0.34 g, 1.0 mmol) was added into a 100 ml single-necked flask, and then absolute ethanol 30 ml and 40% glyoxal aqueous solution (0.58 g, 4.0 mmol) (excessive in amount) were added. The reaction mixture was stirred for 2 h at room temperature under nitrogen protection, and then the solvent was removed under reduced pressure. The product was purified through silica column chromatography with a mixture of petroleum ether (bp 60 to 90° C.) and ethyl acetate (v/v, 5/1) as elution solution to produce 0.31 g yellow solid 10 with a yield of 81%. $^1$H NMR (400 MHz CDCl$_3$) δ (ppm): 5.85(s, 4H), 6.14(d, J=8 Hz, 2H), 6.25(m, 4H), 7.10(d, J=8 Hz, 1H), 7.45(m, J=8 Hz, 1H), 7.48(t, 2H), 8.02(d, J=8 Hz, 1H), 9.42(d, J=8 Hz, 1H); $^{13}$C NMR (400 MHz, CDCl$_3$), δ: 66.04, 98.09, 103.78, 108.17, 123.98, 124.07, 126.58, 128.62, 134.97, 141.22, 149.21, 152.64, 152.87, 165.87, 192.49; TOF MS (ES): m/z Calcd for $C_{22}H_{17}N_4O_3^+$: 385.1295, Found: 385.1283.

(3) The Synthesis of RHg25:

The intermediate 10 (0.38 g, 1 mmol) was added into a 100 ml single-necked flask, and then absolute 30 ml and 2-methyl-3-(trifluoromethyl)aniline (0.47 g, 4 mmol) (excessive in amount) were added. The reaction mixture was stirred for 2 h at room temperature under nitrogen protection, and then the solvent was removed under reduced pressure. The product was purified through silica column chromatography with a mixture of petroleum ether (bp 60-90° C.) and ethyl acetate (v/v, 5/1) as elution solution to produce 0.43 g yellow solid RHg25 with a yield of 80%. $^1$H NMR (400 MHz CDCl$_3$) δ (ppm): 2.35(s, 3H), 5.85(s, 4H), 6.27(d, J=8 Hz, 2H), 6.44(s, 2H), 6.54(d, J=8 Hz, 2H), 7.00(m, 1H), 7.09(m, 2H), 7.47(m, 2H), 7.30(d, J=8 Hz, 1H), 7.95(d, J=8 Hz, 1H), 8.01(d, J=8 Hz, 1H), 8.34(d, J=8 Hz, 1H); $^{13}$C NMR (400 MHz, CDCl$_3$), δ: 17.2, 68.0, 114.8, 121.7, 103.1, 109.9, 114.8, 123.5, 124.4, 125.5, 126.4, 127.4, 128.0, 128.4, 129.1, 131.3, 132.7, 139.5, 145.6, 147.5, 151.8, 163.0, 168.0; TOF MS (ES): m/z Calcd for $C_{30}H_{23}F_3N_5O_2^+$: 542.1798, Found: 542.1786.

Example 54

Figure 33:
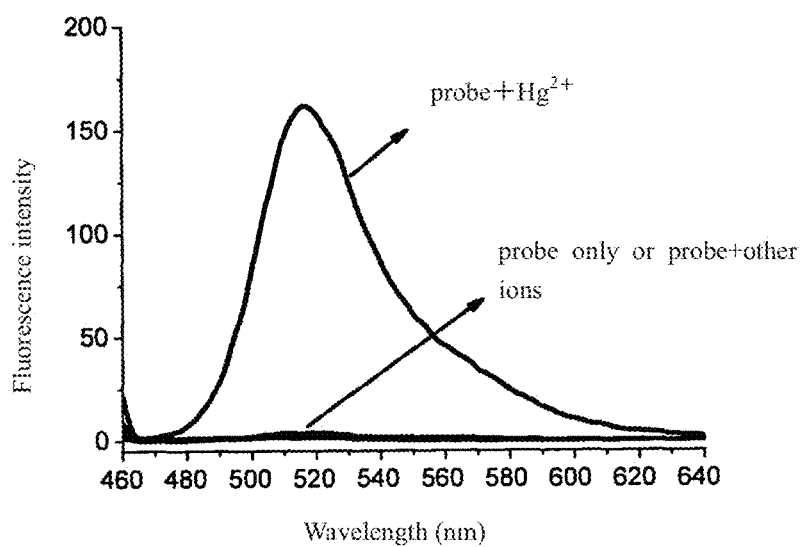
FIG. 33 is fluorescence emission spectra of fluorescence probe RHg25 coordinating $Hg^{2+}$ over other metal ions. Concentration of RHg25 is 5 μM, and concentrations of the metal ions are 50 equivalence ($Hg^{2+}$ is 15 equivalence). X-axis is wavelength (nm) and Y-axis is fluorescence intensity. The instrument is fluorospectrophotometer, model: LS 55.

The Selectivity Test of RHg25 to $Hg^{2+}$:

The synthesized compound RHg25 was adopted to test the selectivity to $Hg^{2+}$. RHg25 (5 μM) was added into ethanol aqueous solution (ethanol/water=1/1, v/v) containing metal ion (50 equivalence, except that $Hg^{2+}$ is 15 equivalence), and then the fluorescence spectrum was tested, the result is shown in FIG. 33. From FIG. 33, it can be seen that, RHg25 exhibits good selectivity to $Hg^{2+}$ and large fluorescence and UV-Vis absorption enhancement is induced by $Hg^{2+}$ without the interference from $Na^+$, $K^+$, $Ca^{2+}$, $Mg^{2+}$, $Cu^{2+}$ and so on. The instrument is fluorospectrophotometer, model: LS 55.

The invention claimed is:

1. A fluorescence probe compound of formula I:

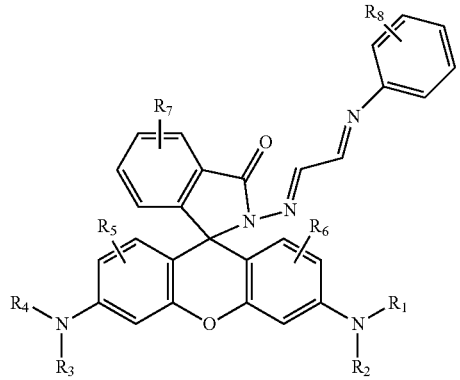

wherein
$R_1$, $R_2$, $R_3$ and $R_4$ are each independently selected from the group consisting of H, $C_{1-18}$ alkyl, $C_{1-18}$ alkyl substituted phenyl, $C_{1-18}$ alkyl substituted naphthyl, halogen, $OR_9$, $N(R_9)_2$, CN, $(CH_2CH_2O)_nH$, $(CH_2)_mCOOM$, and $(CH_2)_mSO_3M$;

$R_5$, $R_6$, $R_7$ and $R_8$ are each independently selected from the group consisting of H, $C_{1-18}$ alkyl, $C_{1-18}$ alkyl substituted phenyl, $C_{1-18}$ alkyl substituted naphthyl, halogen, hydroxyl, mercapto group, cyano group, nitro group, heterocyclic group, halogenated alkyl, alkyl amino group, acylamino group, $OR_9$, $N(R_9)_2$, $(CH_2CH_2O)_nH$, $(CH_2)_mCOOM$ and, $(CH_2)_mSO_3M$;

$R_9$ is selected from the group consisting of H, $C_{1-18}$ alkyl, $C_{1-18}$ alkyl substituted phenyl, $C_{1-18}$ alkyl substituted naphthyl, halogen, CN, $(CH_2CH_2O)_nH$, $(CH_2)_mCOOM$, and $(CH_2)_mSO_3M$;

n and m are integers independently selected from 0 to 18;
M is selected from the group consisting of H, K, Na, Li, $NH_4$, $NH_3R_{10}$, $NH_2(R_{10})_2$, $NH(R_{10})_3$, and $N(R_{10})_4$; and
$R_{10}$ is selected from the group consisting of H, $C_{1-6}$ alkyl, and $CH_2CH_2OH$.

2. The compound according to claim 1, wherein $R_1$, $R_2$, $R_3$ and $R_4$ are each independently selected from the group consisting of H and $C_{1-6}$ alkyl.

3. The compound according to claim 1, wherein $C_{1-18}$ alkyl in $R_5$, $R_6$, $R_7$, $R_8$ and $R_9$ is $C_{1-6}$ alkyl.

4. The compound according to any one of claims 1 to 3, wherein n and m are integers independently selected from 0 to 6.

5. The compound according to claim 1, wherein the compound is

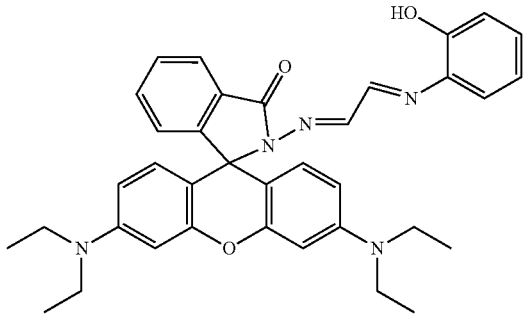

6. A method for preparing a compound of claim 1, comprising the steps of:

(1) synthesis of intermediate II by reacting rhodamine fluorescence dye of formula I' with lactone-ring and hydrazine hydrate II: rhodamine fluorescence dye of formula I' is added into an alcohol solvent and stirred at room temperature so that the rhodamine fluorescence dye is evenly dispersed in the alcohol solvent; hydrazine hydrate in an excessive amount stoichiometrically is added dropwise; after finishing the addition of hydrazine hydrate, the mixture is heated to reflux the solvent and reacted until the reaction solution becomes clear; after the solution is cooled down to room temperature, the solvent is removed by evaporation; acid is added to adjust pH to 2 to 5 and then base solution is added under stirring to adjust pH to 9 to 10 to obtain precipitation; the obtained precipitation is filtered and washed, dried under vacuum and purified by recrystallization or column chromatography;

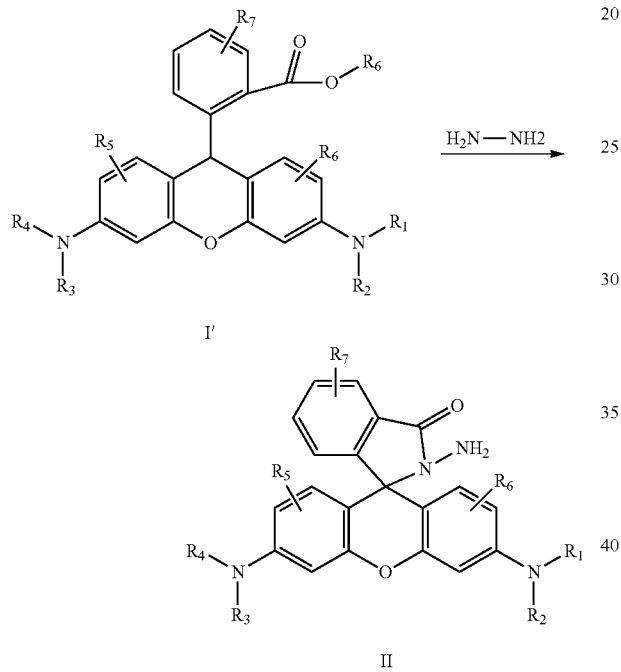

(2) synthesis of compound of formula III by reacting the intermediate II obtained in (1) and glyoxal: the intermediate II is added into reactor, and then alcohol solvent, and glyoxal in an excessive amount stoichiometrically are added; the mixture is stirred and reacted for 1 to 3 h at room temperature; the solvent is removed by evaporation, and purification is carried out through recrystallization or column chromatography to obtain the compound of formula III; and

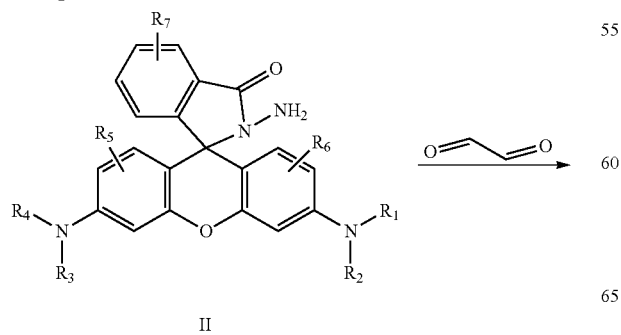

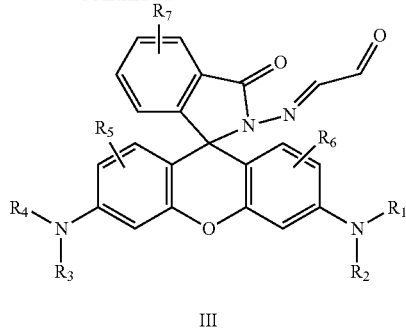

(3) synthesis of compound of formula I by reacting the intermediate III obtained in (2) and $R_8$ substituted aniline compound: the compound of forumula III is added into reactor, and then alcohol solvent and an excessive amount of aniline compound are added; the mixture is stirred and reacted for 1 to 3 h at room temperature; the solvent is removed by evaporation, and purification is carried out through recrystallization or column chromatography to obtain the compound of formula I;

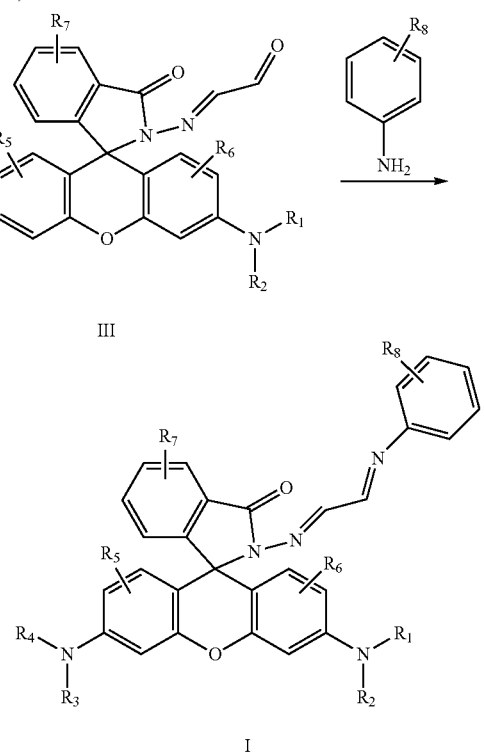

wherein, $R_0$ in formula I' is selected from H or $C_{1-6}$ alkyl, and $R_1$, $R_2$, $R_3$, $R_4$, $R_5$, $R_6$, $R_7$, $R_8$, $R_9$, $R_{10}$, n, m and M in formula I' and formulas I to III are defined as those in claim 1.

7. The method according to claim 6, wherein the rhodamine dye is selected from the group consisting of rhodamine B, rhodamine 110, rhodamine 6G, rhodamine 3GB, rhodamine 3GO, and rhodamine 123.

8. A conjugate comprising a compound according to claim 1.

9. A composition comprising a compound according to claim 1 or a conjugate according to claim 7.

10. A method for detecting $Hg^{2+}$, comprising the steps of:
obtaining a probe solution comprising a compound of claim 1, a conjugate of claim 7, or a composition of claim 8;
adding the probe solution to a sample; and
detecting a fluorescence emission from the sample.

\* \* \* \* \*